US009622849B2

(12) United States Patent
El-Kurdi et al.

(10) Patent No.: US 9,622,849 B2
(45) Date of Patent: Apr. 18, 2017

(54) BIOERODIBLE WRAPS AND USES THEREFOR

(75) Inventors: Mohammed El-Kurdi, Pittsburgh, PA (US); J. Christopher Flaherty, Topsfield, MA (US); Yi Hong, Pittsburgh, PA (US); Jonathan McGrath, Duxbury, MA (US); Lorenzo Soletti, Pittsburgh, PA (US); John Stankus, Campbell, CA (US); David Vorp, Pittsburgh, PA (US); William Wagner, Wexford, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 696 days.

(21) Appl. No.: 13/502,759

(22) PCT Filed: Oct. 28, 2010

(86) PCT No.: PCT/US2010/054444
§ 371 (c)(1),
(2), (4) Date: Sep. 10, 2012

(87) PCT Pub. No.: WO2011/056705
PCT Pub. Date: May 12, 2011

(65) Prior Publication Data
US 2012/0330437 A1    Dec. 27, 2012

Related U.S. Application Data

(60) Provisional application No. 61/255,699, filed on Oct. 28, 2009.

(51) Int. Cl.
*A61F 2/06* (2013.01)
*A61F 2/04* (2013.01)
*A61F 2/07* (2013.01)

(52) U.S. Cl.
CPC ...... *A61F 2/06* (2013.01); *A61F 2/04* (2013.01); *A61F 2/062* (2013.01); *A61F 2002/072* (2013.01)

(58) Field of Classification Search
CPC .............. A61F 2/04; A61F 2/06; A61F 2/062
See application file for complete search history.

(56) References Cited

U.S. PATENT DOCUMENTS

| 5,813,167 A | 9/1998 | Hoshino et al. |
| 6,036,702 A | 3/2000 | Bachinski et al. |

(Continued)

FOREIGN PATENT DOCUMENTS

| CN | 1491728 A | 4/2004 |
| JP | 2004525272 A | 8/2004 |

(Continued)

OTHER PUBLICATIONS

Jankowski-Bell, "Histology of Blood Vessels", available at http://www2.victoriacollege.edu/dept/bio/Belltutorials/Histology%20Tutorial/Blood%20/Vessels/Histology_of_Blood_Vessels.html. Oct. 2006, 7 pages.

(Continued)

*Primary Examiner* — Robert Lynch
(74) *Attorney, Agent, or Firm* — The Webb Law Firm

(57) ABSTRACT

A tubular tissue graft device is provided comprising a tubular member and a restrictive fiber matrix of a bioerodible polymer about a circumference of the tubular tissue. The matrix may be electrospun onto the tubular tissue. In one embodiment, the tubular tissue is from a vein, such as a saphenous vein, useful as an arterial graft, for example and without limitation, in a coronary artery bypass procedure. 5 Also provided is method of preparing a tubular graft comprising depositing a fiber matrix of a bioerodible polymer about a perimeter of a tubular tissue to produce a tubular (Continued)

tissue graft device. A cardiac bypass method comprising bypassing a coronary artery with a tubular tissue graft device comprising a vein and a restrictive fiber matrix of a bioerodible polymer about a circumference of the vein also is provided.

21 Claims, 28 Drawing Sheets

(56) References Cited

U.S. PATENT DOCUMENTS

| | | | |
|---|---|---|---|
| 6,165,212 | A | 12/2000 | Dereume et al. |
| 6,187,038 | B1 | 2/2001 | Sullivan et al. |
| 6,296,863 | B1 | 10/2001 | Trogolo et al. |
| 6,440,163 | B1 | 8/2002 | Swanson et al. |
| 6,599,323 | B2 | 7/2003 | Melican et al. |
| 6,891,077 | B2 | 5/2005 | Rothwell et al. |
| 6,974,586 | B2* | 12/2005 | Greenhalgh et al. ......... 424/423 |
| 7,037,332 | B2 | 5/2006 | Kutryk et al. |
| 7,452,374 | B2 | 11/2008 | Hain et al. |
| 7,759,099 | B2 | 7/2010 | Wolf et al. |
| 7,759,120 | B2 | 7/2010 | Wolf et al. |
| 7,998,188 | B2 | 8/2011 | Zilla et al. |
| 8,057,537 | B2 | 11/2011 | Zilla et al. |
| 8,172,746 | B2 | 5/2012 | Zilla et al. |
| 2002/0042128 | A1 | 4/2002 | Bowlin et al. |
| 2002/0123786 | A1 | 9/2002 | Gittings et al. |
| 2003/0109887 | A1 | 6/2003 | Galdonik et al. |
| 2004/0058887 | A1 | 3/2004 | Bowlin et al. |
| 2004/0094873 | A1 | 5/2004 | Dubson et al. |
| 2004/0146546 | A1 | 7/2004 | Gravett et al. |
| 2004/0171545 | A1 | 9/2004 | Chaikof et al. |
| 2004/0219185 | A1 | 11/2004 | Ringeisen |
| 2005/0203636 | A1 | 9/2005 | McFetridge |
| 2006/0085063 | A1 | 4/2006 | Shastri et al. |
| 2006/0204441 | A1 | 9/2006 | Atala et al. |
| 2006/0240061 | A1 | 10/2006 | Atala et al. |
| 2007/0173917 | A1 | 7/2007 | Hayashi et al. |
| 2007/0239267 | A1 | 10/2007 | Hendriks et al. |
| 2008/0208323 | A1* | 8/2008 | El-Kurdi et al. ............ 623/1.36 |
| 2009/0012607 | A1 | 1/2009 | Kim et al. |
| 2010/0016945 | A1* | 1/2010 | Bogert .................... A61F 2/07 623/1.13 |
| 2010/0160718 | A1 | 6/2010 | Villafana et al. |
| 2010/0221304 | A1* | 9/2010 | Tan ......................... A61F 2/06 424/423 |
| 2010/0280598 | A1 | 11/2010 | Fox |
| 2012/0116495 | A1 | 5/2012 | Zilla et al. |

FOREIGN PATENT DOCUMENTS

| | | |
|---|---|---|
| JP | 2006526658 A | 11/2006 |
| WO | 2004028583 A2 | 4/2004 |
| WO | 2006044904 A2 | 4/2006 |
| WO | 2006119142 A2 | 11/2006 |
| WO | 2009103012 A1 | 8/2009 |
| WO | 2010042721 A1 | 4/2010 |

OTHER PUBLICATIONS

Soletti et al., A Bi-layered Elastomeric Scaffold for Tissue Engineering of Small-Diameter Vascular Grafts, Acta Biomater., Jan. 2010, pp. 110-122, 6(1).
Southgate et al., Involvement of Extracellular-Matrix-Degrading Metalloproteinases in Rabbit Aortic Smooth-Muscle Cell Proliferation, Biochem. J., 1992, pp. 93-99, 288.
Stankus et al., Fabrication of Biodegradable Elastomeric Scaffolds with Sub-Micron Morphologies, J. Biomed. Mater Res., 2004, pp. 603-614, 70A.
Stankus et al., Microintegrating Smooth Muscle Cells into a Biodegradable, Elastomeric Fiber Matrix, Biomaterials, 2006, pp. 735-744, 27.
Stankus et al., Fabrication of Cell Microintegrated Blood Vessel Constructs Through Electrohydrodynamic Atomization, Biomaterials, 2007, pp. 2738-2746, 28.
Stooker et al., Pressure-Diameter Relationship in the Human Greater Saphenous Vein, Ann. Thorac. Surg., 2003, pp. 1533-1538, 76.
Sumpio, Hemodynamic Forces and Vascular Cell Biology, 1993, R.G. Landes Company, Austin.
Szilagyi et al., Biologic Fate of Autogenous Vein Implants as Arterial Substitutes: Clinical, Angiographic and Histopathologic Observations in Femoro-Popliteal Operations for Atherosclerosis, Ann. Surg., Sep. 1973, pp. 232-246, 178(3).
Tai et al., Compliance Properties of Conduits Used in Vascular Reconstruction, Br. J. Surg., 2000, pp. 1516-1524, 87.
Temple et al., Electrostatic Transportation of Living Cells Through Air, Abstracts of Papers, 223 ACS National Meeting, Apr. 7-11, 2002, Orlando, FL.
Tu et al., Migfilin and Mig-2 Link Focal Adhesions to Filamin and the Actin Cytoskeleton and Function in Cell Shape Modulation, Cell., Apr. 4, 2003, pp. 37-47, 113.
Tyagi et al., Stretch-Induced Membrane Type Matrix Metalloproteinase and Tissue Plasminogen Activator in Cardiac Fibroblast Cells, J. Cell Physiol., 1998, pp. 374-382, 176.
Uzui et al., The Role of Protein-Tyrosine Phosphorylation and Gelatinase Production in the Migration and Proliferation of Smooth Muscle Cells, Atherosclerosis, 2000, pp. 51-59, 149.
Veazey et al., Mammalian Cell Delivery via Aerosol Deposition, J. Biomed. Mater. Res. Part B, 2005, pp. 334-338, 72B.
Vijayan et al., External Supports and the Prevention of Neointima Formation in Vein Grafts, Eur. J. Vasc. Endovasc. Surg., 2002, pp. 13-22, 24.
Vijayan et al., Long-Term Reduction of Medial and Intimal Thickening in Porcine Saphenous Vein Grafts with a Polyglactin Biodegradable External Sheath, J. Vasc. Surg., 2004, pp. 1011-1019, 40.
Vorp et al., Modeling the Transmural Stress Distribution During Healing of Bioresorbable Vascular Prostheses, Ann. Biomed. Eng., 1995, pp. 178-188, 23.
Vorp et al., A Device for the Application of Cyclic Twist and Extension on Perfused Vascular Segments, Am. J. Physiol., 1996, pp. H787-H795, 270.
Wang et al., Expression of Apoptosis-Related Proteins and Structural Features of Cell Death in Explanted Aortocoronary Saphenous Vein Bypass Grafts, Cardiovasc. Surg., 2001, pp. 319-328, 9(4).
Wang et al., Regulation of Vein Graft Hyperplasia by Survivin, an Inhibitor of Apoptosis Protein, Arterioscler. Thromb. Vasc. Biol., Aug. 25, 2005, pp. 2081-2087, 25.
Wesly et al., Static Linear and Nonlinear Elastic Properties of Normal and Arterialized Venous Tissue in Dog and Man, Circ. Res., 1975, pp. 509-520, 37.
Wolf et al., Antibodies Against Transforming Growth Factor-Beta 1 Suppress Intimal Hyperplasia in a Rat Model, J. Clin. Invest., 1994, pp. 1172-1178, 93.
Wolff et al., Transforming Growth Factor-Beta1 Antisense Treatement of Rat Vein Grafts Reduces the Accumulation of Collagen and Increases the Accumulation of H-Caldesmon, J. Vasc. Surg., 2006, pp. 1028-1036, 43.
Wu et al., Integrin-Linked Kinase (ILK) and its Interactors: A New Paradigm for the Coupling of Extracellular Matrix to Actin Cytoskeleton and Signaling Complexes, J. Cell. Biol., Nov. 12, 2001, pp. 505-510, 155(4).
Wu, Integrin-Linked Kinase and PINCH: Partners in Regulation of Cell-Extracellular Matrix Interaction and Signal Transduction, J. Cell. Sci., 1999, pp. 4485-4489, 112.
Xu et al., Aligned Biodegradable Nanofibrous Structure: A Potential Scaffold for Blood Vessel Engineering, Biomaterials, 2004, pp. 877-886, 25.
Yamaoka et al., TIMP-1 Production by Human Scleral Fibroblast Decreases in Response to Cyclic Mechanical Stretching, Opthalmic Research, 2001, pp. 98-101, 33.
Zhang et al., Association of Smooth Muscle Cell Phenotypic Modulation with Extracellular Matrix Alterations During Neointima Formation in Rabbit Vein Grafts, J. Vasc. Surg., 1999, pp. 169-183, 30.

(56) References Cited

OTHER PUBLICATIONS

Zuckerbraun et al., Overexpression of Mutated I-kappa B-alpha Inhibits Vascular Smooth Muscle Cell Proliferation and Intimal Hyperplasia Formation, J. Vasc. Surg., 2003, pp. 812-819, 38.

Zwolak et al., Kinetics of Vein Graft Hyperplasia: Association with Tangential Stress, Journal of Vasc. Surg., 1987, pp. 126-136, 5.

Kamenz et al., Incidence of Intimal Proliferation and Apoptosis Following Balloon Angioplasty in an Atherosclerotic Rabbit Model, Cardiovasc. Res., 2000, pp. 766-776, 45.

Kanjickal et al., Polymeric Sustained Local Drug Delivery System for the Prevention of Vascular Intimal Hyperplasia, J. Biomed. Mater Res., 2004, pp. 489-495, 68A.

Karayannacos et al., Late Failure in Vein Grafts: Mediating Factors in Subendothelial Fibromuscular Hyperplasia, Ann. Surg., Feb. 1978, pp. 183-188.

Kohler et al., The effect of Rigid External Support on Vein Graft Adaptation to the Arterial Circulation, J. Vasc. Surg., 1989, pp. 277-285, 9.

Kohler et al., Inhibition of Neointimal Hyperplasia in a Sheep Model of Dialysis Access Failure with the Bioabsorbable Vascular Wrap Paclitaxel-Eluting Mesh, J. Vasc. Surg. 2007, pp. 1029-1038, 45.

Labadie et al., Pulsatile Perfusion System for Ex Vivo Investigation of Biochemical Pathways in Intact Vascular Tissue, Am. J. Physiol., 1996, pp. H760-H768, 270.

Lafleur et al., Activation of Pro-(matrix metalloproteinase-2) (pro-MMP-2) by Thrombin is Membrane-Type-MMP-Dependent in Human Umbilical Vein Endothelial Cells and Generates a Distinct 63 kDa Active Species, Biochem. J., 2001, pp. 107-115, 357.

Lee et al., Nanofiber Alignment and Direction of Mechanical Strain Affect the ECM Production of Human ACL Fibroblast, Biomaterials, 2005, pp. 1261-1270, 26.

Lee et al., Theoretical Hydraulic Consequences of Vein Graft Taper, J. Vasc. Surg., 2003, pp. 785-792, 38.

Liao et al., A Novel Time-Varying Poly Lactic-Co Glycolic Acid External Sheath for Vein Grafts Designed Under Physiological Loading, Tissue Eng., 2007, pp. 2855-2862, 13(12).

Ligush, Jr. et al., Evaluation of Endothelium-Derived Nitric Oxide Mediated Vasodilation Utilizing Ex Vivo Perfusion of an Intact Vessel, J. Surg. Res., 1992, pp. 416-421, 52.

Lijnen et al., Tissue Inhibitor of Matrix Metalloproteinases-1 Impairs Arterial Neointima Formation After Vascular Injury in Mice, Circ. Res., 1999, pp. 1186-1191, 85.

Liu et al., The Signaling Protein Rho is necessary for Vascular Smooth Muscle Migration and Survival but not for Proliferation, Surgery, 2002, pp. 317-325, 132.

Liu et al., Changes in the Organization of the Smooth Muscle Cells in Rat Vein Grafts, Ann. Biomed. Eng., 1998, pp. 86-95, 26.

Liu et al., A Possible Role of Initial Cell Death Due to Mechanical Stretch in the Regulation of Subsequent Cell Proliferation in Experimental Vein Grafts, Biomech. Model Mechanobiol., 2002, pp. 17-27, 1.

Liu et al., Partial Prevention of Monocyte and Granulocyte Activation in Experimental Vein Grafts by Using a Biomechanical Engineering Approach, J. Biomech., 1999, pp. 1165-1175, 32.

Mavromatis et al., Early Effects of Arterial Hemodynamic Conditions on Human Saphenous Veins Perfused Ex Vivo, Arterioscler. Thromb. Vasc. Biol., 2000, pp. 1889-1895, 20.

Mehta et al., External Stenting Reduces Long-Term Medial and Neointimal Thickening and Platelet Derived Growth Factor Expression in a Pig Model of Arteriovenous Bypass Grafting, Nat. Med., Feb. 1998, pp. 235-239, 4(2).

Meng et al., Mechanical Stretching of Human Saphenous Vein Grafts Induces Expression and Activation of Matrix-Degrading Enzymes Associated with Vascular Tissue Injury and Repair, Exp. Mol. Pathol., 1999, pp. 227-237, 66.

Mii et al., Transforming Growth Factor-Beta Inhibits Human Vascular Smooth Muscle Cell Growth and Migration, Surgery, 1993, pp. 464-470, 114.

Morinaga et al., Effect of Wall Shear Stress on Intimal Thickening of Arterially Transplanted Autogenous Veins in Dogs, J. Vasc. Surg., 1985, pp. 430-433, 2.

Morisaki et al., Cell Cycle-Dependent Inhibition of DNA Synthesis by Prostaglandin I2 in Cultured Rabbit Aortic Smooth Muscle Cells, Atherosclerosis, 1988, pp. 165-171, 71.

Moritz et al., A Method for Constricting Large Veins for Use in Arterial Vascular Reconstruction, Artificial Organs, 1990, pp. 394-398, 14(5).

Muluk et al., Enhancement of Tissue Factor Expression by Vein Segments Exposed to Coronary Arterial Hemodynamics, J. of Vasc. Surg., 1998, pp. 521-527, 27.

Murphy-Ullrich et al., Focal Adhesion Integrity is Downregulated by the Alternatively Spliced Domain of Human Tenascin., J. Cell Biol., Nov. 1991, pp. 1127-1136, 115(4).

Murphy-Ullrich, The De-adhesive Activity of Matricellular Proteins: Is Intermediate Cell Adhesion an Adaptive State?, J. Clin. Invest., Apr. 2001, pp. 785-790, 107(7).

Nagai et al., Identification of Two Types of Smooth Muscle Myosin Heavy Chain Isoforms by cDNA Cloning and Immunoblot Analysis, The Journal of Biological Chemistry, Jun. 15, 1989, pp. 9734-9737, 264(17).

Nakazawa et al., Smooth Muscle Cell Migration Induced by Shear-Loaded Platelets and Endothelial Cells. Enhanced Platelet-Derived Growth Factor Production by Shear-Loaded Platelets, Int. Angiol., Jun. 2000, pp. 142-146, 19.

Nedovic et al., Cell Immobilisation by Electrostatic Droplet Generation, Landbauforsch Volk., 2002, pp. 11-17, (241).

Newby et al., Extracellular Matrix Degrading Metalloproteinases in the Pathogensis of Arteriosclerosis, Basic Res. Cardiol., 1994, pp. 59-70, 89(Suppl 1).

Nikolopoulos et al., Integrin-Linked Kinase (ILK) Binding to Paxillin LD1 Motif Regulates ILK Localization to Focal Adhesions, J. Biol. Chem., Jun. 29, 2001, pp. 23499-23505, 276(26).

Nishibe et al., Induction of Angiotensin Converting Enzyme in Neointima After Intravascular Stent Placement, Int. Angiol., Sep. 2002, pp. 250-255, 21(3).

Parsonnet et al., New Stent for Support of Veins in Arterial Grafts, Arch. Surg., Oct. 1963, pp. 696-702, 87.

Pintucci et al., Anti-Proliferative and Anti-Inflammatory Effects of Topical MAPK Inhibition in Arterialized Vein Grafts, Faseb J., 2006, pp. 398-400, 20(2).

Porter et al., Marimastat Inhibits Neointimal Thickening in a Model of Human Vein Graft Stenosis, Br. J. Surg., 1998, pp. 1373-1377, 85.

Porter et al., Simvastatin Inhibits Human Saphenous Vein Neointima Formation via Inhibition of Smooth Muscle Cell Proliferation and Migration, J. Vasc. Surg., 2002, pp. 150-157, 36.

Porter et al., The Development of an In Vitro Flow Model of Human Saphenous Vein Graft Intimal Hyperplasia, Cardiovasc. Res., 1996, pp. 607-614, 31.

Porter et al., Production and Inhibition of the Gelatinolytic Matrix Metalloproteinases in a Human Model of Vein Graft Stenosis, Eur. J. Vasc. Endovasc. Surg., 1999, pp. 404-412, 17.

Powell et al., Matirix-Specific Effect of Endothelial Control of Smooth Muscle Cell Migration, J. Vasc. Surg., 1996, pp. 51-57, 24.

Predel et al., Implications of Pulsatile Stretch on Growth of Saphenous Vein and Mammary Artery Smooth Muscle, Lancet., Oct. 10, 1992, pp. 878-879, 340.

Qian et al., Gene Expression of bFGF and Intimal Hyperplasia of Autologous Vein Grafts in Rats, Nat'l. Med. J. China. Nov. 1996, pp. 826-828, 76(11).

Ramos et al., Histologic Fate and Endothelial Changes of Distended and Nondistended Vein Grafts, Ann. Surg., Mar. 1976, pp. 205-228, 183(3).

Redmond et al., Effect of Pulse Pressure on Vascular Smooth Muscle Cell Migration: The Role of Urokinase and Matrix Metalloproteinase, Thromb. & Haemost., 1999, pp. 293-300, 81.

Resnick et al., Hemodynamic Forces are Complex Regulators of Endothelial Gene Expression, The Faseb. J., 1995, pp. 874-882, 9.

Rho et al., Electrospinning of Collagen Nanofibers: Effects on the Behavior of Normal Human Keratinocytes and Early-Stage Wound Healing, Biomaterials, 2006, pp. 1452-1461, 27.

(56) References Cited

OTHER PUBLICATIONS

Sage et al., Extracellular Proteins that Modulate Cell-Matrix Interactions, Sparc, Tenascin, and Thrombospondin., J. Biol. Chem., Aug. 15, 1991, pp. 14831-14834, 266(23).
Severyn et al., The Influence of Hemodynamics and Wall Biomechanics on the Thrombogenicity of Vein Segments Perfused In Vitro, J. Surg. Res., 2004, pp. 31-37, 121.
Shigematsu et al., Direct and Indirect Effects of Pulsatile Shear Stress on the Smooth Muscle Cell, Int. Angiol., 2000, pp. 39-46, 19(1).
Sho et al., Subnormal Shear Stress-Induced Intimal Thickening Requires Medial Smooth Muscle Cell Proliferation and Migration, Exp. Mol. Pathol., 2002, pp. 150-160, 72.
Simosa et al., Survivin Expression is Up-Regulated in Vascular Injury and Identifies a Distinct Cellular Phenotype, J. Vasc. Surg., 2005, pp. 682-690, 41.
Alcocer et al., Mutual Exclusion of Apoptosis and HSP 70 in Human Vein Intimal Hyperplasia In Vitro, J. Surg. Res. 2001, pp. 75-80, 96.
Angelini et al., Distention Promotes Platelet and Leukocyte Adhesion and Reduces Short-Term Patency in Pig Arteriovenous Bypass Grafts, J. Thorac. Cardiovasc. Surg., 1990, pp. 433-439, 99.
Annabi et al., Differential Regulation of Matrix Metalloproteinase Activities in Abdominal Aortic Aneurysms, J. Vasc. Surg., 2002, pp. 539-546, 35.
Asanuma et al., Uniaxial Strain Upregulates Matrix-Degrading Enzymes Produced by Human Vascular Smooth Muscle Cells, Am. J. Physiol. Heart Circ. Physiol., 2003, pp. H1778-H1784, 284.
Bandyk et al., The Failing Graft: An Evolving Concept, Semin. Vasc. Surg., Jun. 1993, pp. 75-77, 6(2).
Bassiouny et al., Anastomotic Intimal Hyperplasia: Mechanical Injury or Flow Induced, J. Vasc. Surg., 1992, pp. 708-717, 15.
Bassiouny et al., Low Flow Enhances Platelet Activation After Acute Experimental Arterial Injury, J. Vasc. Surg., 1998, pp. 910-918, 27.
Berkowitz et al., Reversed Vein Graft Stenosis: Early Diagnosis and Management, J. Vasc. Surg., 1992, pp. 130-142, 15.
Bornstein, Diversity of Function is Inherent in Matricellular Proteins: An Appraisal of Thrombospondin 1, J. Cell. Biol., Aug. 1995, pp. 503-506, 130(3).
Brant et al., Measurement In Vitro of Pulsatile Arterial Diameter Using a Helium-Neon Laser, J. Appl. Physiol., 1987, pp. 679-683, 62(2).
Bunt, Synthetic Vascular Graft Infections. I. Graft Infections, Surgery, 1983, pp. 733-746, 93(6).
Cabrera Fischer et al., Reduced Elastic Mismatch Achieved by Interposing Vein Cuff in Expanded Polytetrafluoroethylene Femoral Bypass Decreases Intimal Hyperplasia, Artif. Organs, 2005, pp. 122-130, 29(2).
Cagiannos et al., Rapamycin-Coated Expanded Polytetrafluoroethylene Bypass Grafts Exhibit Decreased Anastomotic Neointimal Hyperplasia in a Porcine Model, J. Vasc. Surg., Nov. 2005, pp. 980-988, 42(5).
Campbell et al., Arterial Smooth Muscle, A Multifunctional Mesenchymal Cell. Arch Pathol. Lab Med., Oct. 1988, pp. 977-986, 112(10).
Campbell et al., Vein Grafts for Arterial Repair: Their Success and Reasons for Failure, Ann. R. Coll. Surg. Engl., 1981, pp. 257-260, 63.
Campeau et al., Natural History of Saphenous Vein Aortocoronary Bypass Grafts, Mod. Concepts Cardiovasc. Dis., Nov. 1984, pp. 59-63, 53(11).
Cho et al., Matrix Metalloproteinase-9 is Necessary for the Regulation of Smooth Muscle Cell Replication and Migration After Arterial Injury, Circ. Res. 2002, pp. 845-851, 91.
Davies et al., Prevention of Malignment During Non-Reversed Femorodistal Bypass, Ann. R. Coll. Surg. Engl., 1992, pp. 434-435, 74.
Davies et al., Pre-Bypass Morphological Changes in Vein Grafts, Eur. J. Vasc. Surg., 1993, pp. 642-647, 7.
Dethlefsen et al., Comparison of the Effects of Mechanical Stimulation on Venous and Arterial Smooth Muscle Cells In Vitro, J. Vasc. Res., 1996, pp. 405-413, 33.
Dobrin et al., Mechanical Factors Predisposing to Intimal Hyperplasia and Medial Thickening in Autogenous Vein Grafts, Surgery, 1989, pp. 393-400, 105.
Ducasse et al., Interposition Vein Cuff and Intimal Hyperplasia: An Experimental Study, Eur. J. Vasc. Endovasc. Surg., 2004, pp. 617-621, 27.
Edwards et al., Primary Graft Infections, J. Vasc. Surg., 1987, pp. 235-239, 6.
Francis et al., Release of Platelet-Derived Growth Factor Activity from Pig Venous Arterial Grafts, J. Thorac. Cardiovasc. Surg., 1994, pp. 540-548, 108.
Fuchs et al., Postoperative Changes in Autologous Vein Grafts, Ann Surg., Jul. 1978, pp. 1-15, 188(1).
Fujimoto et al., In Vivo Evaluation of a Porous, Elastic, Biodegradable Patch for Reconstructive Cardiac Procedures, Ann Thorac. Surg., 2007, pp. 648-654, 83.
Fujimoto et al., An Elastic, Biodegradable Cardiac Patch Induces Contractile Smooth Muscle and Improves Cardiac Remodeling and Function in Subacute Myocardial Infarction, J. Am. Coll. Cardiolo., 2007, pp. 2292-3000, 49(23).
Galis et al., Cytokine-Stimulated Human Vascular Smooth Muscle Cells Synthesize a Complement of Enzymes Required for Extracellular Matrix Digestion, Circulation Research, 1994, pp. 181-189, 75.
Garanich et al., Shear Stress Inhibits Smooth Muscle Cell Migration via Nitric Oxide-Mediated Downregulation of Matrix Metalloproteinase-2 Activity, Am. J. Physiol. Heart Circ. Physiol., 2005, pp. H2244-H2252, 288.
George et al., Gene Transfer of Tissue Inhibitor of Metalloproteinase-2 Inhibits Metalloproteinase Activity and Neointima Formation in Human Saphenous Veins, Gene Ther., 1998, pp. 1552-60, 5.
George et al., Adenovirus-Mediated Gene Transfer of the Human TIMP-1 Gene Inhibits Smooth Muscle Cell Migration and Neointimal Formation in Human Saphenous Vein, Hum. Gene Ther, Apr. 10, 1998, pp. 867-877, 9.
George et al., Surgical Preparative Injury and Neointima Formation Increase MMP-9 Expression and MMP-2 Activation in Human Saphenous Vein, Cardiovasc. Res., 1997, pp. 447-459, 33.
Goldman et al., Degradation of Alpha-Actin Filaments in Venous Smooth Muscle Cells in Response to Mechanical Stretch, Am. J. Physiol. Heart Circ. Physiol., 2003, pp. H1839-H1847, 284.
Goldman et al., Negative Regulation of Vascular Smooth Muscle Cell Migration by Blood Shear Stress, Am. J. Physiol. Heart Circ. Physiol., 2007, pp. H928-H938, 292.
Greenwood et al., Restructuring of Focal Adhesion Plaques by Pi 3-Kinase: Regulation by PtdIns (3,4,5)-P3 Binding to Alpha-Actinin, J. Cell. Biol., Aug. 7, 2000, pp. 627-641, 150(3).
Grote et al., Mechanical Stretch Enhances mRNA Expression and Proenzyme Release of Matrix Metalloproteinase-2 (MMP-2) via NAD(P)H Oxidase-Derived Reactive Oxygen Species, Circulation Research, 2003, pp. e80-e86, 92.
Guan et al., Synthesis, Characterization, and Cytocompatibility of Elastomeric, Biodegradable Poly(ester-urethane) ureas Based on Poly(caprolactone) and Putrescine, J. Biomed. Mater Res., 2002, pp. 493-503, 61.
Gusic et al., Shear Stress and Pressure Modulate Saphenous Vein Remodeling Ex Vivo, J. Biomech., 2005, pp. 1760-1769, 38.
Hayashi, Experimental Approaches on Measuring the Mechanical Properties and Constitutive Laws of Arterial Walls, J. Biomech. Eng., Nov. 1993, pp. 481-488, 115.
He et al., Arterial Replacement with Compliant Hierarchic Hybrid Vascular Graft: Biomechanical Adaptation and Failure Tissue Engineering, 2002, pp. 213-224, 8(2).
Hilker et al., Bypass Graft Disease: Analysis of Proliferative Activity in Human Aorto-Coronary Bypass Grafts, Heart Surg. Forum, 2002, pp. S331-S341, 5 Suppl. 4.
Hu et al., Activation of PDGF Receptor Alpha in Vascular Smooth Muscle Cells by Mechanical Stress, Faseb J., 1998, pp. 1135-1142, 12.

(56) References Cited

OTHER PUBLICATIONS

Huynh et al., Alterations in Wall Tension and Shear Stress Modulate Tyrosine Kinase Signaling and Wall Remodeling in Experimental Vein Grafts, J. Vasc. Surg., 1999, pp. 334-344, 29.
Huynh et al., External Support Modulates G Protein Expression and Receptor Coupling in Experimental Vein Grafts, Surgery, Aug. 1999, pp. 127-134, 126(2).
Igase et al., Apoptosis and Bcl-xs in the Intimal Thickening of Balloon-Injured Carotid Arteries, Clin. Sci. (Lond.), 1999, pp. 605-612, 96.
Jacot et al., Early Adaptation of Human Lower Extremity Vein Grafts: Wall Stiffness Changes Accompany Geometric Remodeling, J. Vasc. Surg., Mar. 2004, pp. 547-555, 39(3).
Jeremy et al., A Bioabsorbable (polyglactin), Nonrestrictive, External Sheath Inhibits Porcine Saphenous Vein Graft Thickening, J. Thorac Cardiovasc., Surg., Jun. 2004, pp. 1766-1772, 127(6).
Jeremy et al., Nitric Oxide Synthase and Adenylyl and Guanylyl Cyclase Activity in Porcine Interposition Vein Grafts, Ann. Thorac. Surg., 1997, pp. 470-476, 63.
Jiang et al., Wall Shear Modulation of Cytokines in Early Vein Grafts, J. Vasc. Surg., 2004, pp. 345-350, 40.
Jiang et al., A Novel Vein Graft Model: Adaptation to Differential Flow Enviornments, Am. J. Physiol. Heart Circ. Physiol., 2004, pp. H240-H245, 286.
Ayres, et al. Modulation of anisotropy in electrospun tissue-engineering scaffolds: Analysis of fiber alignment by the fast Fourier transform. Biomaterials 27 (2006) 5524-5534.
Ben-Gal, et al. Expandable external support device to improve saphenous vein graft patency after cabg. J Cardiothorac Surg 2013;8:122.
Chakrabarty, S. Fibrin solubilizing properties of certain anionic and cationic detergents. Thrombosis research 55.4 (1989): 511-519.
Courtney, et al. Design and anlysis of tissue engineering scaffolds that mimic soft tissue mechanical anisotropy. Biomaterials. 2006, 27: 3631-3638.
Deitzel, et al. The effect of processing variable on the morphology of electrospun nanofibers and textiles. Polymer 42 (2001): 261-272.
Deitzel, et al. Controlled deposition of electrospun poly(ethylene oxide) fibers. Polymer. 2001, 42: 8163-8170.
Hermans, et al. Fibrin: structure and interactions. Seminars in thrombosis and hemostasis. vol. 8. No. 1. 1982.
International preliminary report on patentability and written opinion dated Aug. 2, 2011 for PCT Application No. US2010/054444.
International search report and written opinion dated Aug. 2, 2011 for PCT Application No. US2010/054444.
Izzat, et al. Influence of external stent size on early medial and neointimal thickening in a pig model of saphenous vein bypass graftin. Circulation 1996; 94:1741-5.
Jeremy, et al. A bioabsorbable (polyglactin), nonrestrictive, external sheath inhibits porcine saphenous vein graft thickening. J Thorac Cardiovasc Surg. 2004;127(6): 1766-72.
Jones, et al. Water and Electrolyte Content of Normal and Hypertensive Arteries in Dogs. Circulation Research, 1964; 15:386-392.
Levorson, et al. Fabrication and characterization of multiscale electrospun scaffolds for cartilage regeneration. Biomed Mater 2013;8:014103. doi:10.1088/1748-6041/8/1/014103.

McManus, et al. Electrospun fibrinogen: feasibility as a tissue engineering scaffold in a rat cell culture model. Journal of Biomedical Materials Research Part A 81.2 (2007): 299-309.
McManus, et al. Mechanical properties of electrospun fibrinogen structures. Acta Biomaterialia 2.1 (2006): 19-28.
Morton, et al. Electrospun fibrin nanofibers for the use in tissue engineering. Modification of fibrin to improve applications in regenerative medicine (2010): 81.
Mosesson, M. W. Fibrinogen and fibrin structure and functions. Journal of Thrombosis and Haemostasis 3.8 (2005): 1894-1904.
Perumcherry, et al. A Novel Method for the Fabrication of Fibrin-Based Electrospun Nanofibrous Scaffold for Tissue-Engineering Applications*. Tissue Engineering Part C: Methods 17.11 (2011): 1121-1130.
Sell, et al. Cross-linking methods of electrospun fibrinogen scaffolds for tissue engineering applications. Biomedical Materials 3.4 (2008): 045001.
Sreerekha, et al. Fabrication of fibrin based electrospun multiscale composite scaffold for tissue engineering applications. Journal of biomedical nanotechnology 9.5 (2013): 790-800.
Stitzel, et al. Controlled fabrication of a biological vascular substitute. Biomaterials. 2006, 27: 1088-1094.
Stocker, et al. Perivenous application of fibrin glue reduces early injury to the human saphenous vein graft wall in an ex vivo model. European Journal of Cardio-thoracic Surgery. 2002, 21: 212-217.
Sun, et al. On the Poisson's rations of a woven fabric. Composite Structures 68 (2005): 505-510.
Traver, et al. New Generation Tissue Sealants and Hemostatic Agents: Innovative Urologic Applications. Reviews in Urology. 2006, 8: 104-111.
Wan, et al. Differential, time-dependent effects of perivenous application of fibrin glue on medial thickening in porcine saphenous vein grafts. European Journal of Cardio-thoracic Surgery, 29, (2006): 742-747.
Weisel, et al. Computer modeling of fibrin polymerization kinetics correlated with electron microscope and turbidity observations: clot structure and assembly are kinetically controlled. Biophysical journal 63.1 (1992): 111.
Weisel, et al. Mechanisms of fibrin polymerization and clinical implications. Blood 121.10 (2013): 1712-1719.
Wnek, et al. Electrospinning of nanofiber fibrinogen structures. Nano Letters 3.2 (2003): 213-216.
Xu, et al. Electrospun Nanofiber Fabrication as Synthetic Extracellular Matrix and Its Potential for Vascular Tissue Engineering. Tissue Engineering, vol. 10, No. 7/8, 2004.
Yu, et al. Electrospinning, Encyclopedia of Polymer Science & Technology (2008) 1-20.
Zhang, et al. Evaluating the Mechanical Behavior of Arterial Tissue using Digital Image Correlation. Experimental Mechanics, vol. 42, No. 4, Dec. 2002, pp. 409-416.
Zilla, et al. Utilization of shape memory in external vein-graft meshes allows extreme diameter constriction for suppressing intimal hyperplasia: A non-human primate study. J Vasc Surg 2009;49:1532-42.
European Search Report and search opinion dated Oct. 15, 2015, for EP Application No. 10828927.3.

* cited by examiner $$T_{I:M} = \frac{T_I}{T_M}$$

BIOERODIBLE WRAPS AND USES THEREFOR

CROSS REFERENCE TO RELATED APPLICATIONS

This application is a National Stage of International Patent Application No. PCT/US2010/054444, filed Oct. 28, 2010, which claims the benefit under 35 U.S.C. §119(e) of United States Provisional Patent Application No. 61/255,699, filed Oct. 28, 2009, each of which is herein incorporated by reference in its entirety.

STATEMENT REGARDING FEDERAL FUNDING

This invention was made with government support under Grant Nos. HL65745 and HL069368, awarded by the National Institutes of Health. The government has certain rights in the invention.

BACKGROUND

The present invention relates generally to tubular graft devices and methods of making such devices. In particular, the present invention provides tubular graft devices comprising a tubular member and a restrictive fiber matrix about a circumference of the tubular tissue.

Coronary artery disease, leading to myocardial infarction and ischemia, is currently the number one cause of morbidity and mortality worldwide. Current treatment alternatives consist of percutaneous transluminal angioplasty, stenting, and coronary artery bypass grafting (CABG). CABG can be carried out using either arterial or venous conduits and is the most effective and most widely used treatment to combat coronary arterial stenosis, with nearly 500,000 procedures being performed annually. In addition there are approximately 80,000 lower extremity bypass surgeries performed annually. The venous conduit used for bypass procedures is most frequently the autogenous saphenous vein and remains the graft of choice for 95% of surgeons performing these bypass procedures. According to the American Heart Association, in 2004 there were 427,000 bypass procedures performed in 249,000 patients. The long term outcome of these procedures is limited due to occlusion of the graft vessel or anastomotic site as a result of intimal hyperplasia (IH), which can occur over a timeframe of months to years.

Development of successful small diameter synthetic or tissue engineered vascular grafts has yet to be accomplished and use of arterial grafts (internal mammary, radial, or gastroepiploic arteries, for example) is limited by the short size, small diameter and availability of these vessels. Despite their wide use, failure of arterial vein grafts (AVGs) remains a major problem: 12% to 27% of AVGs become occluded in the first year with a subsequent annual occlusive rate of 2% to 4%. Patients with failed AVGs will die or require re-operation.

IH accounts for 20% to 40% of all AVG failures within the first 5 years. Several studies have determined that IH develops, to some extent, in all mature AVGs and this is regarded by many as an unavoidable response of the vein to grafting. IH is characterized by phenotypic modulation, followed by de-adhesion and migration of medial and adventitial smooth muscle cells (SMCs) and myofibroblasts into the intima where they proliferate. In many cases, this response can lead to stenosis and diminished blood flow through the graft. It is thought that IH may be initiated by the abrupt exposure of the veins to the dynamic mechanical environment of the arterial circulation.

Vein segments transposed to the arterial circulation for use as bypass grafts are exposed to increased blood flow and intraluminal pressure (Porter K E, Nydahl S, Dunlop P, Varty K, Thrush A J, and London N J. The development of an in vitro flow model of human saphenous vein graft intimal hyperplasia. Cardiovasc Res. 1996; 31(4): 607-14), and cyclic wall motion (including bending, twisting and stretching) due to their attachment to the beating heart in the case of CABGs (Vorp D A, Severyn D A, Steed D L, and Webster M W. A device for the application of cyclic twist and extension on perfused vascular segments. Am J. Physiol. 1996; 270(2 Pt 2): H787-95). Since veins are much thinner walled and more fragile than arteries, they experience significantly greater stresses in the arterial circuit than those to which they are accustomed in the venous circuit. Indeed, Liu and Fung showed that the average circumferential wall stress (CWS) in an AVG immediately upon reestablishing arterial flow could be 140-fold that in a vein under normal circumstances (Fuchs J C, Mitchener J S, and Hagen P O. Postoperative changes in autologous vein grafts. Ann Surg. 1978; 188(1): 1-15). This dramatic increase in CWS is due to the AVG being distended to its maximum diameter under arterial pressure. The tissue responds to this perceived injury by thickening, which is thought to be an attempt to return the stress to venous levels. However, this response is uncontrolled and can over-compensate, leading to stenosis instead of the desired thickening or "arterialization" of the vein segment.

It has been suggested that the hyperplastic response by AVGs is a direct result of a "cellular shock" that occurs as a result of their abrupt exposure to the arterial biomechanical environment (Angelini G D, et al. Distention promotes platelet and leukocyte adhesion and reduces short-term patency in pig arteriovenous bypass grafts. J Thorac Cardiovasc Surg. 1990; 99(3): 433-9; Campbell P A, et al. Vein grafts for arterial repair: Their success and reasons for failure. Ann R Coll Surg Engl. 1981; 63(4): 257-60; Campeau L L J, et al. Natural history of saphenous vein aortocoronary bypass grafts. Mod Concepts Cardiovasc Dis. 1984; 53: 59-63; Fuchs J C, Mitchener J S, and Hagen P O. Postoperative changes in autologous vein grafts. Ann Surg. 1978; 188(1): 1-15; Huynh T T, et al. Alterations in wall tension and shear stress modulate tyrosine kinase signaling and wall remodeling in experimental vein grafts. J Vasc Surg. 1999; 29(2): 334-44; Liu S Q et al. Changes in the organization of the smooth muscle cells in rat vein grafts. Ann Biomed Eng. 1998; 26(1): 86-95; Ramos J R, et al. Histologic fate and endothelial changes of distended and nondistended vein grafts. Ann Surg. 1976; 183(3): 205-28; Resnick N and Gimbrone M A. Hemodynamic forces are complex regulators of endothelial gene expression. The Faseb J. 1995; 9(10): 874-82; Sumpio B. Hemodynamic forces and vascular cell biology. Austin: R. G. Landes Company. 1993; Szilagyi D E, et al. Biologic fate of autogenous vein implants as arterial substitutes: Clinical, angiographic and histopathologic observations in femoropopliteal operations for atherosclerosis. Ann Surg. 1973; 178(3): 232-46; and Zwolak R M, et al. Kinetics of vein graft hyperplasia: Association with tangential stress. Journal of Vascular Surgery: Official Publication, the Society For Vascular Surgery [and] International Society For Cardiovascular Surgery, North American Chapter. 1987; 5(1): 126-36). Preventing acute distension of AVGs by adding an external structural support (or sheath) has seemingly improved the patency of vein grafts (Huynh T T, et al. J Vasc Surg. 1999; 29(2): 334-44; Cabrera Fischer E I, et al. Reduced elastic mismatch achieved by interposing vein cuff in expanded polytetrafluoroethylene femoral bypass decreases intimal hyperplasia. Artif Organs. 2005; 29(2): 122-30; Ducasse E, et al. Interposition vein cuff and intimal hyperplasia: An experimental study. Eur J Vasc Endovasc Surg. 2004; 27(6): 617-21; Huynh T T, et al. External support modulates g protein expression and receptor coupling in experimental vein grafts. Surgery. 1999; 126(2): 127-34; Jeremy J Y, et al. A bioabsorbable (polyglactin), nonrestrictive, external sheath inhibits porcine saphenous vein graft thickening. J Thorac Cardiovasc Surg. 2004; 127(6): 1766-72; Karayannacos P E, et al. Late failure in vein grafts: Mediating factors in subendothelial fibromuscular hyperplasia. Ann Surg. 1978; 187(2): 183-8; Kohler T R, et al. The effect of rigid external support on vein graft adaptation to the arterial circulation. J Vasc Surg. 1989; 9(2): 277-85; Liu S Q, et al. Partial prevention of monocyte and granulocyte activation in experimental vein grafts by using a biomechanical engineering approach. J. Biomech. 1999; 32(11): 1165-75; Liu S Q, et al. A possible role of initial cell death due to mechanical stretch in the regulation of subsequent cell proliferation in experimental vein grafts. Biomech Model Mechanobiol. 2002; 1(1): 17-27; Mehta D, et al. External stenting reduces long-term medial and neointimal thickening and platelet derived growth factor expression in a pig model of arteriovenous bypass grafting. Nat. Med. 1998; 4(2): 235-9; Parsonnet V, et al. New stent for support of veins in arterial grafts. Arch Surg. 1963; 87: 696-702; Vijayan V, et al. Long-term reduction of medial and intimal thickening in porcine saphenous vein grafts with a polyglactin biodegradable external sheath. J Vasc Surg. 2004; 40(5): 1011-9; and Vijayan V, et al. External supports and the prevention of neointima formation in vein grafts. Eur J Vasc Endovasc Surg. 2002; 24(1): 13-22). However, due to one or more fundamental limitations, these previous approaches have not resulted in a clinically viable means for improving AVG patency. All of these previous approaches utilized adventitially placed wraps/sheaths that were biodurable, and/or loose-fitting.

The Role of Biomechanics in the Development of Intimal Hyperplasia

IH is defined by an increase in the thickness of the inner layer of a blood vessel, typically as a result of an increased number and/or size of cells in the intima, followed by deposition of massive amounts of ECM by these cells. The cells contributing to this response are predominantly SMCs of medial and adventitial origin. IH occurs both physiologically during development as in the closure of the ductus arteriosus, and pathologically as a result of vascular injury. It is thought that AVG IH may be initiated by the abrupt exposure of the veins to the dynamic mechanical environment of the arterial circulation (Dobrin P B, Littooy F N, and Endean E D. Mechanical factors predisposing to intimal hyperplasia and medial thickening in autogenous vein grafts. Surgery. 1989; 105(3): 393-400). However, while increased levels of CWS has been shown to promote IH formation (Huynh T T, Davies M G, Trovato M J, Svendsen E, and Hagen P O. Alterations in wall tension and shear stress modulate tyrosine kinase signaling and wall remodeling in experimental vein grafts. J Vasc Surg. 1999; 29(2): 334-44 and Gusic R J, Myung R, Petko M, Gaynor J W, and Gooch K J. Shear stress and pressure modulate saphenous vein remodeling ex vivo. J. Biomech. 2005; 38(9): 1760-9), increased levels of shear stress tend to modulate it (Huynh T T, Davies M G, Trovato M J, Svendsen E, and Hagen P O. Alterations in wall tension and shear stress modulate tyrosine kinase signaling and wall remodeling in experimental vein grafts. J Vasc Surg. 1999; 29(2): 334-44; Gusic R J, Myung R, Petko M, Gaynor J W, and Gooch K J. Shear stress and pressure modulate saphenous vein remodeling ex vivo. J. Biomech. 2005; 38(9): 1760-9; Goldman J, Zhong L, and Liu S Q. Negative regulation of vascular smooth muscle cell migration by blood shear stress. Am J Physiol Heart Circ Physiol. 2006; Jiang Z, Berceli S A, Pfahnl C L, Wu L, Goldman D, Tao M, Kagayama M, Matsukawa A, and Ozaki C K. Wall shear modulation of cytokines in early vein grafts. J Vasc Surg. 2004; 40(2): 345-50; Jiang Z, Wu L, Miller B L, Goldman D R, Fernandez C M, Abouhamze Z S, Ozaki C K, and Berceli S A. A novel vein graft model: Adaptation to differential flow environments. American Journal of Physiology. Heart and Circulatory Physiology. 2004; 286 (1): H240-5; and Morinaga K, Okadome K, Kuroki M, Miyazaki T, Muto Y, and Inokuchi K. Effect of wall shear stress on intimal thickening of arterially transplanted autogenous veins in dogs. J Vasc Surg. 1985; 2(3): 430-3). These two biomechanical factors, seemingly causing opposing hyperplastic responses by AVGs, were carefully explored by Dobrin et al., who showed that the increased circumferential stretch plays a more significant role in promoting intimal thickening than the increased shear stress does in preventing it (Dobrin P B, Littooy F N, and Endean E D. Mechanical factors predisposing to intimal hyperplasia and medial thickening in autogenous vein grafts. Surgery. 1989; 105(3): 393-400). In another study that motivates this work, Zwolak et al. suggested a regulatory role for biomechanical wall stress in the arterialization of AVGs (Zwolak R M, Adams M C, and Clowes A W. Kinetics of vein graft hyperplasia: Association with tangential stress. Journal of Vascular Surgery: Official Publication, the Society For Vascular Surgery [and] International Society For Cardiovascular Surgery, North American Chapter. 1987; 5(1): 126-36). Jiang et al. demonstrated that increased wall shear stress, in the absence of an increase in wall tension, reduced the hyperplastic response in AVGs (Jiang Z, Wu L, Miller B L, Goldman D R, Fernandez C M, Abouhamze Z S, Ozaki C K, and Berceli S A. A novel vein graft model: Adaptation to differential flow environments. American Journal of Physiology. Heart and Circulatory Physiology. 2004; 286(1): H240-5). The in vivo work by Liu et al. has shown that by reducing the level of CWS in AVGs, via placement of a permanent polytetrafluoroethylene sheath, the hyperplastic response can be reduced (Cabrera Fischer E I, Bia Santana D, Cassanello G L, Zocalo Y, Crawford E V, Casas R F, and Armentano R L. Reduced elastic mismatch achieved by interposing vein cuff in expanded polytetrafluoroethylene femoral bypass decreases intimal hyperplasia. Artif Organs. 2005; 29(2): 122-30; Liu S Q, Moore M M, Glucksberg M R, Mockros L F, Grotberg J B, and Mok A P. Partial prevention of monocyte and granulocyte activation in experimental vein grafts by using a biomechanical engineering approach. J. Biomech. 1999; 32(11): 1165-75; and Liu S Q, Ruan Y Y, Tang D, Li Y C, Goldman J, and Thong L. A possible role of initial cell death due to mechanical stretch in the regulation of subsequent cell proliferation in experimental vein grafts. Biomech Model Mechanobiol. 2002; 1(1): 17-27). It is clear from these previous studies that the biomechanical environment of an AVG plays a significant role in the development of IH. In particular, the CWS appears to regulate the formation of IH, and controlling this was the focus of the approach described in this study.

Molecular and Cellular Processes Associated with Intimal Hyperplasia

Once injury is perceived by a vein, the hyperplastic response is set into motion and can be described by five distinct but interrelated cell processes: 1) Phenotypic modulation of adventitial and medial SMCs from a contractile and quiescent state with low proliferative potential to a synthetic state with high proliferative potential; 2) De-adhesion of SMCs or alteration of focal adhesions with other cells and the ECM; 3) Migration of SMCs from the outer layers through the basement membrane to the intima, which requires selective reassembling of focal adhesions that allow the cell to "walk" along the ECM; 4) Proliferation; and 5) Remodeling of the tissue, reflecting the changes in ECM composition caused by the synthetic SMCs secreting collagen, elastin, fibronectin, etc., as well as matrix degrading enzymes such as the various matrix metalloproteinases (MMPs). In order to inhibit the initiating events of AVG IH, it is probable that one must take into account each of these five processes. A schematic depicting the chain of events associated with IH is shown in FIG. 1.

Phenotypic Modulation

Modulation of SMC phenotype is a prominent feature in the pathogenesis of IH. Plaques abundant with modified SMCs have been found in the intima as early as the second week after grafting. Fully differentiated adult SMCs demonstrate low turnover as demonstrated by low proliferation and apoptosis rates. However, 48 hours after arterial injury, 15-40% of SMCs are mitotic. This abrupt shift in functionality is related to the fact that SMCs can exist in a spectrum of phenotypes, spanning from fully synthetic to fully contractile. Synthetic SMCs respond to regulatory signals and cytokines, and are capable of ECM turnover as well as growth factor production. On the other hand, contractile SMCs respond to vasomotor signals and control vessel tone. AVGs exhibit neointimal formation within the first two months by the migration and proliferation of synthetic SMCs and by subsequent, sustained ECM accumulation, including type I collagen production, in the prolonged presence of the de-differentiated type SMCs.

The phenotypic state of SMCs is regulated at least in part by mechanical forces, as demonstrated by the observation that cyclic stretch induces a substrate-dependent modulation of proliferation and h-caldesmon expression in vitro. In vivo studies have also shown the importance of mechanical injury on the phenotype of SMCs. Balloon inflation injury to the media was shown to promote ECM synthesis by SMCs as well as to decrease alpha actin content. Several reports have shown that neointimal SMCs of veins transposed to the arterial circulation are phenotypically altered, supporting the notion that the change from the venous to the arterial environment triggers phenotypic alteration. Further evidence comes from ex vivo organ culture studies where, for example, cyclic stretch was found to be necessary to maintain the contractile function of SMCs in cultured rat portal veins. Goldman et al. exposed rat vena cava to arterial pressures (Goldman J, Zhong L, and Liu S Q. Degradation of alpha-actin filaments in venous smooth muscle cells in response to mechanical stretch. American Journal of Physiology. Heart and Circulatory Physiology. 2003; 284(5): H1839-47), which led to a large increase in medial circumferential strain and a concomitant reduction in the SMC filamentous actin coverage. Clearly, the changes in the mechanical environment related to vein grafting can lead to phenotypic alterations of the mural SMCs, possibly contributing to the development of IH.

Indicators of a synthetic phenotype include the presence of increased quantities of Golgi complex and rough endoplasmic reticulum, and decreased quantities of filamentous actin. A contractile phenotype is demonstrated by the presence of an intact contractile apparatus indicated by the expression of contractile proteins such as smoothelin, h-caldesmon, smooth muscle myosin heavy chain, and large quantities of filamentous actin.

De-Adhesion and Migration

Cellular de-adhesion is one of the earliest responses in the IH cascade. This process refers to an alteration in a cell's adhesion to the ECM from a state of strong adherence, with focal adhesions and stress fibers, to a state of weaker adherence, characterized by a restructuring of focal adhesions and stress fibers while maintaining a spread cell shape. SMC de-adhesion will of course allow SMC migration and proliferation which will contribute to neointima formation.

While there are many important proteins involved in the regulation of cellular adhesion, we focused our attention on matricellular proteins, which function as adaptors and modulators of cell matrix interactions (Bornstein P. Diversity of function is inherent in matricellular proteins: An appraisal of thrombospondin 1. J. Cell Biol. 1995; 130(3): 503-6 and Sage E H and Bornstein P. Extracellular proteins that modulate cell-matrix interactions. Sparc, tenascin, and thrombospondin. The Journal of Biological Chemistry. 1991; 266(23): 14831-4), and intracellular adhesion proteins, which have been shown to localize to cellular focal adhesion sites (Nikolopoulos S N and Turner C E. Integrin-linked kinase (ilk) binding to paxillin 1d1 motif regulates ilk localization to focal adhesions. The Journal of Biological Chemistry. 2001; 276(26): 23499-505 and Tu Y, Wu S, Shi X, Chen K, and Wu C. Migfilin and mig-2 link focal adhesions to filamin and the actin cytoskeleton and function in cell shape modulation. Cell. 2003; 113: 37-47). Tenascin C (TN-C), thrombospondin 1,2 (TSP), and secreted protein acidic and rich in cysteine (SPARC) are matricellular proteins that exhibit highly regulated expression during development and cellular injury (Murphy_Ullrich J E. The de-adhesive activity of matricellular proteins: Is intermediate cell adhesion an adaptive state? J Clin Invest. 2001; 107(7): 785-90). Mitogen inducible gene 2 (Mig-2) and integrin linked kinase (ILK) are intracellular proteins involved in cellular shape modulation (Nikolopoulos S N and Turner C E. Integrin-linked kinase (ILK) binding to paxillin 1d1 motif regulates ilk localization to focal adhesions. The Journal of Biological Chemistry. 2001; 276(26): 23499-505 and Tu Y, Wu S, Shi X, Chen K, and Wu C. Migfilin and Mig-2 link focal adhesions to filamin and the actin cytoskeleton and function in cell shape modulation. Cell. 2003; 113: 37-47) and integrin mediated signal transduction (Wu C and Dedhar S. Integrin-linked kinase (ILK) and its interactors: A new paradigm for the coupling of extracellular matrix to actin cytoskeleton and signaling complexes. J. Cell Biol. 2001; 155(4): 505-10), respectively. The actions of TN-C, TSP, and SPARC on the cytoskeleton and focal adhesions are basically indistinguishable (Greenwood J A, Theibert A B, Prestwich G D, and Murphy_Ullrich J E. Restructuring of focal adhesion plaques by pi 3-kinase. Regulation by ptdins (3,4,5)-p(3) binding to alpha-actinin. J. Cell Biol. 2000; 150(3): 627-42 and Murphy-Ullrich J E, Lightner V A, Aukhil I, Yan Y Z, Erickson H P, and Hook M. Focal adhesion integrity is downregulated by the alternatively spliced domain of human tenascin. J. Cell Biol. 1991; 115(4): 1127-36). However, these three proteins each have unique receptors and have similar but separate signaling pathways to produce a state of intermediate adhesion, which is a precursor to cell migration (Murphy-Ullrich J E. The de-adhesive activity of matricellular proteins: Is intermediate cell adhesion an adaptive state? J Clin Invest. 2001; 107(7): 785-90). Mig-2 and ILK have also been implicated in cellular adhesion (Nikolopoulos S N and Turner C E. Integrin-linked kinase (ILK) binding to paxillin 1d1 motif regulates ilk localization to focal adhesions. The Journal of Biological Chemistry. 2001; 276(26): 23499-505 and Tu Y, Wu S, Shi X, Chen K, and Wu C. Migfilin and Mig-2 link focal adhesions to filamin and the actin cytoskeleton and function in cell shape modulation. Cell. 2003; 113: 37-47). Specifically, Mig-2 has been shown to participate in the connection between cell matrix adhesions and the actin cytoskeleton as well as to modulate cell shape (Tu Y, Wu S, Shi X, Chen K, and Wu C. Migfilin and mig-2 link focal adhesions to filamin and the actin cytoskeleton and function in cell shape modulation. Cell. 2003; 113: 37-47). Recent studies have indicated that ILK serves as a mediator in integrin mediated signal transduction (Wu C. Integrin-linked kinase and pinch: Partners in regulation of cell-extracellular matrix interaction and signal transduction. Journal of Cell Science. 1999; 112 (Pt 24): 4485-9). Furthermore, both Mig-2 and ILK are required for maintaining focal adhesions (Nikolopoulos S N and Turner C E. Integrin-linked kinase (ilk) binding to paxillin 1d1 motif regulates ilk localization to focal adhesions. The Journal of Biological Chemistry. 2001; 276(26): 23499-505 and Tu Y, Wu S, Shi X, Chen K, and Wu C. Migfilin and mig-2 link focal adhesions to filamin and the actin cytoskeleton and function in cell shape modulation. Cell. 2003; 113: 37-47). By examining the changes in the levels of TN-C, TSP, SPARC, Mig-2, and ILK, we believe that we will be able to make conclusions about the state of adhesion of SMCs within the vein segments. A schematic showing the intracellular localization of TN-C, TSP, SPARC, Mig-2 and ILK is shown in FIG. 2.

A prerequisite for SMC migration in vivo is degradation of surrounding matrix proteins. Matrix metalloproteinases (specifically, MMP-1, MMP-2, and MMP-9) can selectively degrade various components of the vascular ECM (Galis Z S, Muszynski M, Sukhova G K, Simon_Morrissey E, Unemori E N, Lark M W, Amento E, and Libby P. Cytokine-stimulated human vascular smooth muscle cells synthesize a complement of enzymes required for extracellular matrix digestion. Circulation Research (Online) 1994; 75(1): 181-9; Newby A C, Southgate K M, and Davies M G. Extracellular matrix degrading metalloproteinases in the pathogensis of arteriosclerosis. Basic Res Cardiol. 1994; 89(Suppl 1): 59-70; Porter K E, Naik J, Turner N A, Dickison T, Thompson M M, and London J M. Simvastatin inhibits human saphenous vein neointima formation via inhibition of smooth muscle cell proliferation and migration. J. Vasc. Surg. 2002; 36: 150-7; and Southgate K M, Davies M, Booth R F, and Newby A C. Involvement of extracellular-matrix-degrading metalloproteinases in rabbit aortic smooth-muscle cell proliferation. Biochem J. 1992; 288 (Pt 1): 93-9). MMPs have been shown to be critical for the development of arterial lesions by regulating SMC migration. The balance between MMPs, their activator (MT-1 MMP) (Lafleur M A, Hollenberg M D, Atkinson S J, Knauper V, Murphy G, and Edwards D R. Activation of pro-(matrix metalloproteinase-2) (pro-mmp-2) by thrombin is membrane-type-mmp-dependent in human umbilical vein endothelial cells and generates a distinct 63 kda active species. Biochem J. 2001; 357(Pt 1): 107-15), and their inhibitors (specifically, TIMP-1, TIMP-2, TIMP-3, and TIMP-4) determines the level of ECM degradation (Meng X, Mavromatis K, and Galis Z S. Mechanical stretching of human saphenous vein grafts induces expression and activation of matrix-degrading enzymes associated with vascular tissue injury and repair. Exp Mol. Pathol. 1999; 66(3): 227-37). Numerous studies have shown that MMPs and TIMPs play a significant role in the early stages of IH in response to altered hemodynamics and vascular injury (George S J, Baker A H, Angelini G D, and Newby A C. Gene transfer of tissue inhibitor of metalloproteinase-2 inhibits metalloproteinase activity and neointima formation in human saphenous veins. Gene Ther. 1998; 5(11): 1552-60; George S J, Johnson J L, Angelini G D, Newby A C, and Baker A H. Adenovirus-mediated gene transfer of the human TIMP-1 gene inhibits smooth muscle cell migration and neointimal formation in human saphenous vein. Hum Gene Ther. 1998; 9(6): 867-77; and Lijnen H R, Soloway P, and Collen D. Tissue inhibitor of matrix metalloproteinases-1 impairs arterial neointima formation after vascular injury in mice. Circ Res. 1999; 85(12): 1186-91). For example, after 6 hours of ex vivo perfusion with arterial hemodynamics, expression of MMP-2 and MMP-9 was increased in human saphenous veins (Mavromatis K, Fukai T, Tate M, Chesler N, Ku D N, and Galis Z S. Early effects of arterial hemodynamic conditions on human saphenous veins perfused ex vivo. Arterioscler Thromb Vasc Biol. 2000; 20(8): 1889-95). Other organ culture studies of human saphenous vein have shown increased production of MMP-9 and increased activation of MMP-2 (Porter K E, Thompson M M, Loftus 1M, McDermott E, Jones L, Crowther M, Bell P R, and London N J. Production and inhibition of the gelatinolytic matrix metalloproteinases in a human model of vein graft stenosis. Eur J Vasc Endovasc Surg. 1999; 17(5): 404-12; Porter K E, Naik J, Turner N A, Dickison T, Thompson M M, and London J M. Simvastatin inhibits human saphenous vein neointima formation via inhibition of smooth muscle cell proliferation and migration. J. Vasc. Surg. 2002; 36: 150-7; and George S J, Zaltsman A B, and Newby A C. Surgical preparative injury and neointima formation increase MMP-9 expression and MMP-2 activation in human saphenous vein. Cardiovasc Res. 1997; 33(2): 447-59) under arterial conditions. Broad spectrum MMP inhibitors such as simvastatin have been shown to inhibit neointima formation in this model (Porter K E, Naik J, Turner N A, Dickison T, Thompson M M, and London J M. Simvastatin inhibits human saphenous vein neointima formation via inhibition of smooth muscle cell proliferation and migration. J. Vasc. Surg. 2002; 36: 150-7 and Porter K E, Loftus I M, Peterson M, Bell P R, London N J, and Thompson M M. Marimastat inhibits neointimal thickening in a model of human vein graft stenosis. Br J. Surg. 1998; 85(10): 1373-7).

Mechanical forces can influence SMC de-adhesion and migration by directly regulating the above factors. For example, MMP-1 expression is increased in venous SMCs exposed to pulse pressure compared to static controls (Redmond E M, Cahill P A, Hirsch M, Wang Y N, Sitzmann J V, and Okada S S. Effect of pulse pressure on vascular smooth muscle cell migration: The role of urokinase and matrix metalloproteinase. Thrombosis & Haemostasis. 1999; 81(2): 293-300), while MMP-2 mRNA levels are increased in mouse SMCs exposed to cyclic stretch (Grote K, Flach I, Luchtefeld M, Akin E, Holland S M, Drexler H, and Schieffer B. Mechanical stretch enhances mRNA expression and proenzyme release of matrix metalloproteinase-2 (MMP-2) via nad(p)h oxidase-derived reactive oxygen species. Circulation Research. 2003; 92(11): 80-6). In cultured SMCs from human saphenous vein, MMP-2 and MMP-9 transcript and protein levels increased when exposed to uniaxial stationary strain, but decreased when exposed to uniaxial cyclic strain (Asanuma K, Magid R, Johnson C, Nerem R M, and Galis Z S. Uniaxial strain upregulates matrix-degrading enzymes produced by human vascular smooth muscle cells. Am J Physiol Heart Circ Physiol. 2003; 284(5): H1778-84). Cyclic strain of fibroblasts has been shown to increase MT-1 MMP levels (Tyagi S C, Lewis K, Pikes D, Marcello A, Mujumdar V S, Smiley L M, and Moore C K. Stretch-induced membrane type matrix metalloproteinase and tissue plasminogen activator in cardiac fibroblast cells. J Cell Physiol. 1998; 176(2): 374-82)[166] and decrease TIMP-1 levels (Yamaoka A, Matsuo T, Shiraga F, and Ohtsuki H. Timp-1 production by human scleral fibroblast decreases in response to cyclic mechanical stretching. Opthalmic Research. 2001; 33(2): 98-101). In addition, SMC migration was shown to be regulated by shear stress induced EC signaling (Bassiouny H S, Song R H, Kocharyan H, Kins E, and Glagov S. Low flow enhances platelet activation after acute experimental arterial injury. Journal of Vascular Surgery. 1998; 27(5): 910-8; Nakazawa T, Yasuhara H, Shigematsu K, and Shigematsu H. Smooth muscle cell migration induced by shear-loaded platelets and endothelial cells. Enhanced platelet-derived growth factor production by shear-loaded platelets. Int Angiol. 2000; 19(2): 142-6; Powell R J, Carruth J A, Basson M D, Bloodgood R, and Sumpio B E. Matrix-specific effect of endothelial control of smooth muscle cell migration. Journal of Vascular Surgery. 1996; 24(1): 51-7; and Shigematsu K, Yasuhara H, Shigematsu H, and Muto T. Direct and indirect effects of pulsatile shear stress on the smooth muscle cell. Int Angiol. 2000; 19(1): 39-46). Mechanical forces can influence SMC de-adhesion and migration by directly regulating the above factors. SMC migration was shown to be regulated by shear stress induced EC signaling (Garanich J S, Pahakis M, and Tarbell J M. Shear stress inhibits smooth muscle cell migration via nitric oxide-mediated downregulation of matrix metalloproteinase-2 activity. Am J Physiol Heart Circ Physiol. 2005; 288(5): H2244-52; Bassiouny H S, Song R H, Kocharyan H, Kins E, and Glagov S. Low flow enhances platelet activation after acute experimental arterial injury. Journal of Vascular Surgery. 1998; 27(5): 910-8; Nakazawa T, Yasuhara H, Shigematsu K, and Shigematsu H. Smooth muscle cell migration induced by shear-loaded platelets and endothelial cells. Enhanced platelet-derived growth factor production by shear-loaded platelets. Int Angiol. 2000; 19(2): 142-6; Powell R J, Carruth J A, Basson M D, Bloodgood R, and Sumpio B E. Matrix-specific effect of endothelial control of smooth muscle cell migration. Journal of Vascular Surgery. 1996; 24(1): 51-7; Shigematsu K, Yasuhara H, Shigematsu H, and Muto T. Direct and indirect effects of pulsatile shear stress on the smooth muscle cell. Int Angiol. 2000; 19(1): 39-46; and Sho M, Sho E, Singh T M, Komatsu M, Sugita A, Xu C, Nanjo H, Zarins C K, and Masuda H. Subnormal shear stress-induced intimal thickening requires medial smooth muscle cell proliferation and migration. Exp Mol. Pathol. 2002; 72(2): 150-60).

Proliferation

Several growth factors have been implicated as key components in the hyperplastic response of vein grafts. Transforming growth factor beta (TGF-β) appears to be of particular importance. For example, Wolf et al. demonstrated that systemic administration of antibodies against TGF-β significantly reduced the development of IH in a rat model (Wolf Y G, Rasmussen L M, and Ruoslahti E. Antibodies against transforming growth factor-beta 1 suppress intimal hyperplasia in a rat model. J Clin Invest. 1994; 93(3): 1172-8). Platelet derived growth factor (PDGF) and basic fibroblast growth factor (bFGF) also appear to be primary factors involved in IH associated SMC proliferation. For example, PDGF causes a dose dependent proliferation response in cultured SMCs (Uzui H, Lee J D, Shimizu H, Tsutani H, and Ueda T. The role of protein-tyrosine phosphorylation and gelatinase production in the migration and proliferation of smooth muscle cells. Atherosclerosis. 2000; 149(1): 51-9), while TGF-β inhibits proliferation (Mii S, Ware J A, and Kent K C. Transforming growth factor-beta inhibits human vascular smooth muscle cell growth and migration. Surgery. 1993; 114(2): 464-70). bFGF released from dead and damaged cells of autologous vein grafts promotes SMC proliferation (Qian H, Zhang B, and Zhao H. [gene expression of bfgf and intimal hyperplasia of autologous vein grafts in rats]. Zhonghua Yi Xue Za Zhi. 1996; 76(11): 826-8). mRNA levels of PDGF transcripts as well as numbers of proliferating cells were found to be highest in the neointima of porcine vein grafts (Francis S E, Hunter S, Holt C M, Gadsdon P A, Rogers S, Duff G W, Newby A C, and Angelini G D. Release of platelet-derived growth factor activity from pig venous arterial grafts. J Thorac Cardiovasc Surg. 1994; 108(3): 540-8). While growth factors clearly play a role in IH, MMPs have also been shown to be critical for the development of arterial lesions by regulating SMC proliferation (Southgate K M, Davies M, Booth R F, and Newby A C. Involvement of extracellular-matrix-degrading metalloproteinases in rabbit aortic smooth-muscle cell proliferation. Biochem J. 1992; 288 (Pt 1): 93-9; Cho A and Reidy M A. Matrix metalloproteinase-9 is necessary for the regulation of smooth muscle cell replication and migration after arterial injury. Circ Res. 2002; 91(9): 845-51), while TIMPs have been shown to promote apoptosis of SMC (Annabi B, Shedid D, Ghosn P, Kenigsberg R L, Desrosiers R R, Bojanowski M W, Beaulieu E, Nassif E, Moumdjian R, and Beliveau R. Differential regulation of matrix metalloproteinase activities in abdominal aortic aneurysms. J Vasc Surg. 2002; 35(3): 539-46).

IH has been shown to be associated with increases in SMC proliferation and both increases and decreases in apoptosis. It may seem counter-intuitive that an increase in intimal apoptosis is associated with IH, a condition associated with increased cell numbers. However, it must be kept in mind that increases in cell number is but a singular event in the balance that regulates IH. That is, though there may be an absolute increase in apoptosis, a greater increase in cell proliferation would result in a net increase in cell number. For these reasons, it is important to evaluate both sides of the balance (i.e., both promoting and inhibiting factors) when assessing proliferation.

Proliferating cell nuclear antigen (PCNA) and terminal deoxynucleotidyl transferase-mediated dUTP-biotin in situ nick end labeling (TUNEL) have been used to label proliferating and apoptotic cells, respectively, within intact AVGs, both in vivo (Nishibe T, Miyazaki K, Kudo F, Flores J, Nagato M, Kumada T, and Yasuda K. Induction of angiotensin converting enzyme in neointima after intravascular stent placement. Int Angiol. 2002; 21(3): 250-5), and in vitro (Zuckerbraun B S, McCloskey C A, Mahidhara R S, Kim P K, Taylor B S, and Tzeng E. Overexpression of mutated ikappabalpha inhibits vascular smooth muscle cell proliferation and intimal hyperplasia formation. J Vasc Surg. 2003; 38(4): 812-9). Cell proliferation and apoptosis are simultaneous processes that occur within the adventitia and media of the vein during the first week following grafting, however this balance is thereafter disrupted with proliferation rates increasing over rates of apoptosis (Nishibe T, Miyazaki K, Kudo F, Flores J, Nagato M, Kumada T, and Yasuda K. Induction of angiotensin converting enzyme in neointima after intravascular stent placement. Int Angiol. 2002; 21(3): 250-5). The level of proliferation within the media and neointima of stenosed aortocoronary bypass grafts excised upon re-operation has been shown to be significantly higher than non-stenosed controls (Hilker M, Buerke M, Lehr H A, Oelert H, and Hake U. Bypass graft disease: Analysis of proliferative activity in human aortocoronary bypass grafts. 2002; 5 Suppl 4: S331-41).

Increased wall stress has been associated with AVG IH, and this may be a direct result of a mechanical regulation of SMC proliferation, and apoptosis. For example, venous SMCs have been shown to increase their proliferation compared to arterial SMCs when exposed to arterial levels of cyclic stretch (Predel H G, Yang Z, von_Segesser L, Turina M, Buhler F R, and Luscher T F. Implications of pulsatile stretch on growth of saphenous vein and mammary artery smooth muscle. Lancet. 1992; 340(8824): 878-9 and Dethlefsen S M, Shepro D, and D'Amore P A. Comparison of the effects of mechanical stimulation on venous and arterial smooth muscle cells in vitro. J Vasc Res. 1996; 33(5): 405-13). Liu et al. showed via bromodeoxyuridine staining and TUNEL analysis that mechanical stretch due to arterial hemodynamics induces cell death, which possibly mediates subsequent cell proliferation in a rat AVG model (Liu B, Itoh H, Louie O, Kubota K, and Kent K C. The signaling protein rho is necessary for vascular smooth muscle migration and survival but not for proliferation. Surgery. 2002; 132(2): 317-25). Predel et al. showed that pulsatile stretch stimulates SMC proliferation in saphenous veins, but not internal mammary arteries, and may contribute to venous bypass graft disease (Predel H G, Yang Z, von_Segesser L, Turina M, Buhler F R, and Luscher T F. Implications of pulsatile stretch on growth of saphenous vein and mammary artery smooth muscle. Lancet. 1992; 340(8824): 878-9). When veins are transposed to the arterial circulation they undergo an increase of luminal shear stress in addition to intramural stress. Indeed it has been shown that a combination of increased shear stress and cyclic stretch imposed on cultured SMCs activates PDGF receptor alpha (Hu Y, Bock G, Wick G, and Xu Q. Activation of pdgf receptor alpha in vascular smooth muscle cells by mechanical stress. Faseb J. 1998; 12(12): 1135-42)[192].

Remodeling

Vascular remodeling typically refers to a change in the morphology or microstructure of a blood vessel in response to changes in the biomechanical environment. It is believed that this occurs as an attempt by the tissue to restore biomechanical homeostasis (i.e., to return to normal levels of shear and wall stress). In the case of AVGs, IH is a pathological form of remodeling that includes increased intimal thickness caused by SMC migration and proliferation, increased intimal apoptosis, sclerosis of the intima and media due to increased ECM deposition, and hypertrophy of the medial and adventitial SMCs.

Vascular cells produce the ECM components such as collagen and elastin. The phenotypic modulation of SMCs associated with vein grafting has been shown to alter ECM synthesis characterized by increasing collagen type I and elastin production. Veins used as arterial bypass grafts undergo an alteration of their ECM components, which can result in a loss of lumenal area and eventual occlusion. An alteration in matrix synthesis directly leads to increased collagen content in the hyperplastic neointima during the first week after injury resulting from balloon angioplasty. In addition, AVGs that undergo this hyperplastic remodeling exhibit decreased compliance as compared to fresh veins, which can contribute to their failure.

SUMMARY

Developing a reliable means to prevent the early events of the IH process would contribute to improvements in the outcome of arterial bypass procedures. Therefore, provided herein is a method of mechanically conditioning an arterial vein graft, or any tubular tissue (living cellular structure), typically, but not exclusively, in autologous, allogeneic xenogeneic transplantation procedures. To this end, provided herein is a method of wrapping a tubular tissue, including, without limitation, a vein, artery, urethra, intestine, esophagus, trachea, bronchi, ureter and fallopian tube. The tubular tissue is wrapped with a restrictive fiber matrix of a bioerodible (also referred to as biodegradable or bioresorbable) polymer about a circumference of the tubular tissue. In one non-limiting embodiment, the matrix is deposited onto tubular tissue by electrospinning. In one particular non-limiting embodiment, the tubular tissue is a vein, such as a saphenous vein, that is used, for instance, in an arterial bypass procedure, such as a coronary arterial bypass procedure.

The biodegradation rate of the polymer matrix may be manipulated, optimized or otherwise adjusted so that the matrix degrades over a useful time period. For instance, in the case of a coronary artery bypass, it is desirable that the matrix dissolves over 12 hours or more so as to prevent substantial sudden stress on the graft. The polymer degrades over a desired period of time so that the mechanical support offered by the polymer matrix is gradually reduced over that period and the vein would be exposed to gradually increasing levels of CWS. In a typical application, the matrix biodegrades over a period of two weeks to two years. In a preferred embodiment, the matrix biodegrades over a period of two months to one year. In a more preferred embodiment, the matrix biodegrates over a period of two to six months. The matrix can be configured such that the biodegradation rate is linear or non-linear.

This new approach would have two potential applications. In the first non-limiting application, the matrix can be used as a peri-surgical tool for the modification of vein segments intended for use as an AVG. The modification of the vein or other tubular anatomical structure would be performed by treating the vein at bedside, immediately after removal from the body and just prior to grafting, for example and without limitation, the arterial bypass surgery. In one non-limiting example, after the saphenous vein is harvested, and while the surgeon is exposing the surgical site, the polymer wrap would be electrospun onto the vein just prior to it being used for the bypass procedure.

In a second non-limiting embodiment, the polymer matrix can be used as a new vehicle for the delivery of support to AVGs. While modification of the mechanical environment of a vein graft over time could itself improve AVG patency, delivery of active agents and biological (cellular) support to AVGs may prove desirable in many instances. By tuning an electrospun polymer wrap, in which active agents and/or biologicals are incorporated, to degrade at a desired rate, the rate of delivery of these support modalities could be controlled.

According to one embodiment a tubular tissue graft device is provided. The device comprises a tubular tissue and a restrictive fiber matrix of a bioerodible polymer about a circumference of the tubular tissue. The matrix is typically contiguous or essentially contiguous about a circumference of at least a portion (part) of the tubular tissue. In one embodiment, the tubular tissue is obtained from a vein (is venous), for example and without limitation, the venous tubular tissue is obtained from a portion of a saphenous vein. In other embodiments, the tubular tissue is chosen from (obtained from an organ/tissue chosen from) one or more of an artery, urethra, intestine, esophagus, ureter, trachea, bronchi, and fallopian tube. The matrix of the device typically bioerodes in situ (when implanted) over a time period ranging from 12 hours to two weeks, meaning the supportive nature of the matrix is degraded over that time period, not necessarily that the matrix completely erodes.

In one embodiment, the device is prepared by electrospinning the polymer fibers onto the tubular tissue. The polymer fibers can comprise any useful bioerodible polymer composition. In one embodiment, shown below, the fibers comprise a polymer comprising ester and urethane linkages, including for example and without limitation a poly(ester urethane)urea. In other embodiments, the fibers comprise a polymer chosen from one or more of: a polymer derived from an alpha-hydroxy acid, a polylactide, a poly(lactide-co-glycolide), a poly(L-lactide-co-caprolactone), a polyglycolic acid, a poly(dl-lactide-co-glycolide), a poly(1-lactide-co-dl-lactide), a polymer comprising a lactone monomer, a polycaprolactone, polymer comprising carbonate linkages, a polycarbonate, polyglyconate, poly(glycolide-co-trimethylene carbonate), a poly(glycolide-co-trimethylene carbonate-co-dioxanone), a polymer comprising urethane linkages, a polyurethane, a poly(ester urethane) urea, a poly(ester urethane) urea elastomer, a polymer comprising ester linkages, a polyalkanoate, a polyhydroxybutyrate, a polyhydroxyvalerate, a polydioxanone, a polygalactin, a natural polymer, chitosan, collagen, elastin, alginate, cellulose, hyaluronic acid and gelatin. In one embodiment, the polymer composition comprises a poly(ester urethane)urea with from about 25% wt. to about 75% wt. collagen. This polymer also may comprise elastin, for example and without limitation from about 25% wt. to about 75% wt. of a mixture of collagen and elastin, which are, according to one embodiment, in approximately (about) equal amounts.

In yet another embodiment, one or both of a cell and a therapeutic agent (e.g., drug, cytokine, chemoattractant, antibiotic, anti-inflammatory, etc.) is associated with (attached to, absorbed into, adsorbed to, grown into, linked to, etc.) the matrix. In one embodiment, cells are associated with the matrix, for example and without limitation, one or more of cells chosen from stem cells, progenitor (precursor) cells, smooth muscle cells, skeletal myoblasts, myocardial cells, endothelial cells, endothelial progenitor cells, bone-marrow derived mesenchymal cells and genetically modified cells are associated with the matrix. In another embodiment, a growth factor is associated with the matrix, for example and without limitation, a growth factor chosen from one or more of basic fibroblast growth factor (bFGF), acidic fibroblast growth factor (aFGF), vascular endothelial growth factor (VEGF), hepatocyte growth factor (HGF), insulin-like growth factors (IGF), transforming growth factor-beta pleiotrophin protein, midkine protein and IGF-1. In another embodiment, a drug is associated with the matrix. In certain non-limiting embodiments, the drug is chosen from one or more of a non-steroidal anti-inflammatory drug, an antibiotic, an anticlotting factor, an immunosuppressant, a glucocorticoid, a drug acting on an immunophilin, an interferon, a TNF binding proteins, a taxane, a statin, and a nitric oxide donor. In others, the drug is chosen from one or more of an NSAID, salicylic acid, indomethacin, sodium indomethacin trihydrate, salicylamide, naproxen, colchicine, fenoprofen, sulindac, diflunisal, diclofenac, indoprofen sodium salicylamide, antiinflammatory cytokines, antiinflammatory proteins, steroidal anti-inflammatory agents, heparin, Pebac, enoxaprin, aspirin, hirudin, plavix, bivalirudin, prasugrel, idraparinux, warfarin, coumadin, clopidogrel, PPACK, GGACK, tissue plasminogen activator, urokinase, streptokinase, a glucocorticoid, hydrocortisone, betamethasone, dexamethasone, flumethasone, isoflupredone, methylprednisolone, prednisone, prednisolone, triamcinolone acetonide, an antiangiogenic, fluorouracil, paclitaxel, doxorubicin, cisplatin, methotrexate, cyclophosphamide, etoposide, pegaptanib, lucentis, tryptophanyl-tRNA synthetase, retaane, CA4P, AdPEDF, VEGF-TRAP-EYE, AG-103958, Avastin, JSM6427, TG100801, ATG3, OT-551, endostatin, thalidomide, becacizumab, neovastat, an antiproliferative, sirolimus, paclitaxel, perillyl alcohol, farnesyl transferase inhibitors, FPTIII, L744, antiproliferative factor, Van 10/4, doxorubicin, 5-FU, Daunomycin, Mitomycin, dexamethasone, azathioprine, chlorambucil, cyclophosphamide, methotrexate, mofetil, vasoactive intestinal polypeptide, an antibody, a drug acting on immunophilins, cyclosporine, zotarolimus, everolimus, tacrolimus, sirolimus, an interferon, a TNF binding protein, a taxane, paclitaxel, docetaxel, a statin, atorvastatin, lovastatin, simvastatin, pravastatin, fluvastatin, rosuvastatin a nitric oxide donor or precursor, Angeli's Salt, L-Arginine, Free Base, Diethylamine NONOate, Diethylamine NONOate/AM, Glyco-SNAP-1, Glyco-SNAP-2, (±)-S-Nitroso-N-acetylpenicillamine, S-Nitrosoglutathione, NOC-5, NOC-7, NOC-9, NOC-12, NOC-18, NOR-1, NOR-3, SIN-1, Hydrochloride, Sodium Nitroprusside, Dihydrate, Spermine NONOate, Streptozotocin, an antibiotic, acyclovir, afloxacin, ampicillin, amphotericin B, atovaquone, azithromycin, ciprofloxacin, clarithromycin, clindamycin, clofazimine, dapsone, diclazaril, doxycycline, erythromycin, ethambutol, fluconazole, fluoroquinolones, foscarnet, ganciclovir, gentamicin, iatroconazole, isoniazid, ketoconazole, levofloxacin, lincomycin, miconazole, neomycin, norfloxacin, ofloxacin, paromomycin, penicillin, pentamidine, polymixin B, pyrazinamide, pyrimethamine, rifabutin, rifampin, sparfloxacin, streptomycin, sulfadiazine, tetracycline, tobramycin, trifluorouridine, trimethoprim sulphate, Zn-pyrithione, and silver salts such as chloride, bromide, iodide and periodate.

Also provided herein is a method of preparing a tubular graft comprising depositing a fiber matrix of a bioerodible polymer about a perimeter (outside surface, circumference) of a tubular tissue to produce a tubular tissue graft device. The matrix is typically contiguous or essentially contiguous about a circumference of at least a portion (part) of the tubular tissue. In one embodiment, the matrix is deposited by electrospinning. As above, the matrix typically bioerodes in situ over a time period ranging from 12 hours to two weeks.

In one embodiment, the tubular tissue is obtained from a vein, for example and without limitation, the venous tubular tissue is obtained from a portion of a saphenous vein. In other embodiments, the tubular tissue is chosen from (obtained from an organ/tissue chosen from) one or more of an artery, urethra, intestine, esophagus, ureter, trachea, bronchi, and fallopian tube.

The polymer fibers can comprise any useful bioerodible and biocompatible polymer composition. In one embodiment, shown below, the fibers comprise a polymer comprising ester and urethane linkages, including for example and without limitation a poly(ester urethane)urea. In other embodiments, the fibers comprise a polymer chosen from one or more of: a polymer derived from an alpha-hydroxy acid, a polylactide, a poly(lactide-co-glycolide), a poly(L-lactide-co-caprolactone), a polyglycolic acid, a poly(dl-lactide-co-glycolide), a poly(1-lactide-co-dl-lactide), a polymer comprising a lactone monomer, a polycaprolactone, polymer comprising carbonate linkages, a polycarbonate, polyglyconate, poly(glycolide-co-trimethylene carbonate), a poly(glycolide-co-trimethylene carbonate-co-dioxanone), a polymer comprising urethane linkages, a polyurethane, a poly(ester urethane) urea, a poly(ester urethane) urea elastomer, a polymer comprising ester linkages, a polyalkanoate, a polyhydroxybutyrate, a polyhydroxyvalerate, a polydioxanone, a polygalactia, a natural polymer, chitosan, collagen, elastin, alginate, cellulose, hyaluronic acid and gelatin. In one embodiment, the polymer composition comprises a poly(ester urethane)urea with from about 25% wt. to about 75% wt. collagen, including increments therebetween. This polymer also may comprise elastin, for example and without limitation from about 25% wt. to about 75% wt. of a mixture of collagen and elastin, which are, according to one embodiment, in approximately (about) equal amounts.

In another embodiment, the method comprises associating one or both of a cell and a therapeutic agent (e.g., drug, cytokine, chemoattractant, antibiotic, anti-inflammatory, etc.) is associated with (attached to, absorbed into, adsorbed to, grown into, linked to, etc.) the matrix. In one embodiment, cells are associated with the matrix, for example and without limitation, one or more of cells chosen from stem cells, progenitor (precursor) cells, smooth muscle cells, skeletal myoblasts, myocardial cells, endothelial cells, endothelial progenitor cells, bone-marrow derived mesenchymal cells and genetically modified cells are associated with the matrix. In another embodiment, a growth factor is associated with the matrix, for example and without limitation, a growth factor chosen from one or more of basic fibroblast growth factor (bFGF), acidic fibroblast growth factor (aFGF), vascular endothelial growth factor (VEGF), hepatocyte growth factor (HGF), insulin-like growth factors (IGF), transforming growth factor-beta pleiotrophin protein, midkine protein and IGF-1 is associated with the matrix. In certain non-limiting embodiments, the drug is chosen from one or more of a non-steroidal anti-inflammatory drug, an antibiotic, an anticlotting factor, an immunosuppressant, a glucocorticoid, a drug acting on an immunophilin, an interferon, a TNF binding proteins, a taxane, a statin, and a nitric oxide donor. In others, the drug is chosen from one or more of an NSAID, salicylic acid, indomethacin, sodium indomethacin trihydrate, salicylamide, naproxen, colchicine, fenoprofen, sulindac, diflunisal, diclofenac, indoprofen sodium salicylamide, antiinflammatory cytokines, antiinflammatory proteins, steroidal anti-inflammatory agents, heparin, Pebac, enoxaprin, aspirin, hirudin, plavix, bivalirudin, prasugrel, idraparinux, warfarin, coumadin, clopidogrel, PPACK, GGACK, tissue plasminogen activator, urokinase, streptokinase, a glucocorticoid, hydrocortisone, betamethisone, dexamethasone, flumethasone, isoflupredone, methylpred-nisolone, prednisone, prednisolone, triamcinolone acetonide, an antiangiogenic, fluorouracil, paclitaxel, doxorubicin, cisplatin, methotrexate, cyclophosphamide, etoposide, pegaptanib, lucentis, tryptophanyl-tRNA synthetase, retaane, CA4P, AdPEDF, VEGF-TRAP-EYE, AG-103958, Avastin, JSM6427, TG100801, ATG3, OT-551, endostatin, thalidomide, becacizumab, neovastat, an antiproliferative, sirolimus, paclitaxel, perillyl alcohol, farnesyl transferase inhibitors, FPTIII, L744, antiproliferative factor, Van 10/4, doxorubicin, 5-FU, Daunomycin, Mitomycin, dexamethasone, azathioprine, chlorambucil, cyclophosphamide, methotrexate, mofetil, vasoactive intestinal polypeptide, an antibody, a drug acting on immunophilins, cyclosporine, zotarolimus, everolimus, tacrolimus, sirolimus, an interferon, a TNF binding protein, a taxane, paclitaxel, docetaxel, a statin, atorvastatin, lovastatin, simvastatin, pravastatin, fluvastatin, rosuvastatin a nitric oxide donor or precursor, Angeli's Salt, L-Arginine, Free Base, Diethylamine NONOate, Diethylamine NONOate/AM, Glyco-SNAP-1, Glyco-SNAP-2, (±)-S-Nitroso-N-acetylpenicillamine, S-Nitrosoglutathione, NOC-5, NOC-7, NOC-9, NOC-12, NOC-18, NOR-1, NOR-3, SIN-1, Hydrochloride, Sodium Nitroprusside, Dihydrate, Spermine NONOate, Streptozotocin, an antibiotic, acyclovir, afloxacin, ampicillin, amphotericin B, atovaquone, azithromycin, ciprofloxacin, clarithromycin, clindamycin, clofazimine, dapsone, diclazaril, doxycycline, erythromycin, ethambutol, fluconazole, fluoroquinolones, foscarnet, ganciclovir, gentamicin, iatroconazole, isoniazid, ketoconazole, levofloxacin, lincomycin, miconazole, neomycin, norfloxacin, ofloxacin, paromomycin, penicillin, pentamidine, polymixin B, pyrazinamide, pyrimethamine, rifabutin, rifampin, sparfloxacin, streptomycin, sulfadiazine, tetracycline, tobramycin, trifluorouridine, trimethoprim sulphate, Zn-pyrithione, and silver salts such as chloride, bromide, iodide and periodate.

In yet another embodiment, a cardiac bypass method is provided comprising bypassing a coronary artery with a tubular tissue graft device comprising a vein and a contiguous restrictive fiber matrix of a bioerodible polymer about a circumference of the vein. The contiguous bioerodible polymer matrix is any matrix as described above and throughout this disclosure, and may include additional therapeutic agents as described above.

The bottom two panels are from a 24-hour ART (G) vs. wART (H) experiment. The arrows indicate proliferating cells. L indicates the PIJV lumen.

Figure 24:
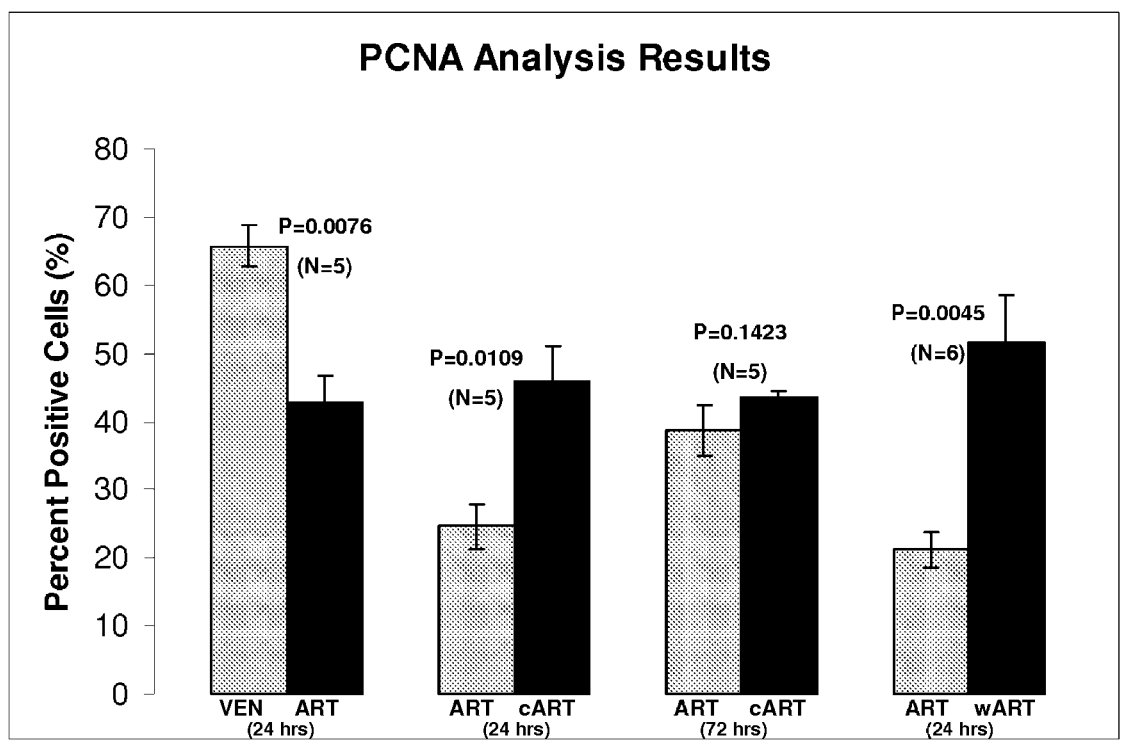

FIG. 24: Quantified immunohistochemistry results from HRP/ABC based PCNA expression analysis to assess the percentage of proliferating cells within PIJVs from all the ex vivo vascular perfusion experiments. The data are presented as mean±standard error of the mean.

Figure 25:
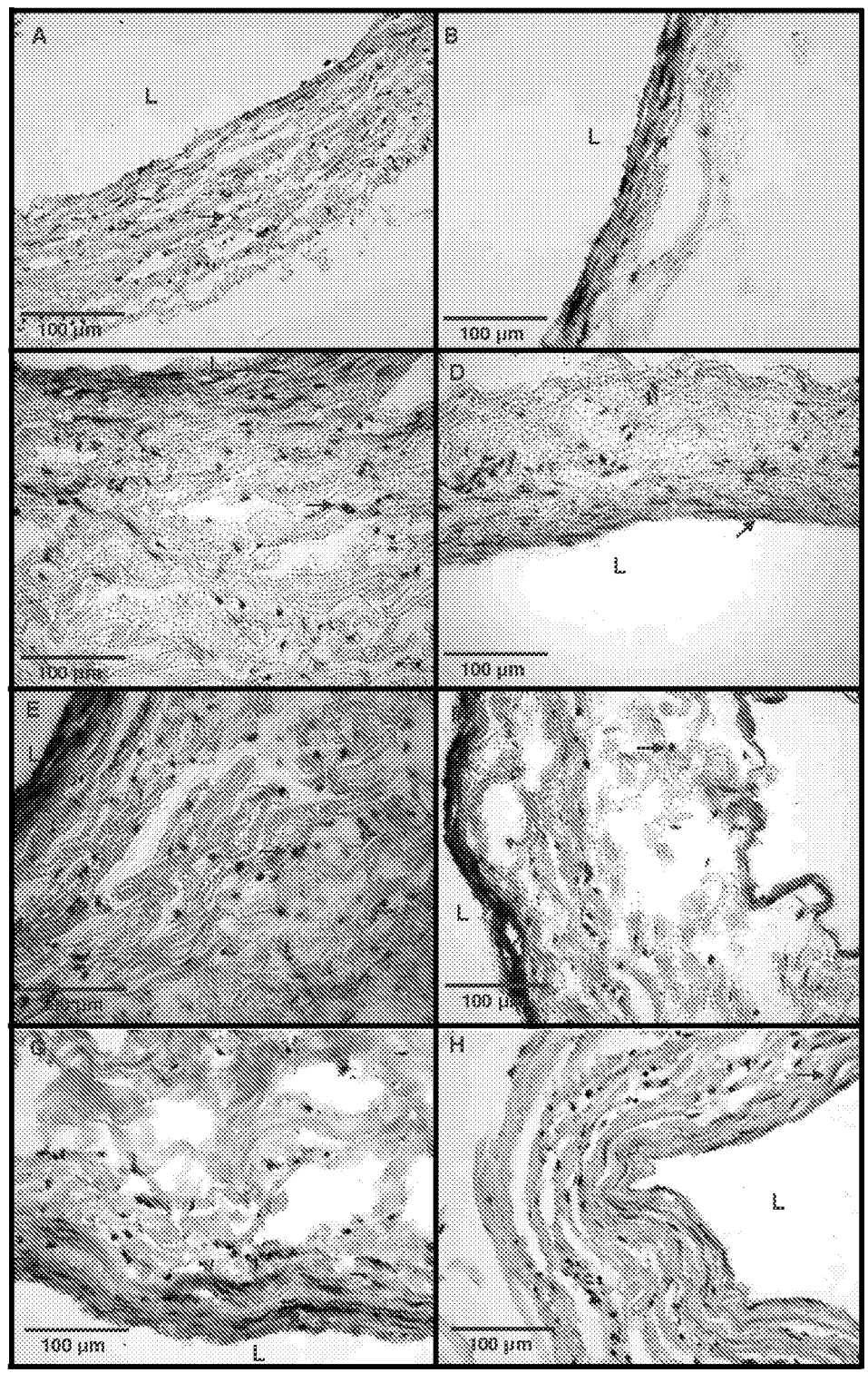

FIG. 25: Representative immunohistochemistry images from the HRP/ABC based Golgi complex analysis (originals in color). The top two panels are from a 24-hour VEN (A) vs. ART (B) experiment. The next two panels are from a 24-hour ART (C) vs. cART (D) experiment. The third row of panels are from a 72-hour ART (E) vs. cART (F) experiment. The bottom two panels are from a 24-hour ART (G) vs. wART (H) experiment. The arrows indicate positively stained cells. L indicates the PIJV lumen.

Figure 26:
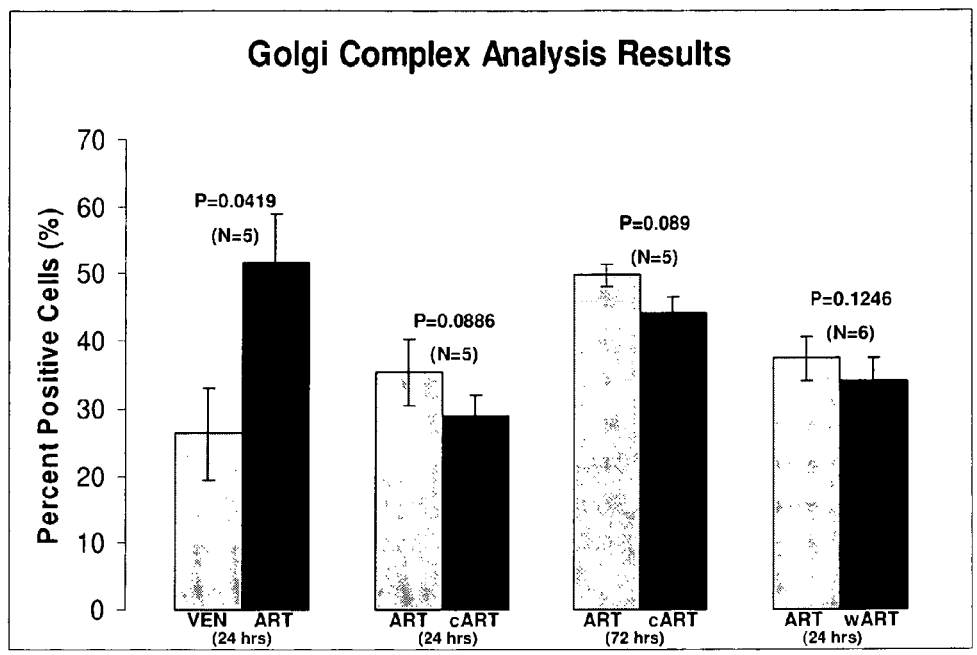

FIG. 26: Quantified immunohistochemistry results from HRP/ABC based Golgi complex expression analysis to assess the percentage cells staining positive for Golgi complex within PIJVs from all the ex vivo vascular perfusion experiments. The data are presented as mean±standard error of the mean.

Figure 27:

FIG. 27: Left: wrapped PIJV segment during the electrospinning process. Middle: wrapped PIJV implanted as a carotid interposition graft as proposed here. Right: unwrapped PIJV graft. Note that the wrapped PIJV (B) does not expand under arterial pressure as does the unwrapped vein (C).

Figure 28:

FIG. 28: Fluoroscopic angiography images from both spun and sham AVGs.

Figure 29:
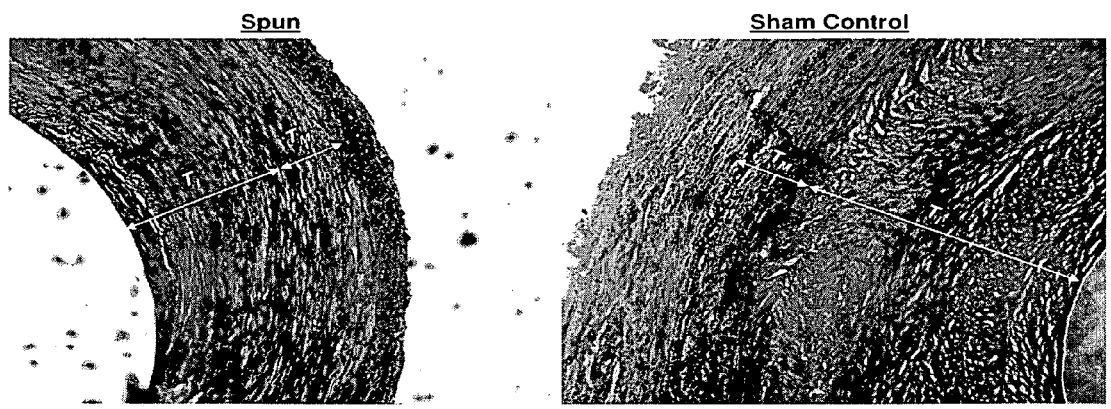

FIG. 29: Representative Movats pentachrome staining images that were used for morphometric measurements of IH (originals in color). The imtimal to medial thickness ratio was calculated using the above equation.

Figure 30:
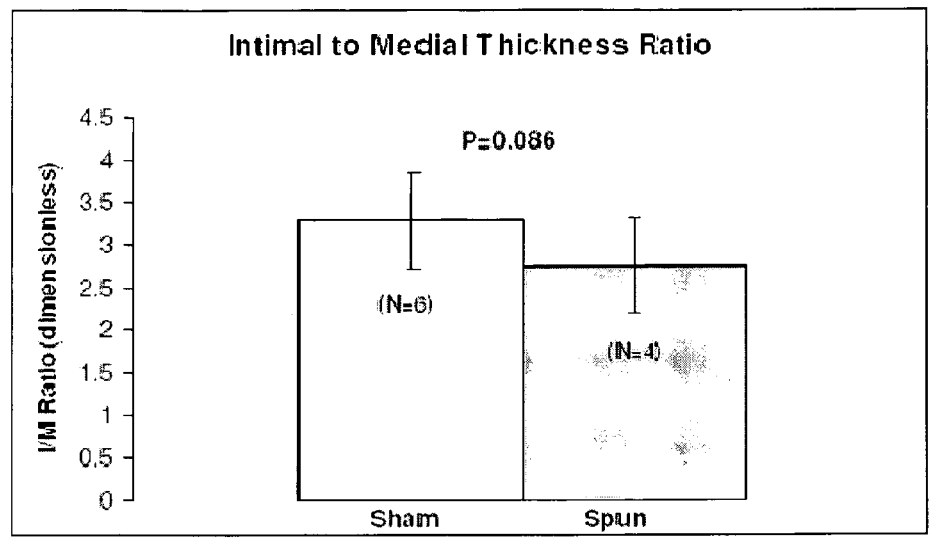

FIG. 30: Summary of quantified results from morphometric measurements of IH. P<0.05 was considered statistically significant. Note only a trend towards statistical significance was observed.

Figure 31:
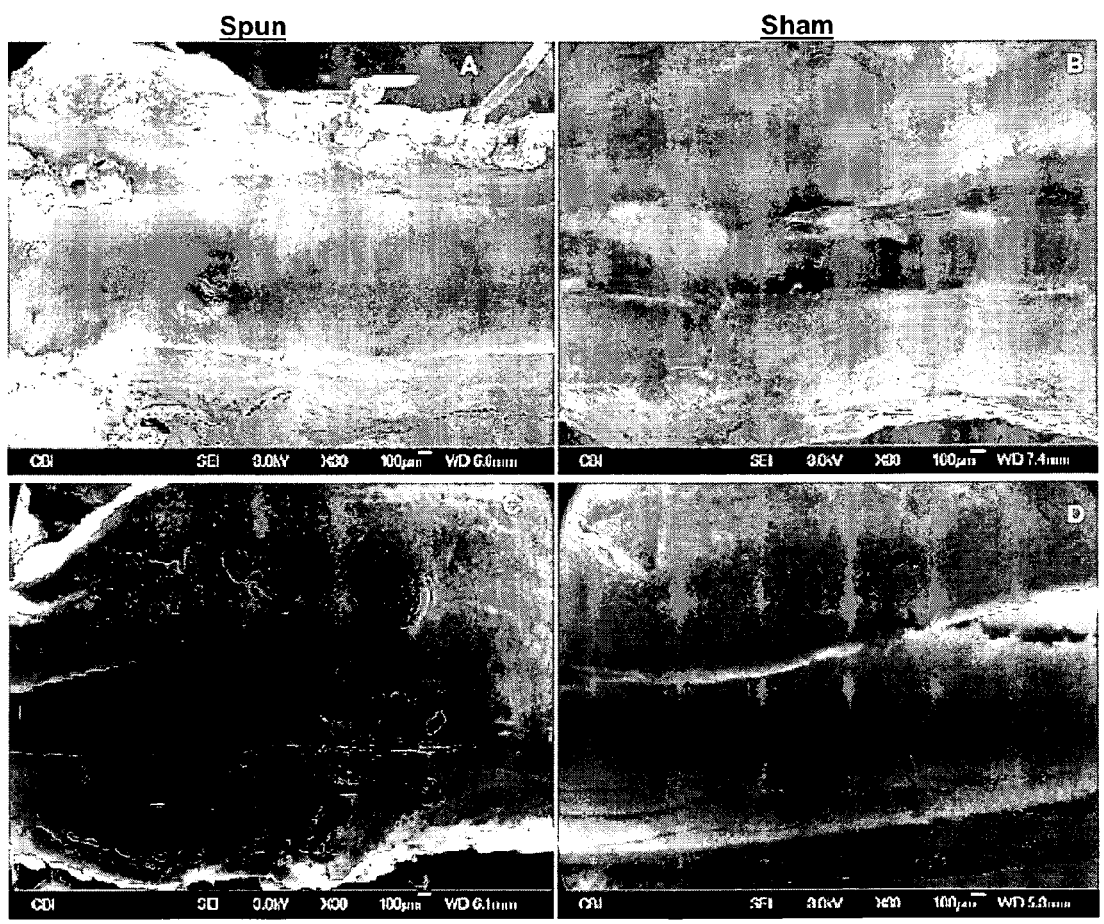

FIG. 31: Low magnification (30.times.) SEM images from two in vivo experiments where the AVGs were not occluded. A and B were from an experiment where the grafts were fully patent. C and D are from an experiment where the grafts were only partially occluded. These images show the anastomotic interface between the vein graft and the carotid artery.

Figure 32:
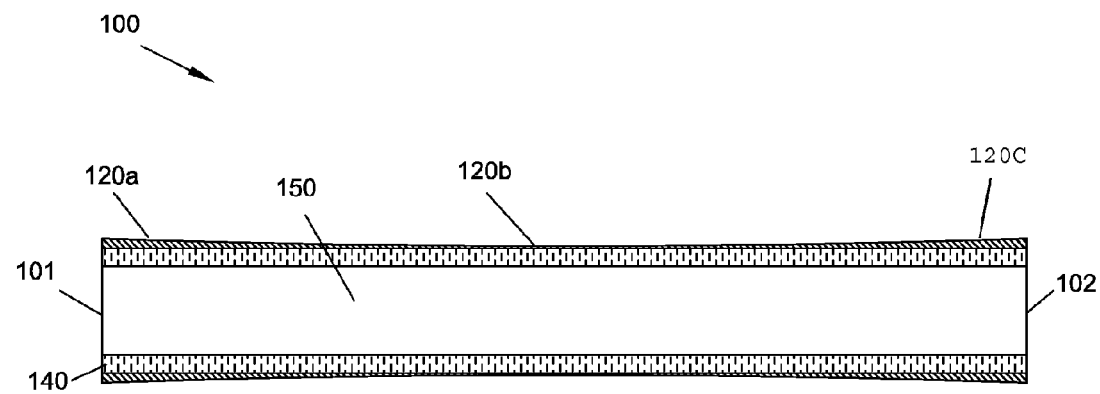

FIG. 32: Side sectional view of a tubular graft device of the present invention, including a tubular member with a surrounding fiber matrix whose thickness varies along at least a portion of the length of the device.

Figures 33A, 33B:
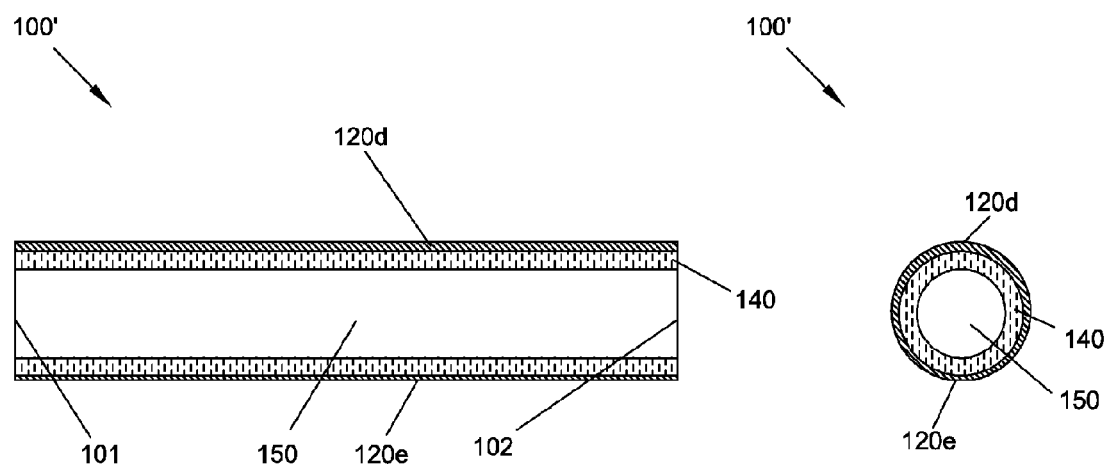

FIGS. 33a and 33B: Side and end sectional views respectively, of a tubular graft device of the present invention, including a tubular member with a surrounding fiber matrix whose thickness varies along at least a portion of a circumferential section of the device.

Figure 34:
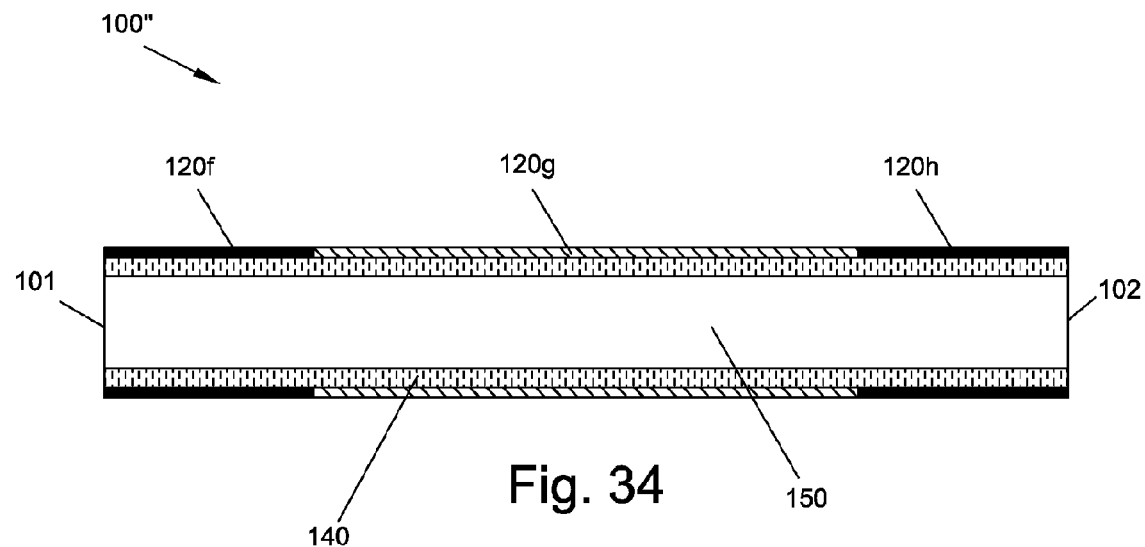

FIG. 34: Side sectional view of a tubular graft device of the present invention, including a tubular member with a surrounding fiber matrix whose properties vary along at least a portion of the length of the device.

Figure 35:
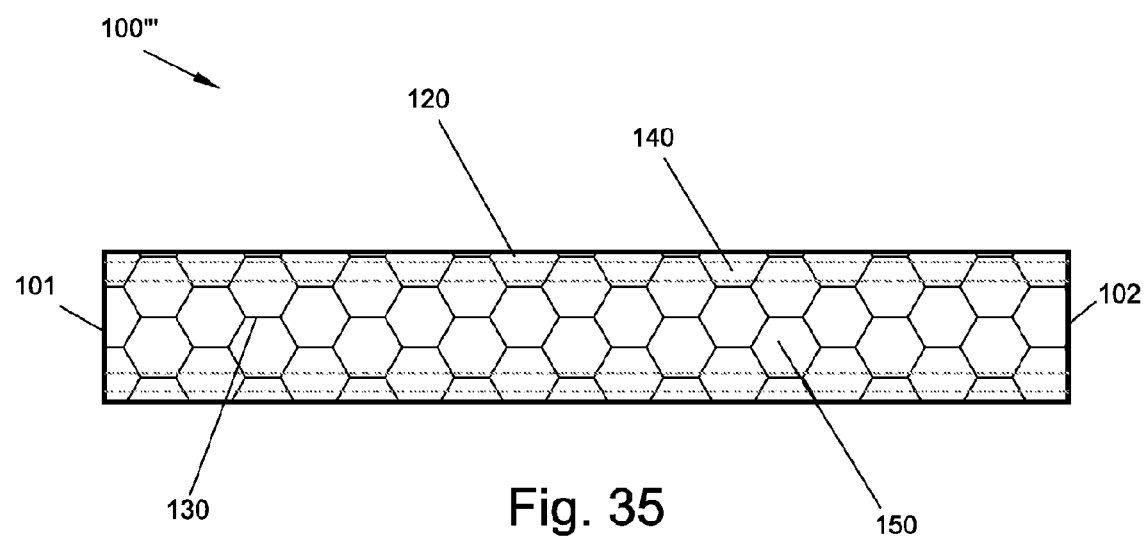

FIG. 35: Side sectional view of a tubular graft device of the present invention, including a tubular member surrounded by both a fiber matrix and a second scaffolding structure.

Figure 36:
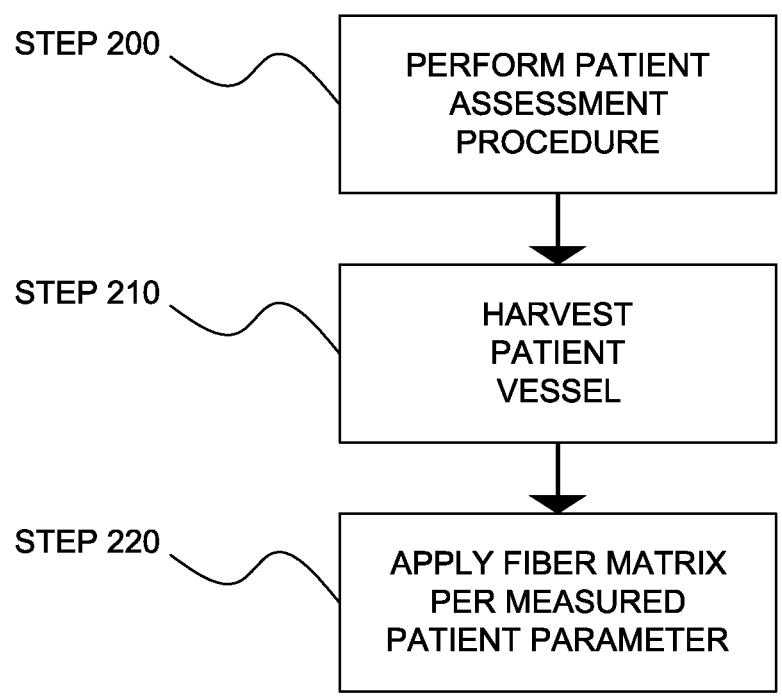

FIG. 36: Flow chart of a preferred method of manufacturing a tubular graft device of the present invention, including performing a patient assessment procedure, and applying a fiber matrix to a tubular member based on data obtained from the patient assessment.

Figure 37:
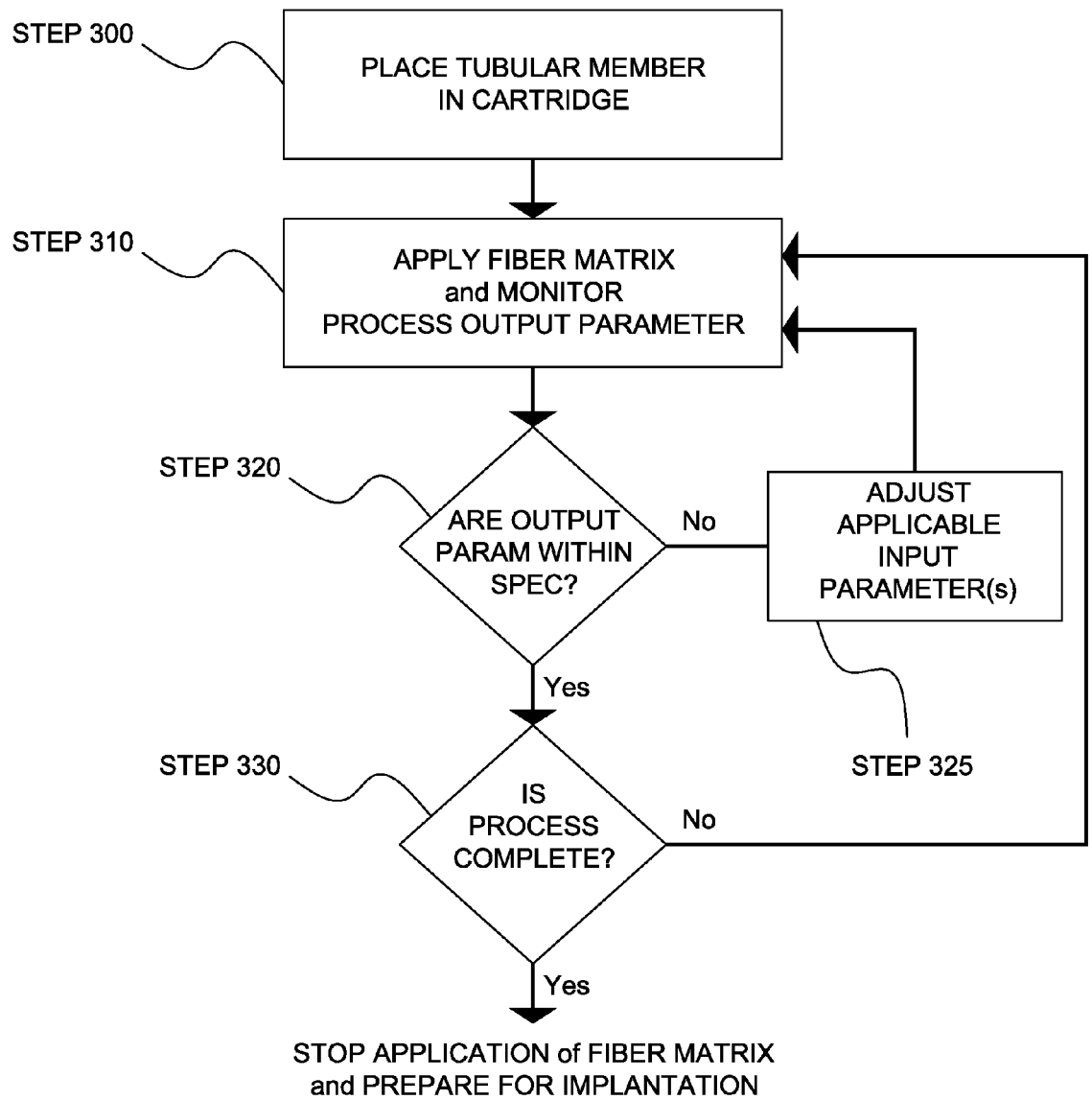

FIG. 37: Flow chart of a preferred method of manufacturing a tubular graft device of the present invention, including monitoring one or more process output parameters during application of a fiber matrix to a tubular member.

DETAILED DESCRIPTION

Provided herein is a method of mechanically conditioning an arterial vein graft, or any tubular tissue, typically, but not exclusively, in autologous, allogeneic xenogeneic transplantation procedures. To this end, provided herein is a method of wrapping tubular tissue, including, without limitation, a vein, artery, urethra, intestine, trachea, esophagus, ureter and fallopian tube (meaning that any portion of those tissue sources for the graft, and not implying that the entire stated anatomical structure is used for the graft purposes, though use of the entire structure or substantially the entire structure is one option. Thus, when the tubular tissue is said to be a vein, such as a saphenous vein, this does not mean that the entire saphenous vein has to be used). The structure is wrapped with a restrictive fiber matrix of a bioerodible polymer about a circumference of the tubular tissue. As described herein, a "fiber" an elongated, slender, elongated, thread-like and/or filamentous structure. A "matrix" is any two- or three-dimensional arrangement of elements (e.g., fibers), either ordered (e.g., in a woven or non-woven mesh) or randomly-arranged (as is typical with a mat of fibers typically produced by electrospinning).

The matrix typically is substantially or essentially contiguous about a circumference of a tubular tissue, meaning that the matrix forms a continuous, supportive ring on a surface and about a circumference of a portion, but not necessarily over the entire surface (e.g., length) of the tubular tissue. The matrix is "restrictive," meaning that the matrix is in substantial contact with the outer surface of the tubular tissue and restricts, hinders and/or prevents substantial circumferential expansion of the tubular tissue when grafted. The degree of restriction by the matrix typically is such that under typical arterial pressures, the tubular tissue is prevented from distending to substantially a maximum distension diameter for that tissue (see, e.g., FIG. 4). The matrix can be elastic, so long as it is restrictive. Where the matrix is bioerodible, the restrictive nature of the matrix declines over time as the matrix erodes.

In one non-limiting embodiment, the matrix is deposited onto a tubular tissue, such as a tubular anatomical structure or organ by electrospinning. In one particular non-limiting embodiment, the anatomical structure is a vein, such as a saphenous vein, that is used, for instance, in an arterial bypass procedure, such as a coronary arterial bypass procedure.

Although any useful method of depositing fine fibers onto a surface of a tubular tissue could be employed, electrospinning is a useful method of depositing substantially uniform fibers onto such a surface. Electrospinning permits fabrication of scaffolds that resemble the scale and fibrous nature of the native extracellular matrix (ECM). The ECM is composed of fibers, pores, and other surface features at the sub-micron and nanometer size scale. Such features directly impact cellular interactions with synthetic materials such as migration and orientation. Electrospinning also permits fabrication of oriented fibers to result in scaffolds with inherent anisotropy. These aligned scaffolds can influence cellular growth, morphology and ECM production. For example, Xu et al. found smooth muscle cell (SMC) alignment with poly(L-lactide-co-ε-caprolactone) fibers (Xu C. Y., Inai R., Kotaki M., Ramakrishna S., "Aligned biodegradable nanofibrous structure: a potential for blood vessel engineering", Biomaterials 2004 (25) 877-86.) and Lee et al. submitted aligned non-biodegradable polyurethane to mechanical stimulation and found cells cultured on aligned scaffolds produced more ECM than those on randomly organized scaffolds (Lee C. H., Shin H. J., Cho I. H., Kang Y. M. Kim I. A., Park K. D., Shin, J. W., "Nanofiber alignment and direction of mechanical strain affect the ECM production of human ACL fibroblast", Biomaterials 2005 (26) 1261-1270).

Generally, the process of electrospinning involves placing a polymer-containing fluid (e.g, a polymer solution, a polymer suspension, or a polymer melt) in a reservoir equipped with a small orifice, such as a needle or pipette tip and a metering pump. One electrode of a high voltage source is also placed in electrical contact with the polymer-containing fluid or orifice, while the other electrode is placed in electrical contact with a target (typically a collector screen or rotating mandrel). During electrospinning, the polymer-containing fluid is charged by the application of high voltage to the solution or orifice (e.g., about 3-15 kV) and then forced through the small orifice by the metering pump that provides steady flow. While the polymer-containing fluid at the orifice normally would have a hemispherical shape due to surface tension, the application of the high voltage causes the otherwise hemispherically shaped polymer-containing fluid at the orifice to elongate to form a conical shape known as a Taylor cone. With sufficiently high voltage applied to the polymer-containing fluid and/or orifice, the repulsive electrostatic force of the charged polymer-containing fluid overcomes the surface tension and a charged jet of fluid is ejected from the tip of the Taylor cone and accelerated towards the target, which typically is biased between −2 to −10 kV. Optionally, a focusing ring with an applied bias (e.g., 1-10 kV) can be used to direct the trajectory of the charged jet of polymer-containing fluid. As the charged jet of fluid travels towards the biased target, it undergoes a complicated whipping and bending motion. If the fluid is a polymer solution or suspension, the solvent typically evaporates during mid-flight, leaving behind a polymer fiber on the biased target. If the fluid is a polymer melt, the molten polymer cools and solidifies in mid-flight and is collected as a polymer fiber on the biased target. As the polymer fibers accumulate on the biased target, a non-woven, porous mesh (matrix) is formed on the biased target.

The properties of the electrospun elastomeric matrices can be tailored by varying the electrospinning conditions. For example, when the biased target is relatively close to the orifice, the resulting electrospun mesh tends to contain unevenly thick fibers, such that some areas of the fiber have a "bead-like" appearance. However, as the biased target is moved further away from the orifice, the fibers of the non-woven mesh tend to be more uniform in thickness. Moreover, the biased target can be moved relative to the orifice. In certain embodiments, the biased target is moved back and forth in a regular, periodic fashion, such that fibers of the non-woven mesh are substantially parallel to each other. When this is the case, the resulting non-woven mesh may have a higher resistance to strain in the direction parallel to the fibers, compared to the direction perpendicular to the fibers. In other embodiments, the biased target is moved randomly relative to the orifice, so that the resistance to strain in the plane of the non-woven mesh is isotropic. The target can also be a rotating mandrel. In this case, the properties of the non-woven mesh may be changed by varying the speed of rotation. The properties of the electrospun elastomeric scaffold may also be varied by changing the magnitude of the voltages applied to the electrospinning system. In one particularly preferred embodiment, the electrospinning apparatus includes an orifice biased to 12 kV, a target biased to −7 kV, and a focusing ring biased to 3 kV. Moreover, a useful orifice diameter is 0.047" (I.D.) and a useful target distance is about 23 cm. A useful range of high-voltage to be applied to a polymer suspension or melt is from 0.5-30 kV, more preferably 5-25 kV, even more preferably 10-15 kV.

Electrospinning may be performed using two or more nozzles, wherein each nozzle is a source of a different polymer solution. The nozzles may be biased with different biases or the same bias in order to tailor the physical and chemical properties of the resulting non-woven polymeric mesh. Additionally, many different targets may be used. In addition to a flat, plate-like target, a mandrel may be used as a target.

When the electrospinning is to be performed using a polymer suspension, the concentration of the polymeric component in the suspension can also be varied to modify the physical properties of the elastomeric scaffold. For example, when the polymeric component is present at relatively low concentration, the resulting fibers of the electrospun non-woven mesh have a smaller diameter than when the polymeric component is present at relatively high concentration. Without any intention to be limited by this theory, it is believed that lower concentration solutions have a lower viscosity, leading to faster flow through the orifice to produce thinner fibers. One skilled in the art can adjust polymer concentrations to obtain fibers of desired characteristics. Useful ranges of concentrations for the polymer component include from about 1% wt. to about 15% wt., from about 4% wt. to about 10% wt. and from about 6% wt. to about 8% wt.

In use, the mandrel is placed inside a tubular tissue, such as a vein, and polymer fibers are deposited about the circumference of at least a portion of the tissue by rotation of the mandrel. The mandrel can be reciprocated longitudinally between the spinneret and collector to increase the coverage of the tubular tissue.

Thickness of the matrix can be controlled by either adjusting the viscosity of the polymer composition to be deposited and/or adjusting duration of the electrospinning. Use of more viscous polymer composition may result in thicker fibers, requiring less time to deposit a matrix of a desired thickness. Use of a less viscous polymer composition may result in thinner fibers, requiring increased deposition time to deposit a matrix of a desired thickness. The thickness of the matrix and fibers within the matrix affects the speed of bioerosion of the matrix. These parameters are optimized, depending on the end-use of the matrix, to achieve a desired or optimal physiological effect.

The biodegradation rate of the polymer matrix may be manipulated, optimized or otherwise adjusted so that the matrix degrades over a useful time period. For instance, in the case of a coronary artery bypass, it is desirable that the matrix dissolves over 12 hours or more so as to prevent substantial sudden stress on the graft. The polymer degrades over a desired period of time so that the mechanical support offered by the polymer matrix is gradually reduced over that period and the vein would be exposed to gradually increasing levels of CWS.

This new approach would have two potential applications. In the first non-limiting application, the matrix can be used as a peri-surgical tool for the modification of vein segments intended for use as an AVG. The modification of a vein or other tubular tissue or anatomical structure may be performed at bedside, immediately after removal from the body and just prior to grafting, for example and without limitation, during arterial bypass surgery. In one non-limiting example, after the saphenous vein is harvested, and while the surgeon is exposing the surgical (graft) site, the polymer wrap would be electrospun onto the vein just prior to it being used for the bypass procedure.

In a second non-limiting embodiment, the polymer matrix can be used as a vehicle for the delivery of support to AVGs. While modification of the mechanical environment of a vein graft over time could itself improve AVG patency, delivery of active agents and biological (cellular) support to AVGs may prove desirable in many instances. By tuning an electrospun polymer wrap, in which active agents and/or biologicals are incorporated, to degrade at a desired rate, the rate of delivery of these support modalities could be controlled.

Previous approaches to perivascular placement of a wrap to deliver support to AVGs had rate-limiting barriers to clinical translation, and the approach presented herein, using an electrospun biodegradable polymer, addresses these limitations.

The use of an external sheath around vein grafts was first described by Parsonnet et al. They showed that the sheath prevented dilatation, that it was well accepted by the host tissue, and that there was no difference in the tensile strength between supported and non-supported vessels (Parsonnet V, Lari A A, and Shah I H. New stent for support of veins in arterial grafts. Arch Surg. 1963; 87: 696-702). Karayannacos et al. showed reduced thrombosis and sub-endothelial proliferation in AVGs with both loose and tight fitting Dacron mesh sheaths compared with unsupported control grafts (Karayannacos P E, Hostetler J R, Bond M G, Kakos G S, Williams R A, Kilman J W, and Vasko J S. Late failure in vein grafts: Mediating factors in subendothelial fibromuscular hyperplasia. Ann Surg. 1978; 187(2): 183-8). Mehta et al. demonstrated that placement of an external, macroporous, nonrestrictive, polyester stent reduces neointima formation in porcine vein grafts (Mehta D, George S J, Jeremy J Y, Izzat M B, Southgate K M, Bryan A J, Newby A C, and Angelini G D. External stenting reduces long-term medial and neointimal thickening and platelet derived growth factor expression in a pig model of arteriovenous bypass grafting. Nat. Med. 1998; 4(2): 235-9). More recently, polytetrofluoroethylene sheaths were used to permanently restrict AVGs from expansion under arterial pressure and this led to reduced IH formation in a pig model (Liu S Q, Moore M M, Glucksberg M R, Mockros L F, Grotberg J B, and Mok A P. Partial prevention of monocyte and granulocyte activation in experimental vein grafts by using a biomechanical engineering approach. J. Biomech. 1999; 32(11): 1165-75).

Clinical translation of permanent mechanical support to AVGs has not yet been reported, most likely due to the unfavorable inflammatory response to biodurable synthetic materials in vascular applications (Bunt T J. Synthetic vascular graft infections. I. Graft infections. Surgery. 1983; 93(6): 733-46 and Edwards W H, Jr., Martin R S, 3rd, Jenkins J M, Edwards W H, Sr., and Mulherin J L, Jr. Primary graft infections. J Vasc Surg. 1987; 6(3): 235-9). This limitation motivated Vijayan et al. and Jeremy et al. to use a polyglactin based biodegradable sheath to reduce IH in AVGs (Jeremy J Y, Bulbulia R, Johnson J L, Gadsdon P, Vijayan V, Shukla N, Smith F C, and Angelini G D. A bioabsorbable (polyglactin), nonrestrictive, external sheath inhibits porcine saphenous vein graft thickening. J Thorac Cardiovasc Surg. 2004; 127(6): 1766-72; Vijayan V, Shukla N, Johnson J L, Gadsdon P, Angelini G D, Smith F C, Baird R, and Jeremy J Y. Long-term reduction of medial and intimal thickening in porcine saphenous vein grafts with a polyglactin biodegradable external sheath. J Vasc Surg. 2004; 40(5): 1011-9; and Vijayan V, Smith F C, Angelini G D, Bulbulia R A, and Jeremy J Y. External supports and the prevention of neointima formation in vein grafts. Eur J Vasc Endovasc Surg. 2002; 24(1): 13-22). The noted beneficial effects included enhanced neo-vasa-vasorum development over unwrapped controls (Vijayan V, Shukla N, Johnson J L, Gadsdon P, Angelini G D, Smith F C, Baird R, and Jeremy J Y. Long-term reduction of medial and intimal thickening in porcine saphenous vein grafts with a polyglactin biodegradable external sheath. Vasc Surg. 2004; 40(5): 1011-9). However, these biodegradable sheaths were loose-fitting and allowed the AVGs to expand to their maximum diameters under arterial pressure, and thus did not offer mechanical support against the increased level of CWS. Prior to the approach used by Vijayan et al. (Vijayan V, Shukla N, Johnson J L, Gadsdon P, Angelini G D, Smith F C, Baird R, and Jeremy J Y. Long-term reduction of medial and intimal thickening in porcine saphenous vein grafts with a polyglactin biodegradable external sheath. J Vasc Surg. 2004; 40(5): 1011-9 and Vijayan V, Smith F C, Angelini G D, Bulbulia R A, and Jeremy J Y. External supports and the prevention of neointima formation in vein grafts. Eur J Vasc Endovasc Surg. 2002; 24(1): 13-22) and Jeremy et al. (Jeremy J Y, Bulbulia R, Johnson J L, Gadsdon P, Vijayan V, Shukla N, Smith F C, and Angelini G D. A bioabsorbable (polyglactin), nonrestrictive, external sheath inhibits porcine saphenous vein graft thickening. J Thorac Cardiovasc Surg. 2004; 127(6): 1766-72), Huynh et al. used a temporary external collagen tube support to reduce IH formation in rabbit vein grafts. These collagen tubes were also non-restrictive, and no mention of the degradation kinetics was reported (Huynh T T, Iaccarino G, Davies M G, Safi H J, Koch W J, and Hagen P O. External support modulates g protein expression and receptor coupling in experimental vein grafts. Surgery. 1999; 126(2): 127-34). It has been reported that electrospun cross-linked collagen degrades very rapidly in an aqueous solution (Rho K S, Jeong L, Lee G, Seo B M, Park Y J, Hong S D, Roh S, Cho J J, Park W H, and Min B M. Electrospinning of collagen nanofibers: Effects on the behavior of normal human keratinocytes and early-stage wound healing. Biomaterials. 2006; 27(8): 1452-61) and hence the structural support offered to AVGs by sheaths made of collagen alone may be too temporary to be effective over the long-term. An external AVG sheath developed by Liao et al. was designed to degrade at a desired rate in order to transfer CWS to an AVG gradually over time. Poly lactic-co glycolic acid sheets were prefabricated into tubes by wrapping around a Teflon rod, and therefore are not customizable to each AVG (Liao S W, Lu X, Putnam A J, and Kassab G S. A novel time-varying poly lactic-co glycolic acid external sheath for vein grafts designed under physiological loading. Tissue Eng. 2007; 13(12): 2855-62). That is, as with previous approaches the Liao et al. approach allows expansion of an AVG under arterial pressure before delivering any mechanical support. The degradation kinetics and resulting CWS vs. time profile in the sheaths, not in the mid-AVG-wall as described here, were reported. Our approach addresses the two major limitations associated with the previous work described above, specifically with respect to biodurable and/or non-restrictive external sheaths.

Delivery of mechanical support to AVGs is but one possibility for an adventitial wrap. Other applications could be as a vehicle for the local delivery of biochemicals, drugs, genes, or cells. Kanjickal et al. used a poly(ethylene glycol) hydrogel for sustained local delivery of cyclosporine to AVGs, and successfully reduced anastomotic IH development (Kanjickal D, Lopina S, Evancho-Chapman M M, Schmidt S, Donovan D, and Springhetti S. Polymeric sustained local drug delivery system for the prevention of vascular intimal hyperplasia. J Biomed Mater Res A. 2004; 68(3): 489-95). In another study, Cagiannos et al. used a polytetrafluoroethylene sheath to locally deliver rapamycin (sirolimus) to AVGs, and effectively reduced anastomotic IH in a pig model (Cagiannos C, Abul-Khoudoud O R, DeRijk W, Shell D Ht, Jennings L K, Tolley E A, Handorf C R, and Fabian T C. Rapamycin-coated expanded polytetrafluoroethylene bypass grafts exhibit decreased anastomotic neointimal hyperplasia in a porcine model. J Vasc Surg. 2005; 42(5): 980-8). More recently, Kohler et al. used a biodegradable mesh to deliver paclitaxel to effectively reduce IH at the graft-vein anastomosis in a sheep model of dialysis access (Kohler T R, Toleikis P M, Gravett D M, and Avelar R L. Inhibition of neointimal hyperplasia in a sheep model of dialysis access failure with the bioabsorbable vascular wrap paclitaxel-eluting mesh. J Vasc Surg. 2007; 45(5): 1029-1037; discussion 1037-8). Such activities could theoretically be incorporated using the electrospun polymer wrap technique, with the potential to control the delivery rate to some extent by tuning the degradation rate of the electrospun polymer wrap.

To our knowledge, delivery of cells via a biodegradable AVG wrap/sheath has not been previously reported and hence this possible future application of the adventitial wrap would be novel. The polymer that was used here has been characterized (Stankus J J, Guan J, and Wagner W R. Fabrication of biodegradable elastomeric scaffolds with submicron morphologies. J Biomed Mater Res A. 2004; 70(4): 603-14), and successfully micro-integrated with viable SMCs (Stankus J J, Guan J, Fujimoto K, and Wagner W R. Microintegrating smooth muscle cells into a biodegradable, elastomeric fiber matrix. Biomaterials. 2006; 27(5): 735-44), and would lend itself to this potential future application.

A biodegradeable polymer is "biocompatible" in that the polymer and degradation products thereof are substantially non-toxic, including non-carcinogenic and non-immunogenic, and are cleared or otherwise degraded in a biological system, such as an organism (patient) without substantial toxic effect. Non-limiting examples of degradation mechanisms within a biological system include chemical reactions, hydrolysis reactions, and enzymatic cleavage. Biodegradable polymers include natural polymers, synthetic polymers, and blends of natural and synthetic polymers. For example and without limitation, natural polymers include chitosan, collagen, elastin, alginate, cellulose, polyalkanoates, hyaluronic acid, or gelatin. Natural polymers can be obtained from natural sources or can be prepared by synthetic methods (including by recombinant methods) in their use in the context of the technologies described herein. Non-limiting examples of synthetic polymers include: homopolymers, heteropolymers, co-polymers and block polymers or co-polymers.

As used herein, the term "polymer composition" is a composition comprising one or more polymers. As a class, "polymers" includes homopolymers, heteropolymers, co-polymers, block polymers, block co-polymers and can be both natural and synthetic. Homopolymers contain one type of building block, or monomer, whereas co-polymers contain more than one type of monomer. For example and without limitation, polymers comprising monomers derived from alpha-hydroxy acids including polylactide, poly(lactide-co-glycolide), poly(L-lactide-co-caprolactone), polyglycolic acid, poly(dl-lactide-co-glycolide), poly(1-lactide-co-dl-lactide); monomers derived from esters including polyhydroxybutyrate, polyhydroxyvalerate, polydioxanone and polygalactin; monomers derived from lactones including polycaprolactone; monomers derived from carbonates including polycarbonate, polyglyconate, poly(glycolide-co-trimethylene carbonate), poly(glycolide-co-trimethylene carbonate-co-dioxanone); monomers joined through urethane linkages, including polyurethane, poly(ester urethane) urea elastomer.

According to a non-limiting embodiment, the polymer composition comprises one or both of a collagen and an elastin. Collagen is a common ECM component and typically is degraded in vivo at a rate faster than many synthetic bioerodable polymers. Therefore, manipulation of collagen content in the polymer composition can be used as a method of modifying bierosion rates in vivo. Collagen may be present in the polymer composition in any useful range, including, without limitation, from about 2% wt. to about 95% wt., but more typically in the range of from about 25% wt. to about 75% wt., inclusive of all ranges and points therebetween, including from about 40% wt. to about 75%, including about 75% wt. and about 42.3% wt. Elastin may be incorporated into the polymer composition in order to provide increased elasticity. Use of elastin can permit slight circumferential expansion of the restrictive matrix in order to assist the tubular tissue, such as a vein, adapt to its new function, such as an arterial use. Elastin may be present in the polymer composition in any useful range, including without limitation, from about 2% wt. to about 50% wt., inclusive of all ranges and points therebetween, including from about 40% wt. and about 42.3% wt., inclusive of all integers and all points therebetween and equivalents thereof. In one non-limiting embodiment, collagen and elastin are present in approximately equal amounts in the polymer composition. In another embodiment, the sum of the collagen and elastin content in the polymer composition is in any useful range, including, without limitation, from about 2% wt. to about 95% wt., but more typically in the range of from about 25% wt. to about 75% wt., inclusive of all ranges and points therebetween, including from about 40% wt. to about 75%, including about 75% wt. and about 42.3% wt.

All ranges or numerical values stated herein, whether or not preceded by the term "about" unless stated otherwise are considered to be preceded by the term "about" to account for variations in precision of measurement and functionally equivalent ranges. For example, collagen may be stated as being present in a polymer composition at 10% wt., but, due to measurement variation, may be literally present at 10% wt.±0.05% wt., 0.10% wt. or 1.0% wt., and is likely to function in the same manner at such weight percentages.

As used herein, the terms "comprising," "comprise" or "comprised," and variations thereof, are meant to be open ended. The terms "a" and "an" are intended to refer to one or more.

As used herein, the term "patient" or "subject" refers to members of the animal kingdom including but not limited to human beings.

A polymer "comprises" or is "derived from" a stated monomer if that monomer is incorporated into the polymer. Thus, the incorporated monomer that the polymer comprises is not the same as the monomer prior to incorporation into a polymer, in that at the very least, certain terminal groups are incorporated into the polymer backbone. A polymer is said to comprise a specific type of linkage if that linkage is present in the polymer.

The biodegradable polymers described herein are said to be bioerodible. By "bioerodible", it is meant that the polymer, once implanted and placed in contact with bodily fluids and tissues, will degrade either partially or completely through chemical reactions with the bodily fluids and/or tissues, typically and often preferably over a time period of hours, days, weeks or months. Non-limiting examples of such chemical reactions include acid/base reactions, hydrolysis reactions, and enzymatic cleavage. In certain embodiments, the polymers contain labile chemical moieties, examples of which include esters, anhydrides, polyanhydrides, or amides. Alternatively, the polymers may contain peptides or biomacromolecules as building blocks which are susceptible chemical reactions once placed in situ. For example, the polymer may contain the peptide sequence alanine-alanine-lysine, which confers enzymatic lability to the polymer. In another embodiment, the polymer may include an extracellular matrix protein as a building block, such as collagen.

The polymer or polymers typically will be selected so that it degrades in situ over a time period to optimize mechanical conditioning of the tissue. Non-limiting examples of useful in situ degradation rates include between 12 hours and 2 weeks, and increments of 1, 2, 3, 6, 12, 24 and/or 48 hours therebetween.

The biodegradable polymers useful herein also can be elastomeric. Generally, any elastomeric polymer that has properties similar to that of the soft tissue to be replaced or repaired is appropriate. For example, in certain embodiments, the polymers used to make the wrap are highly distensible. Non-limiting examples of suitable polymers include those that have a breaking strain of from 100% to 1700%, more preferably between 200% and 800%, and even more preferably between 325% and 600%. In particularly preferred embodiments, the breaking strain of the polymer is between 5% and 50%, more preferably between 10% and 40%, and even more preferably between 20% and 30%. Further, it is often useful to select polymers with tensile strengths of from 10 kPa-30 MPa, more preferably from 5-25 MPa, and even more preferably between 8 and 20 MPa. In certain embodiments, the initial modulus is between 10 kPa to 100 MPa, more preferably between 10 and 90 MPa, and even more preferably between 20 and 70 MPa.

In certain embodiments, the polymers used herein also release therapeutic agents when they degrade within the patient's body. For example, the individual building blocks of the polymers may be chosen such that the building blocks themselves provide a therapeutic benefit when released in situ through the degradation process. In one particularly preferred embodiment, one of the polymer building blocks is putrescine, which has been implicated as a substance that causes cell growth and cell differentiation.

In one embodiment, the fibers comprise a biodegradable poly(ester urethane) urea elastomer (PEUU). An example of such a PEUU is an elastomeric polymer made from polycaprolactonediol (MW 2000) and 1,4-diisocyanatobutane, with a diamine, such as putrescine as the chain extender. A suitable PEUU polymer may be made by a two-step polymerization process whereby polycaprolactonediol (MW 2000), 1,4-diisocyanatobutane, and putrescine are combined in a 2:1:1 molar ratio. In the first polymerization step, a 15 wt % solution of 1,4-diisocyanatobutane in DMSO is stirred continuously with a 25 wt % solution of diol in DMSO. In the second step, stannous octoate is added and the mixture is allowed to react at 75° C. for 3 hours, with the addition of triethylamine to aid dissolution. The elastomeric polymer may also be a poly(ether ester urethane) urea elastomer (PEEUU). For example, the PEEUU may be made by reacting polycaprolactone-b-polyethylene glycol-b-polycaprolactone triblock copolymers with 1,4-diisocyanatobutane and putrescine. In a preferred embodiment, PEEUU is obtained by a two-step reaction using a 2:1:1 reactant stoichiometry of 1,4-diisocyanatobutane:triblock copolymer:putrescine. In the first polymerization step, a 15 wt % solution of 1,4-diisocyanatobutane in DMSO is stirred continuously with a 25 wt % solution of triblock compolymer diol in DMSO. In the second step, stannous octoate is added and the mixture is allowed to react at 75° C. for 3 hours. The reaction mixture is then cooled to room temperature and allowed to continue for 18 h. The PEEUU polymer solution is then precipitated with distilled water and the wet polymer is immersed in isopropanol for 3 days to remove unreacted monomer and dried under vacuum.

In other embodiments, at least one therapeutic agent is added to the bioerodible fibers. Useful therapeutic agents include any substance that can be coated on, attached, absorbed, adsorbed, embedded or otherwise associated with the bioerodible fibers that would provide a therapeutic benefit to a patient. Therapeutic agent may be blended with the polymer while the polymer is being processed. For example, the therapeutic agent may be dissolved in a solvent (e.g., DMSO) and added to the polymer blend during processing. In another embodiment, the therapeutic agent is mixed with a carrier polymer (for example and without limitation, a polyethylene glycol hydrogel or polylactic-glycolic acid microparticles) which is subsequently processed with the elastomeric polymer. By blending the therapeutic agent with a carrier polymer or the elastomeric polymer itself, the rate of release of the therapeutic agent may be controlled by the rate of polymer degradation. In one embodiment, a bioerodible hydrogel comprising an active agent or cells is applied to the bioerodible fibers after they are applied to a surface of a tubular tissue.

As used herein, "biodegradable", "bioresorbable" and "bioerodible" are synonymous. Also, the descriptor "tubular" does not refer specifically to a geometrically perfect tube having a constant diameter and a circular cross-section. It also embraces tissues having non-circular and varying cross sections, and can have a variable diameter, and thus any shape having a contiguous wall surrounding a lumen (that is, they are hollow), and two openings into the lumen such that a liquid, solid or gas can travel from one opening to the other. As indicated herein, specific non-limiting, but illustrative examples of tubular tissues include arterial, urethral, intestinal, esophageal, ureter, tracheal, bronchial, and fallopian tube tissue.

Additionally, other active agents that may be incorporated into the bioerodible fibers include, without limitation, anti-inflammatories, such as, without limitation, NSAIDs (non-steroidal anti-inflammatory drugs) such as salicylic acid, indomethacin, sodium indomethacin trihydrate, salicylamide, naproxen, colchicine, fenoprofen, sulindac, diflunisal, diclofenac, indoprofen sodium salicylamide, antiinflammatory cytokines, and antiinflammatory proteins or steroidal anti-inflammatory agents); antibiotics; anticlotting factors such as heparin, Pebac, enoxaprin, aspirin, hirudin, plavix, bivalirudin, prasugrel, idraparinux, warfarin, coumadin, clopidogrel, PPACK (D-phenylalanyl-L-prolyl-L-arginine chloromethyl ketone) and GGACK (L-Glutamyl-L-Glycyl-L-Arginyl chloromethyl ketone), tissue plasminogen activator, urokinase, and streptokinase; growth factors. Other active agents include, without limitation: (1) immunosuppressants; glucocorticoids such as hydrocortisone, betamethisone, dexamethasone, flumethasone, isoflupredone, methylpred-nisolone, prednisone, prednisolone, and triamcinolone acetonide; (2) antiangiogenics such as fluorouracil, paclitaxel, doxorubicin, cisplatin, methotrexate, cyclophosphamide, etoposide, pegaptanib, lucentis, tryptophanyl-tRNA synthetase, retaane, CA4P, AdPEDF, VEGF-TRAP-EYE, AG-103958, Avastin, JSM6427, TG100801, ATG3, OT-551, endostatin, thalidomide, becacizumab, neovastat; (3) antiproliferatives such as sirolimus, paclitaxel, perillyl alcohol, farnesyl transferase inhibitors, FPTIII, L744, antiproliferative factor, Van 10/4, doxorubicin, 5-FU, Daunomycin, Mitomycin, dexamethasone, azathioprine, chlorambucil, cyclophosphamide, methotrexate, mofetil, vasoactive intestinal polypeptide, and PACAP; (4) antibodies; drugs acting on immunophilins, such as cyclosporine, zotarolimus, everolimus, tacrolimus and sirolimus (rapamycin), interferons, TNF binding proteins; (5) taxanes, such as paclitaxel and docetaxel; statins, such as atorvastatin, lovastatin, simvastatin, pravastatin, fluvastatin and rosuvastatin; (6) nitric oxide donors or precursors, such as, without limitation, Angeli's Salt, L-Arginine, Free Base, Diethylamine NONOate, Diethylamine NONOate/AM, Glyco-SNAP-1, Glyco-SNAP-2, (±)-S-Nitroso-N-acetylpenicillamine, S-Nitrosoglutathione, NOC-5, NOC-7, NOC-9, NOC-12, NOC-18, NOR-1, NOR-3, SIN-1, Hydrochloride, Sodium Nitroprusside, Dihydrate, Spermine NONOate, Streptozotocin; and (7) antibiotics, such as, without limitation: acyclovir, afloxacin, ampicillin, amphotericin B, atovaquone, azithromycin, ciprofloxacin, clarithromycin, clindamycin, clofazimine, dapsone, diclazaril, doxycycline, erythromycin, ethambutol, fluconazole, fluoroquinolones, foscarnet, ganciclovir, gentamicin, iatroconazole, isoniazid, ketoconazole, levofloxacin, lincomycin, miconazole, neomycin, norfloxacin, ofloxacin, paromomycin, penicillin, pentamidine, polymixin B, pyrazinamide, pyrimethamine, rifabutin, rifampin, sparfloxacin, streptomycin, sulfadiazine, tetracycline, tobramycin, trifluorouridine, trimethoprim sulphate, Zn-pyrithione, and silver salts such as chloride, bromide, iodide and periodate.

Cells may be microintegrated within the restrictive, bioerodible matrix using a variety of methods. For example, the matrix may be submersed in an appropriate growth medium for the cells of interest, and then directly exposed to the cells. The cells are allowed to proliferate on the surface and interstices of the matrix. The matrix is then removed from the growth medium, washed if necessary, and implanted. But because electrospun non-woven fabrics often have pore sizes that are relatively small (e.g., compared to the pore sizes of non-woven fabrics fabricated by other methods such as salt leaching or thermally induced phase separation), culturing cells on the surface of the scaffold is usually used when microintegration of cells only near the surface of the elastomeric scaffold is desired.

In another embodiment, the cells of interest are dissolved into an appropriate solution (e.g., a growth medium or buffer) and then sprayed onto a restrictive, bioerodible matrix while the matrix is being formed by electrospinning. This method is particularly suitable when a highly cellularized tissue engineered construct is desired. In one embodiment, pressure spraying (i.e., spraying cells from a nozzle under pressure) is used to deposit the cells. In another, the cells are electrosprayed onto the non-woven mesh during electrospinning. As described herein, electrospraying involves subjecting a cell-containing solution with an appropriate viscosity and concentration to an electric field sufficient to produce a spray of small charged droplets of solution that contain cells. In one experiment (not shown), cell viability was examined for smooth muscle cells (SMCs) sprayed under different conditions. These different conditions include spraying alone, spraying onto a target charged at −15 kV, spraying onto a target charged at −15 kV with PEUU electro spinning, electrospraying at 10 kV onto a target charged at −15 kV, and electrospraying at 10 kV onto a target charged at −15 kV with PEUU electrospinning. A significant reduction in SMC viability resulted from spraying cells through the nozzle. Without any intent to be bound by theory, it is believed that the physical forces of the pressurized spray in combination with the exposure of cells to processing solvents may have caused this result since viability was lost both from spraying alone and even more so by spraying during electrospun PEUU (e-PEUU) fabrication. Decreased viability from cell aerosol spraying has been reported by others and found to depend largely on nozzle diameter, spray pressure, and solution viscosity (Veazey W. S., Anusavice K. J., Moore K., "Mammalian cell delivery via aerosol deposition", J. Biomed. Mater. Res. 2005 (72B)334-8.). Therefore, cells were also sprayed from media supplemented with gelatin to increase viscosity and help protect the cells from mechanical and chemical stresses. Viability was recovered, yet the mechanical integrity of the PEUU matrices was disrupted because of gelation within the fiber network.

In contrast to pressurized spraying, electrospraying cells did not significantly affect cell viability or proliferation. This is consistent with reports by others that cells can survive exposure to high voltage electric fields (see, e.g., Nedovic V. A., Obradovic B., Poncelet D., Goosen M. F. A., Leskosek-Cukalovic O., Bugarski B., "Cell immobiliation by electrostatic droplet generation", Landbauforsch Volk 2002, (241) 11-17; Temple M. D., Bashari E., Lu J., Zong W. X., Thompson C. B., Pinto N. J., Monohar S. K., King R. C. Y., MacDiamid A. G., "Electrostatic transportation of living cells through air", Abstracts of Papers, 223 ACS National Meeting, Orlando, Fl., Apr. 7-11, 2002). Even in the presence of PEUU electrospinning, SMC viability was not reduced, perhaps because the positively charged electrospinning and electrospraying streams repelled each other and avoided exposing cells to solvent prior to deposition. Also, due to the relatively large electrospinning distance of 23 cm, PEUU fibers were likely free of solvent by the time they were deposited. Electrospraying from media supplemented with gelatin resulted in a greater number of viable cells compared to electrospraying from media without gelatin. However, the use of gelatin leads to reduced construct mechanical properties. Accordingly, in many cases electrospraying from media alone maybe a preferred cellular incorporation method.

The cells that may be incorporated on or into the bioerodibe matrix include stem cells, progenitor (precursor) cells, smooth muscle cells, skeletal myoblasts, myocardial cells, endothelial cells, endothelial progenitor cells, bone-marrow derived mesenchymal cells and genetically modified cells. In certain embodiments, the genetically modified cells are capable of expressing a therapeutic substance, such as a growth factor. Examples of suitable growth factors include angiogenic or neurotrophic factor, which optionally may be obtained using recombinant techniques. Non-limiting examples of growth factors include basic fibroblast growth factor (bFGF), acidic fibroblast growth factor (aFGF), vascular endothelial growth factor (VEGF), hepatocyte growth factor (HGF), insulin-like growth factors (IGF), transforming growth factor-beta pleiotrophin protein, midkine protein. In one preferred embodiment, the growth factor is IGF-1.

EXAMPLES

The autogenous saphenous vein remains the graft of choice for both coronary (500,000 annually) and peripheral (80,000 annually) arterial bypass procedures. Failure of AVGs remains a major problem, and patients with failed grafts will die or require re-operation. IH accounts for 20% to 40% of all AVG failures. It is believed that IH is triggered by abrupt exposure of AVGs to the harsh new biomechanical environment of the arterial circulation and the elevated levels of CWS associated with the arterial system (140-fold increase compared to native venous conditions). The working hypothesis herein is that the IH response may be reduced or eliminated by more gradually exposing AVGs to arterial levels of CWS. That is, if an AVG is given an ample opportunity to adapt and remodel to the stresses of its new environment, cellular injury may be reduced, thus limiting the initiating mechanisms of IH. Clearly, developing a reliable means to prevent the early events of the IH process would contribute significantly to improvements in the clinical outcome of arterial bypass procedures. Therefore, the long-term goal of this work is to develop a new mechanical conditioning paradigm, in the form of a peri-adventitially placed, biodegradable polymer wrap, to safely and functionally "arterialize" AVGs in situ. The polymer wrap is tuned so that as it degrades over a desired period of time, the mechanical support offered by it is reduced and the vein is exposed to gradually increasing levels of CWS in situ.

Several of the molecular signals outlined herein, and the rationale for selecting them as endpoints for this study, are summarized in Table 1.

TABLE 1

Summary of and rationale for the chosen endpoints in this study.

| Proposed endpoints in this study | Role in IH | Rationale supported by the literature |
|---|---|---|
| Golgi Complex | Phenotypic modulation Protein Synthesis | Increased quantities in synthetic vs. contractile SMCs[a]. |
| PCNA | Proliferation | Increased cell proliferation in abruptly-exposed AVGs[b]. |
| TUNEL | Apoptosis | Altered apoptosis in abruptly-exposed AVGs[c] |
| Compliance | Clinical Performance | Important predictor of AVG patency[d] Compliance decreases in abruptly-exposed arterialized AVGs, thereby increasing compliance mismatch |
| Stiffness | Clinical Performance | Important predictor of AVG patency[d] Stiffness decreases in abruptly-exposed arterialized AVGs and could contribute to reduced clinical performance[e] |

[a]Morisaki N, et al. Cell cycle-dependent inhibition of DNA synthesis by prostaglandin i2 in cultured rabbit aortic smooth muscle cells. Atherosclerosis. 1988; 71(2-3): 165-71; Campbell G R, et al. Arterial smooth muscle. A multifunctional mesenchymal cell. Arch Pathol Lab Med. 1988; 112(10): 977-86; and Nagai R, et al. Identification of two types of smooth muscle myosin heavy chain isoforms by cdna cloning and immunoblot analysis. The Journal of Biological Chemistry. 1989; 264(17): 9734-7.
[b]Nishibe T, et al. Induction of angiotensin converting enzyme in neointima after intravascular stent placement. Int Angiol. 2002; 21(3): 250-5 and Zuckerbraun B S, et al. Overexpression of mutated ikappabalpha inhibits vascular smooth muscle cell proliferation and intimal hyperplasia formation. J Vasc Surg. 2003; 38(4): 812-9.
[c]Wang G J, et al. Regulation of vein graft hyperplasia by survivin, an inhibitor of apoptosis protein. Arterioscler Thromb Vasc Biol. 2005; 25(10): 2081-7 and Wang A Y, et al. Expression of apoptosis-related proteins and structural features of cell death in explanted aortocoronary saphenous vein bypass grafts. Cardiovasc Surg. 2001; 9(4): 319-28.
[d]Davies A H, et al. Prevention of malalignment during non-reversed femorodistal bypass. Ann R Coll Surg Engl. 1992; 74(6): 434-5.
[e]Jacot J G, et al. Early adaptation of human lower extremity vein grafts: Wall stiffness changes accompany geometric remodeling. J Vasc Surg. 2004; 39(3): 547-55.
[f]Tai N R, et al. Compliance properties of conduits used in vascular reconstruction. Br J Surg. 2000; 87(11): 1516-24 and Jacot J G, J Vasc Surg. 2004; 39(3): 547-55.

Example 1

Fabrication of PEUU Structures

By syringe pump into a stainless-steel capillary suspended 13-cm vertically over a 4.5" diameter aluminum mandrel 5-% wt. PEUU solution in hexafluoroisopropanol (HFIP) was fed at 1.0 mL/h. PEUU was charged with +12 kV and the aluminum target with −7 kV using high voltage generators (Gamma High Voltage Research). Aligned PEUU fibers were formed by electrospinning onto the target rotating at speeds ranging from 0.0 to 13.8 n/s. Scaffolds were allowed to dry overnight at room temperature and then placed under vacuum for 48 h at 30° C. A portion of each sample was mounted into a standard X-ray diffraction holder for analysis so that the fiber orientation was parallel to the X-ray beam. The samples were run on a PANalytical X'Pert Pro diffractometer using copper radiation. PEUU number average and weight average molecular weight were 228,700 and 87,600, respectively, resulting in a polydispersity index of 2.61. DSC demonstrated a glass transition temperature of −54.6° C. and a melt temperature of the PEUU soft segment at 41.0° C.

Electrospun Tubular Constructs for Blood Vessel Tissue Engineering

This example describes one method of producing a highly cellularized blood vessel construct that is capable of also providing substantial elastomeric mechanical support. The method involves a micro-integrated approach wherein a meshwork of submicron elastomeric fibers is built into a vessel wall with or without the cellular placement process. Cellularity can be developed through in vitro culture methods or in vivo. These methods are applicable to the coating of tubular tissues as described herein.

This example provides a method to luminally surface seed small diameter electrospun polyurethane conduits that may be used for coating tubular tissues as described herein. Electrospinning technology is used to incorporate cells during scaffold fabrication to better encourage tissue development.

Poly(ester urethane) urea was synthesized from poly(ε-caprolactone)diol and 1,4-diisocyanatobutane with putrescine chain extension. PEUU was dissolved at 6% wt. in hexafluoroisopropanol and electrospun. Electrospinning conditions included a solution volumetric flowrate of 1.0 mL/hr, a distance between nozzle and target of 13.5 cm, and voltages of +12 kV to the nozzle and −3 kV to the target. The target used for fabrication of small diameter tubes for implantation was a Type 316 stainless steel mandrel of 1.3 mm diameter that was rotating at 250 rpm.

The mandrel was also translating along its axis 8 cm on a linear stage at a speed of approximately 8 cm/s to produce a more uniform conduit thickness. Samples were electrospun for 15 min to produce porous tubular constructs with wall thicknesses on the order of 150 to 200 μm. For endothelialization studies a 4.7 mm stainless mandrel was instead utilized with the same process conditions.

PEUU at 6% wt. in HFIP was electrospun onto a negatively charged rotating mandrel at 250 rpm to produce a tubular construct. The electrospun tubes possessed 1.3 mm inner diameters, lengths up to 8 cm and wall thicknesses of 150-200 μm. Fiber sizes approximately in the range of 1000 μm were. In addition, these constructs were suturable and retained their lumens.

After fabrication, the mandrel was dipped in 70% ethanol in order to more easily remove it from the steel mandrel. The conduit was then rinsed in deionized water multiple times, blotted dry and then dried under vacuum at room temperature 24 to 48 h. Conduits were then examined for their gross structure with a dissecting microscope or their fibrous morphologies with scanning electron microscopy. In order to view an uninterrupted fibrous cross-section, samples were dipped in liquid $N_2$ for 1 min and then fractured before sputter-coating for SEM.

PEUU conduits (4.7 mm) were positioned inside a custom designed rotational vacuum seeding device and seeded with $20 \times 10^6$ musclederived stem cells (MDSCs). More specifically, the electrospun conduit was placed on metal stubs and a light vacuum was applied to the exterior of the conduit. Subcultured MSDCs were then perfused through the lumen of the conduit and forced into the fibrous lumen side wall of the tube by vacuum. Constructs were cultured under static conditions in Petri dishes for 24 h. After 24 h of static culture, cells were viable, adhered to the lumen and formed a monolayer.

Porous 1.3 mm inner diameter tubular electrospun scaffolds were implanted as interposition grafts in the abdominal aorta of rats. Constructs were suturable and easily retained their lumens in vivo. Female Lewis rats weighing 250-300 g were anesthetized with 1% isoflurane and 2.5 2.5 mg/100 g ketamine. A mid-abdominal incision was performed and the retroperitoneal cavity exposed. The descending aorta below renal level was dissected, clamped proximally and distally sectioned to make a 1 cm gap. The electrospun conduit was then implanted in an end-to-end manner using 10.0 prolene sutures. Intravenous heparin was administered before clamping with 200 Units/kg. The abdominal wall was closed in two layers with 2.0 Vycril sutures. Rats were able to recover from the surgeries with limb function. Rats were sacrificed at 2 wks and sample explants fixed in 10% neutral buffered formalin at room temperature. At 2 wks after implantation, grafts remained patent and functional. Samples were then embedded in paraffin and sectioned before staining with Hematoxylin and Eosin or Masson's Trichrome. Hematoxylin and eosin staining demonstrated external capsule formation around the explanted grafts. Masson's Trichrome staining indicated the capsule was composed of aligned collagen together with the presence of newly developed capillary vessels. Cell and tissue in-growth was observed throughout the constructs with the presence of collagen development. Cells were also demonstrated to have formed a monolayer in locations around the construct lumens.

Whereas the previous example provided in vivo approach, a biodegradable and cytocompatible, elastomeric poly(ester urethane) urea was electro spun into small diameter tubes appropriate for implantation in a rat model.

Like the previous example, this example provides methods for fabricating a highly cellularized blood vessel construct that also provides substantial elastomeric mechanical support. However, the previous model was an in vivo approach in a biodegradable and cytocompatible, elastomeric poly(ester urethane) urea was electro spun into small diameter tubes appropriate for implantation in a rat model. This example provides an in vitro approach, wherein SMCs were seeded into electrospun nanofibers concurrently with scaffold fabrication using a microintegration technique.

Vascular smooth muscle cells (SMCs) isolated from rat aortas were expanded on tissue culture polystyrene (TCPS) culture plates under Dulbecco's Modified Eagle Medium (DMEM) supplemented with 10% fetal bovine serum and 1% penicillin-streptomycin. Microintegration was performed similar to described previously with some modifications to allow for a smaller diameter electrospraying/electro spinning mandrel.

Figure 1:
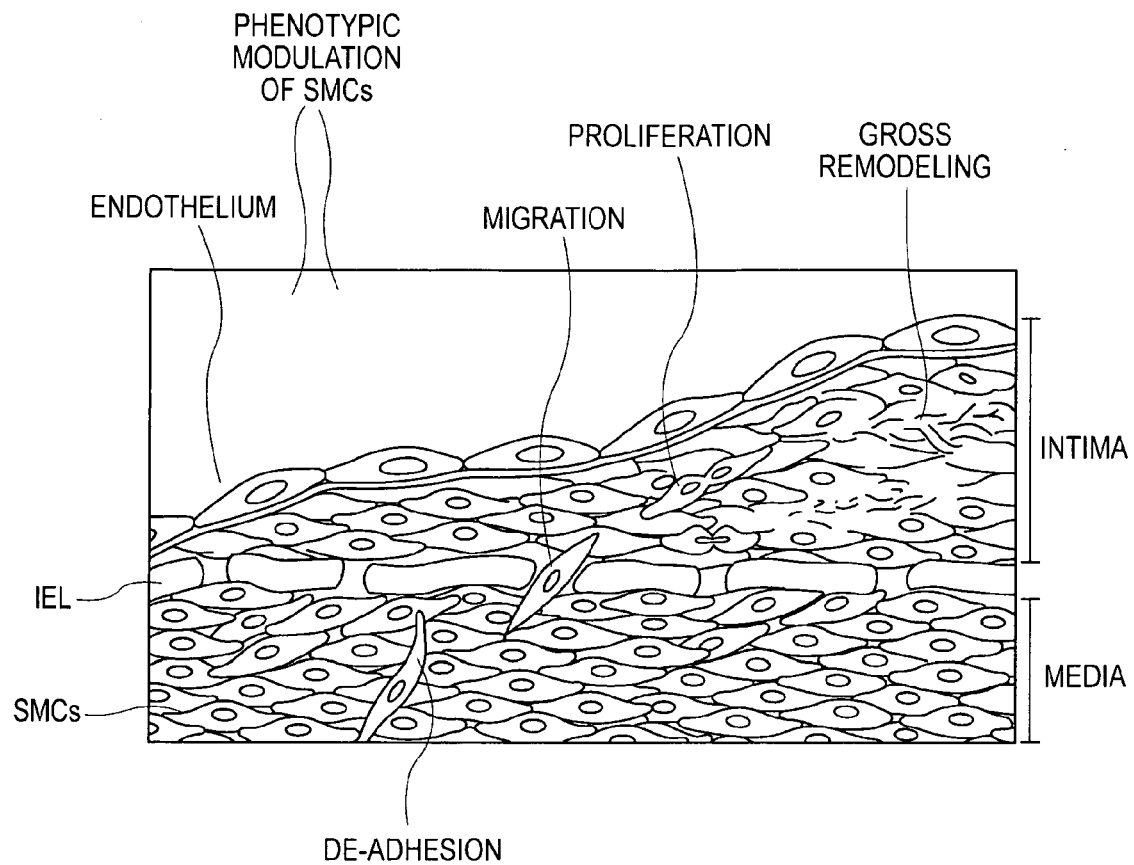
FIG. 1: Schematic of intimal hyperplasia progression. Please note: IEL, internal elastic lamina; SMCs, smooth muscle cells. Image adapted from Robbins Pathologic Basis of Disease, 1999 (Kumar V, Fausto N, and Abbas A. Robbins & coltran pathologic basis of disease. Saunders. 2004).
Figure 2:
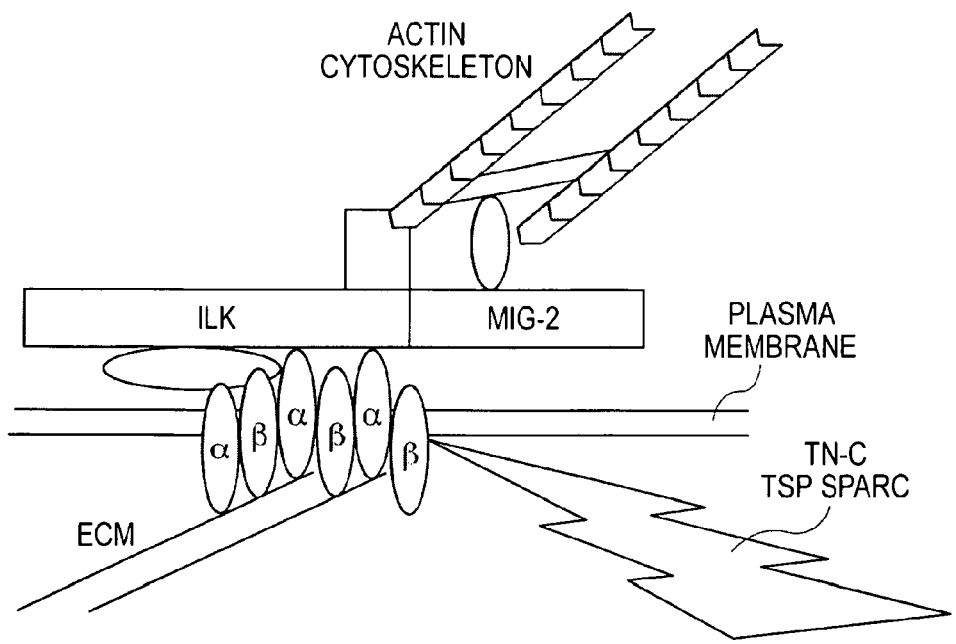
FIG. 2: Schematic showing the localization of Tenascin-C (TN-C), thrombospondin-1,2 (TSP), secreted protein acidic and rich in cysteine (SPARC), mitogen inducible gene 2 (Mig-2) and integrin linked kinase (ILK). Please note: ECM, extracellular matrix; .alpha. and .beta., integrins.
Figure 3:
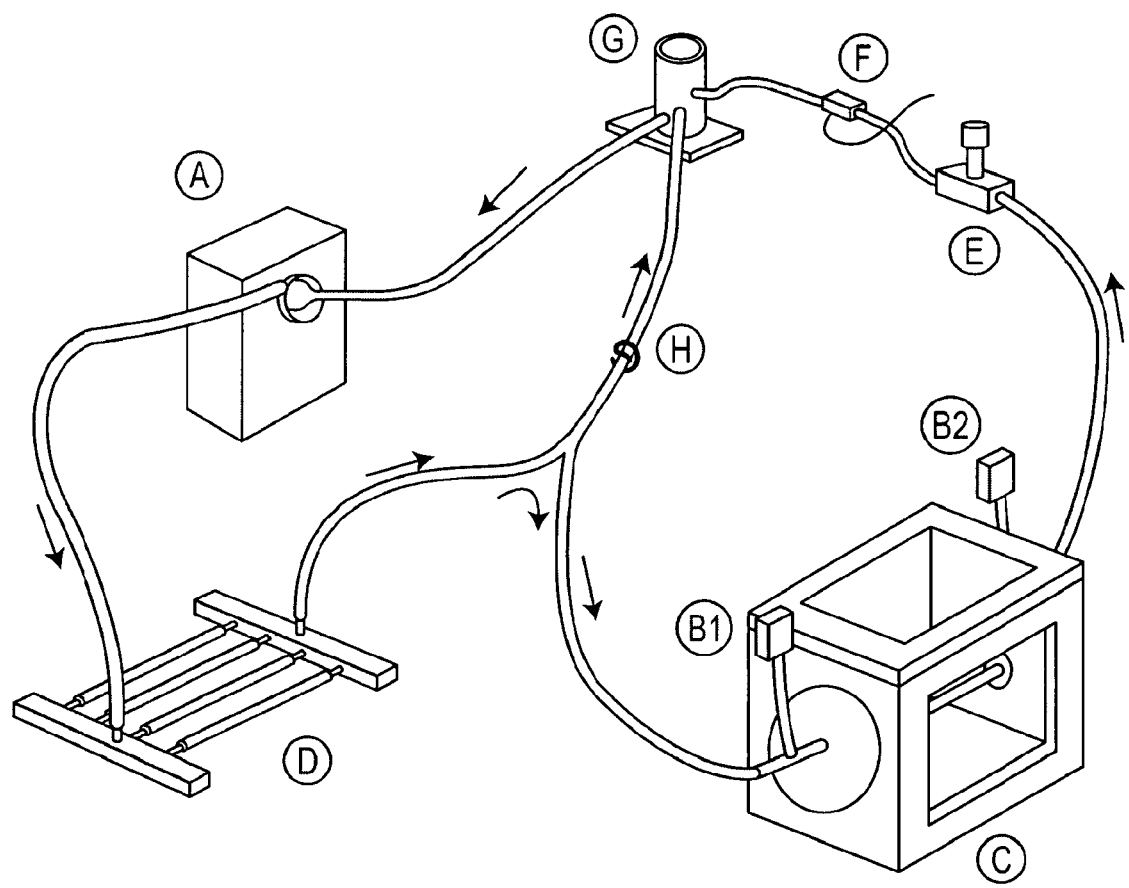
FIG. 3: Schematic of one of closed-loop perfusion/organ culture system. The loop is composed of a Biomedicus centrifugal pump that provides pulsatile pressure and flow (A), a heat exchanger (D), a tissue-housing chamber (C), proximal (B1) and distal (B2) pressure transducers, a variable resistance valve (E), flow probe (F), collection reservoir (G), and vessel bypass (H). Components not shown include, adventitial bath loop, He—Ne laser micrometer, and data acquisition system. See, Labadie (1996) et al. for more detail (Labadie, R. F., J. F. Antaki, J. L. Williams, S. Katyal, J. Ligush, S. C. Watkins, S. M. Pham, and H. S. Borovetz, "Pulsatile perfusion system for ex vivo investigation of biochemical pathways in intact vascular tissue", American Journal of Physiology, 1996. 270(2 Pt 2): p. H760-8).

$7.5 \times 10^6$ SMCs/mL were subcultured in medium and fed at 0.11 mL/min into a sterile Type 316 stainless steel capillary charged at 8.5 kV and located 4.5 cm from the target. 6% wt. PEUU or 6% wt. PEUU/collagen (75/25) in HFIP was fed at 1.5 mL/min into a capillary charged at 12 kV and located 23 cm from the target. The target consisted of a sterile stainless steel mandrel (4.7 mm diameter) charged at −3 kV and rotating at 250 rpm while translating 8-cm along its axis at 1.6 mm/s. A fabrication time of 30 min was used to produce each microintegrated conduit. After fabrication the conduit and mandrel were gently placed with aseptic technique into a roller bottle and cultured statically for 16 h. After 16 h, samples were gently removed from the mandrel for culture. Samples were then cut into 15 mm lengths and sutured to metal stubs and perfused media with pulsatile flow for 3 days in device substantially as shown in FIG. 3.

At timepoints of 1 day and 4 days after fabrication, samples were characterized. A MTT mitochondrial assay was used to measure cell viability. For histological investigation, samples were fixed in 10% neutral buffered formalin at room temperature. Samples were then embedded in paraffin, sectioned and stained with hematoxylin and eosin. Samples were analyzed for their biomechanical properties immediately after fabrication. Properties measured included ring strength, dynamic compliance, and burst pressure. In order to measure ring strength, stainless steel staples were inserted into 5 mm long tubular sections and then into the grips of a uniaxial tensile tester (ATS). Using a 10 lb load cell and a displacement rate of 10.05 mm/min samples were strained until break.

For dynamic compliance and burst strength, 15 mm long tubular samples were mounted in a flow loop driven by a centrifugal pump (Biomedicus) and submerged in PBS at 37° C. The pressure was monitored and recorded at 30 Hz using a standard in-line strain-gage pressure transducer and a PC acquisition board. The vessel construct was perfused with a pulsatile flow (110/70 mmHg, 1.2 Hz) and the dynamic compliance, C, was measured by recording the external diameter of the sample with a He—Ne laser micrometer (Beta Lasermike). Compliance was calculated as:

$$C = \frac{(OD_s - OD_d / OD_d)}{P_s - P_d}$$

for each pulse (D=maximum or minimum diameter, P=maximum or minimum pressure). A porcine mammary artery was used as a control for comparison with microintegrated PEUU in compliance studies. For measuring burst pressure, the sample outlet was sealed and flow was increased until tube rupture. The maximum pressure before rupture was taken as the burst pressure.

In order to extend the technology of cellular microintegration to small diameter tubes, a 4.7 mm diameter stainless steel mandrel was used in the place of the previously employed 19 mm diameter mandrel for sheet microintegration. In order to microintegrate highly cellular and defect free tubular constructs, it was useful to slightly decrease electrospraying distance 0.5 cm and lower the mandrel negative charge from −10 kV to −3 kV from previous methods. During fabrication, PEUU appeared pink and glistening on the mandrel indicative of uniform cellular electrospray. After removal from the mandrel, samples of either PEUU or PEUU/collagen (75/25) were found to be mechanically robust in that they were suturable and could retain their lumens after compression.

Cell placement and viability in the SMC micro integrated constructs was investigated initially and again after 4 days of static or perfusion culture. After perfusion, samples were gently removed from the stubs and then sectioned into representative slices for MTT and histology. MTT results indicated viable cells 1 day after fabrication. Furthermore, cells remained viable at day 4 with either static or perfusion culture with cell number values reported slightly higher for perfusion culture. Samples were fixed and stained with hematoxylin and eosin staining. H&E staining showed uniform initial cell integration within the tubular construct.

Ring strength, burst pressure, and suture retention strength were assessed in the micro integrated constructs after fabrication. Small tube sections (rings) were mechanically robust and flexible with maximum stress and strain values of 6.3 MPa and 170% respectively. The ring samples did not break cleanly in each case and seemed to pull apart or delaminate past the ultimate stress value. In order to calculate the dynamic compliance of the microintegrated constructs, samples were exposed to pulsatile flow and the pressure/diameter relationship was evaluated. This relationship was compared with a porcine mammary artery (pMA) exposed to the same pulsatile flow. The mechanical response of both the pMA and microintegrated PEUU was very similar with values falling for both samples falling between one another. Compliance values were $1.02\pm0.33\times10^{-3}$ $mmHg^{-1}$ for pMA and $0.71\pm0.13\times10^{-3}$ $mmHg^{-1}$ for SMC microintegrated PEUU. Burst pressure values for all samples were greater than 1500 mmHg. The burst pressure values were approximations due to the porous nature of the microintegrated tubes.

This method produced highly cellularized elastomeric scaffolds. Cells were viable after fabrication and proliferated under perfusion culture. In order to extend this technology to micro integrate cells into small diameter tubular constructs as a blood vessel prototype, it was advantageous to modify some process variables. For example, in order to target and electro spray cells onto the smaller diameter mandrel it was useful to decrease the distance between electro spray nozzle and mandrel. Also, it was useful to avoid a large negative bias on the mandrel. Using a high negative charge to the rotating mandrel target resulted in polymer protrusion defects, or "spikes" in the tube which could disrupt conduit integrity and cell viability. Therefore, it was useful to decrease mandrel charge to result in homogenously cellular and fibrous tubular conduits. These constructs were then cultured under a perfusion bioreactor to encourage better exchange of nutrients, waste, and oxygen to the cells in the tube interior. H&E and MTT results indicated viable cells present within the constructs after fabrication and perfusion culture.

Example 2

Changes in Mechanical Properties Due to Vein Graft Arterialization

Figure 4:
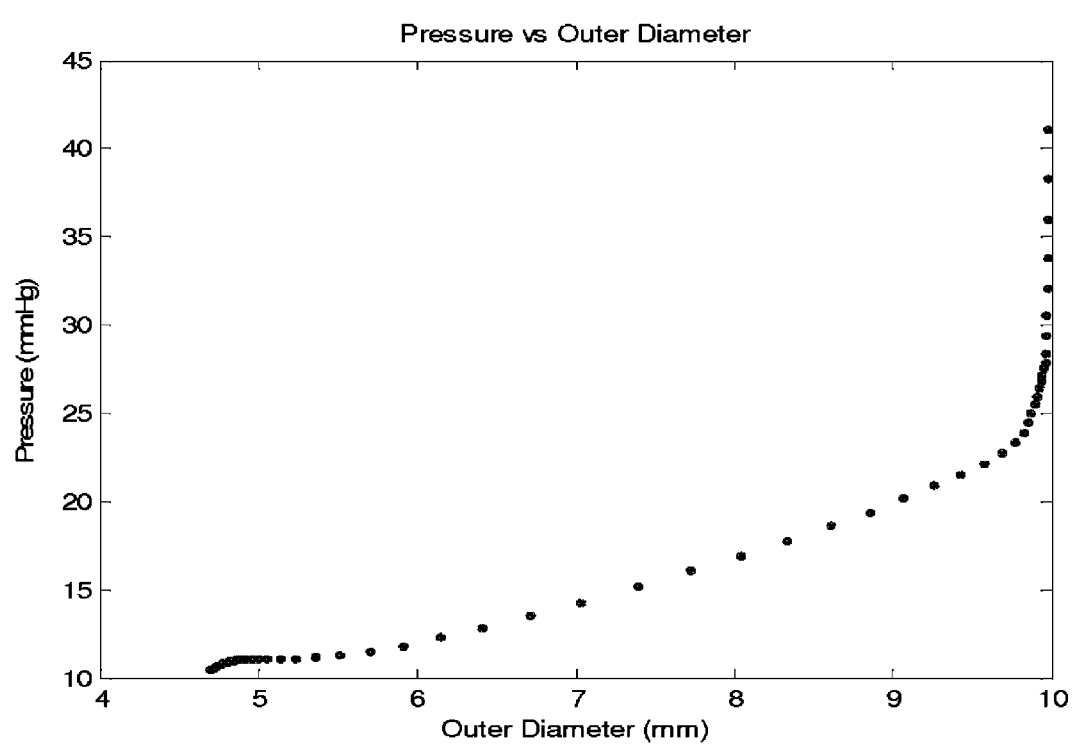
FIG. 4: Pressure vs. diameter response of a porcine internal jugular vein segment.

In the arterial pressure range an AVG is essentially a rigid tube due to the degree of its over distension (Stooker W, Gok M, Sipkema P, Niessen H W, Baidoshvili A, Westerhof N, Jansen E K, Wildevuur C R, and Eijsman L. Pressure-diameter relationship in the human greater saphenous vein. Ann Thorac Surg. 2003; 76(5): 1533-8). To confirm this we performed a pressure ramping experiment. The results of this experiment are shown in FIG. 4. It can be seen that the vein reaches maximum distension at approximately 30 mmHg. Consequently, at arterial levels of pressure a vein is very stiff, and we hope to counteract this phenomenon by providing temporary external structural support with a biodegradable adventitial wrap.

The degree of AVG distension is directly related to vein properties such as compliance, which, in turn, is related to patency rates according to Davies et al. (Davies A H, Magee T R, Baird R N, and Horrocks M. Prevention of malalignment during non-reversed femorodistal bypass. Ann R Coll Surg Engl. 1992; 74(6): 434-5 and Davies A H, Magee T R, Baird R N, Sheffield E, and Horrocks M. Pre-bypass morphological changes in vein grafts. Eur J Vasc Surg. 1993; 7(6): 642-7), who reported lower patency rates of less compliant AVGs in peripheral bypass surgery. This reduced patency has been largely attributed to compliance mismatch between the AVG and the native artery to which it is grafted (Bandyk D F and Mills J L. The failing graft: An evolving concept. Semin Vasc Surg. 1993; 6(2): 75-7; Bassiouny H S, White S, Glagov S, Choi E, Giddens D P, and Zarins C K. Anastomotic intimal hyperplasia: Mechanical injury or flow induced. J Vasc Surg. 1992; 15(4): 708-16; discussion 716-7; and Berkowitz H D, Fox A D, and Deaton D H. Reversed vein graft stenosis: Early diagnosis and management. J Vasc Surg. 1992; 15(1): 130-41; discussion 141-2). Veins are inherently less compliant than arteries (Tai N R, Salacinski H J, Edwards A, Hamilton G, and Seifalian A M. Compliance properties of conduits used in vascular reconstruction. Br J. Surg. 2000; 87(11): 1516-24) and become even less compliant upon abruptly exposed arterialization (Jacot J G, Abdullah I, Belkin M, Gerhard-Herman M, Gaccione P, Polak J F, Donaldson M C, Whittemore A D, and Conte M S. Early adaptation of human lower extremity vein grafts: Wall stiffness changes accompany geometric remodeling. J Vasc Surg. 2004; 39(3): 547-55). It appears as though change in AVG compliance is an important predictor of AVG failure.

Example 3

AVG Coated with a Restrictive Polymer Matrix

The data provided herein cover two distinct areas of ongoing research: i) investigation of the mechanopathobiological response of intact vein segments to arterial hemodynamics and ii) development of a biodegradable electrospun polymer for use as an adventitial wrap.

An ex vivo vascular perfusion apparatus was developed to study the responses of intact vascular segments and grafts to realistic, well-controlled biomechanical and metabolic conditions. FIG. 3 shows such a device. This device permits ex vivo exposure of porcine internal jugular vein segments to precisely controlled hemodynamics and dissolved gases (pH, $pO_2$, $pCO_2$) to simulate various conditions, including the venous and realistic AVG environment. Achieving these controlled conditions is accomplished using two independent perfusion/organ culture systems (shown schematically in FIG. 3). The closed loop perfusion design allows the circulation of sterile perfusate (tissue culture Media 199 supplemented with 1% fetal bovine serum, 0.5 g/liter Cefoxitin). A second roller pump circulates an adventitial bath (DMEM with 1% fetal bovine serum and 0.5 g/liter Cefoxitin) around the specimen, which is mounted in a sealed chamber.

To simulate native venous hemodynamics and biomechanics, the roller pump and flow resistors of the perfusion loop are set to provide nonpulsatile flow of 20 ml/min and pressure of 20 mmHg. To simulate AVG hemodynamics, the pump and flow resistors are set to provide a pulsatile pressure waveform of 120/80 mmHg and a mean perfusate flow of 100 ml/min. The "AVG conditioning" regimen will begin first by setting the perfusion system to provide arterial conditions as described above. The circumferential wall stress in a perfused vein segment will be controlled via the application of a tuned biodegradable perivascular electrospun polymer wrap. That is, the midvein-wall circumferential wall stress vs. time profile will involve the gradual imposition from venous (approximately 25 KPa) levels to arterial (approximately 140 KPa peak) levels, increasing linearly over a 24 or 192 hour period. Achieving this desired degradation rate would make in vivo mechanical conditioning of AVGs a possible treatment alternative perhaps improving patency rates in all AVGs.

Figure 5:
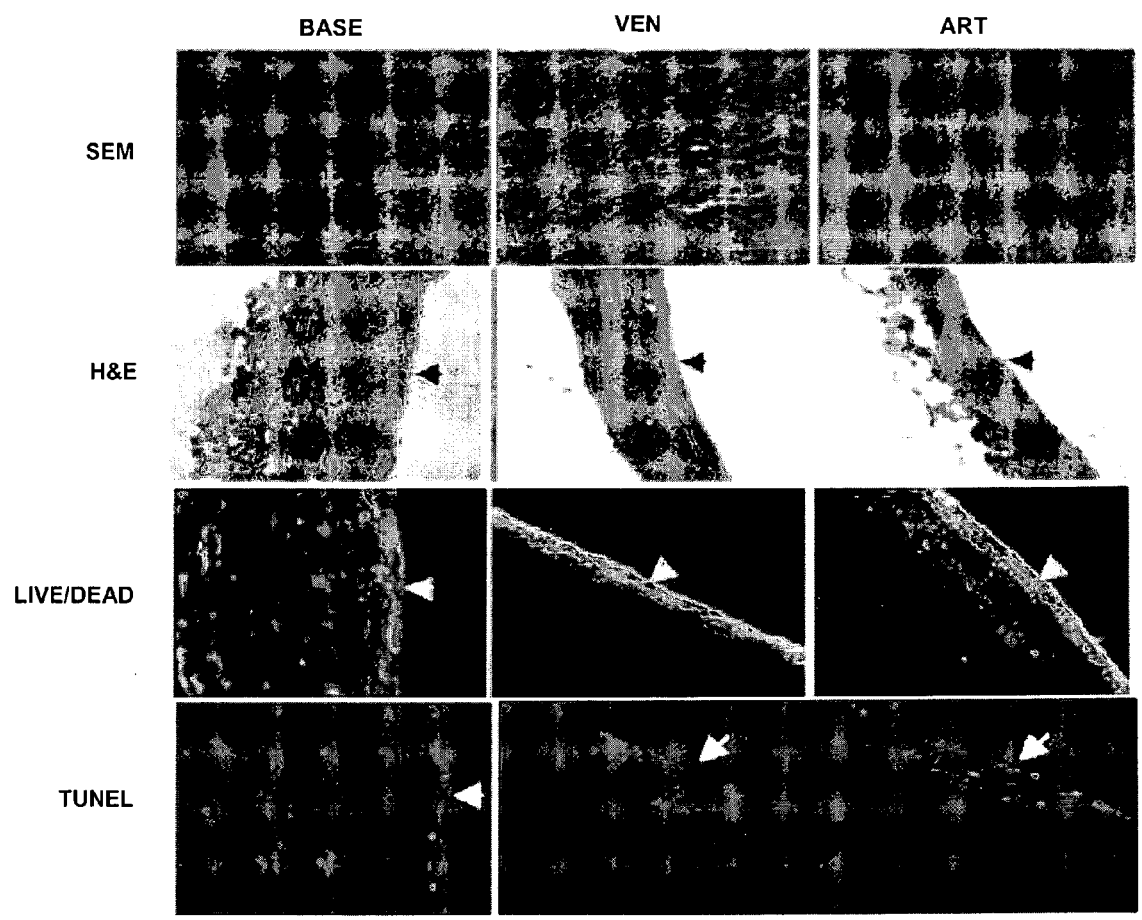
FIG. 5: The top three panels show representative scanning electron micrography images of the lumen of baseline control (BASE), "venous" 48 hour perfused control (venous), and "arterial" 48 hour perfused (arterial) porcine internal jugular vein segments. Note the cobblestone appearance of an intact endothelial cell layer. The second row of panels show representative microstructure and live nuclei via H&E staining of each group (200.times. magnification). The third row of panels show representative live (green in original) and dead (red in original) cells within each tissue group (200.times. magnification). Note that there does not appear to be an increased level of necrosis in perfused tissue when compared to BASE control tissue. The bottom three panels show representative TUNEL assay images of tissue from the same 48 hour perfusion experiment (400.times. magnification under immersion oil). Note that there does not appear to be an increased level of apoptosis in perfused tissue when compared to BASE. In all panels the arrow designates the vessel lumen.

To further validate ex vivo perfusion capabilities, tissue viability analysis of vein segments perfused under venous vs. arterial conditions was performed and the results to baseline level of tissue viability was compared. Scanning electron micrography, H&E staining, Live/Dead™ staining, and TUNEL analyses were performed after 48 hours of ex vivo perfusion (see FIG. 5). Scanning electron micrography and H&E staining indicated that the morphologic integrity of the tissue was intact after harvesting and after 48 hours of perfusion. Live/dead and TUNEL analyses showed no significant necrosis or apoptosis, respectively, in either the venous or arterial conditions when compared to baseline at 48 hours. Similar observations were made for perfusions lasting 14 days using an earlier generation of this system (Ligush, J., R. F. Labadie, S. A. Berceli, J. B. Ochoa, and H. S. Borovetz, Evaluation of endotheliumderived nitric oxide mediated vasodilation utilizing ex vivo perfusion of an intact vessel. The Journal of Surgical Research, 1992. 52(5): p. 416-21). These experiments demonstrate the ability to perform the proposed ex vivo porcine internal jugular vein perfusions, with maintenance of sterile conditions and tissue viability.

Figure 6:
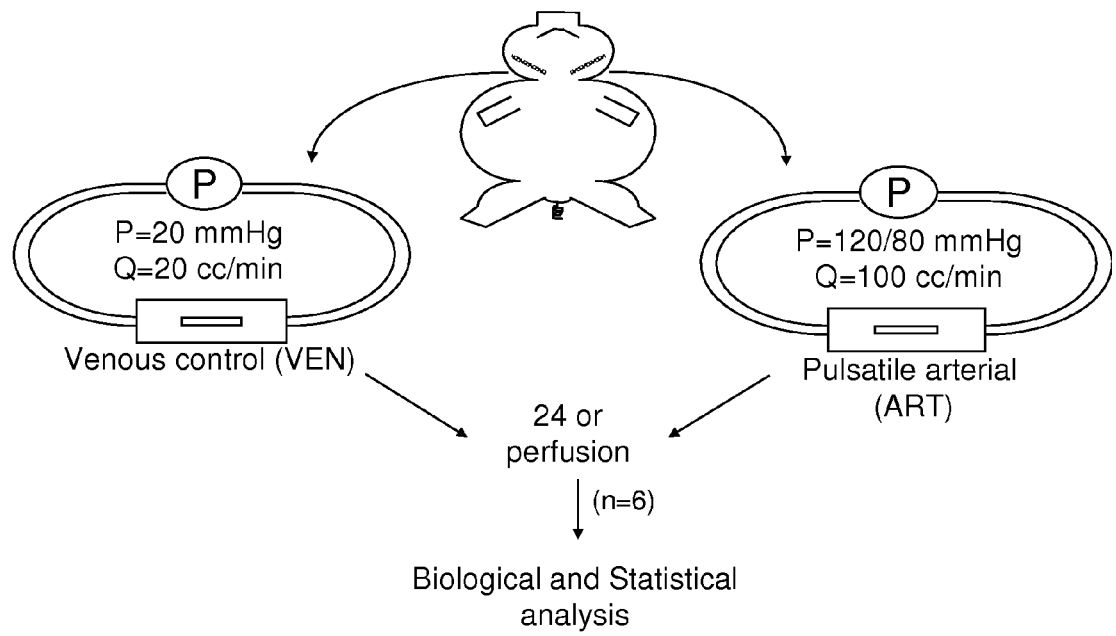
FIG. 6: Schematic depicting the VEN vs. ART ex vivo perfusion experiments.
Figure 7:
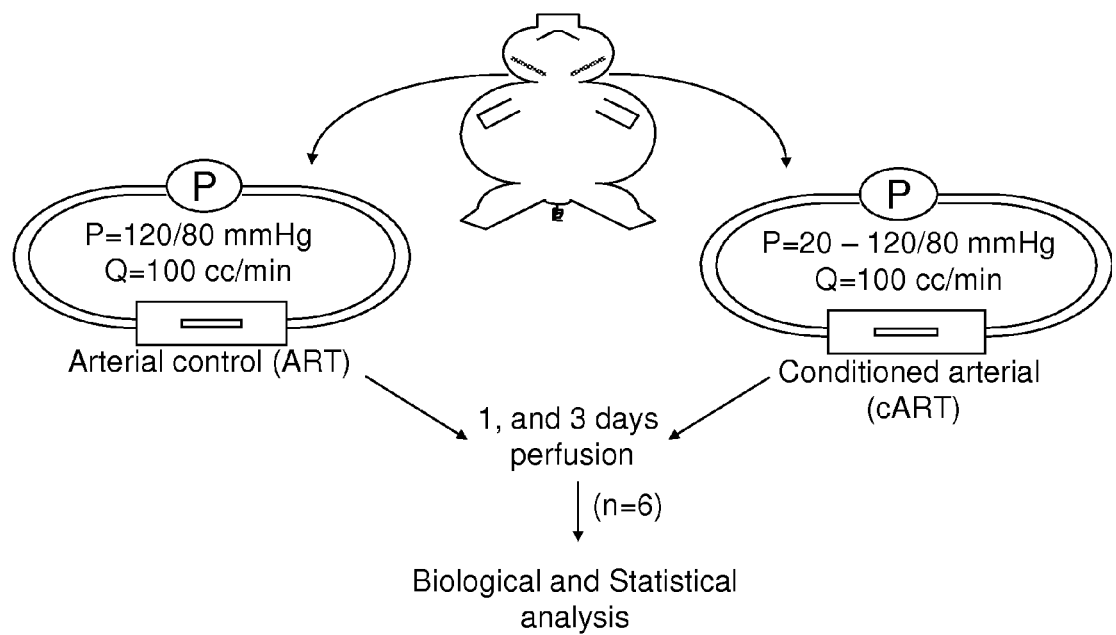
FIG. 7: Schematic depicting the ART vs. cART ex vivo perfusion experiments.
Figure 8:
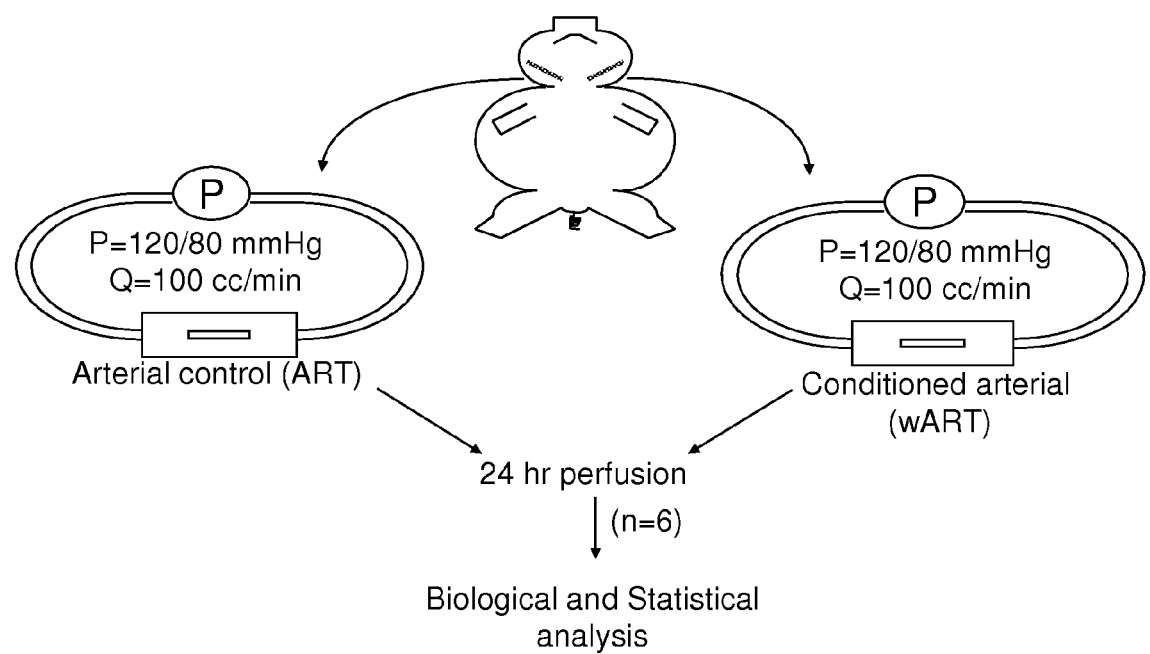
FIG. 8: Schematic depicting the ART vs. wART ex vivo perfusion experiments.

Several sets of ex vivo vascular perfusion experiments were performed. Initially, one set of experiments (N=6 animals per set) was performed to establish the acute hyperplastic response of PIJVs abruptly exposed to arterial biomechanical conditions, and to compare this response to PIJVs exposed to native venous conditions. FIG. 6 is a schematic showing this experimental design, which is also described in detail below. We then attempted to attenuate this acute hyperplastic response by gradually exposing porcine internal jugular vein segments (PIJVs) to desired CWS profiles via manual adjustment of validated ex vivo vascular perfusion system (EVPS) pressure. FIG. 7 is a schematic showing this experimental design which is also described in detail below. These experiments were directly related to establishing a CWS profile necessary to achieve a reduced acute hyperplastic response by freshly-excised vein segments perfused ex vivo under incrementally-imposed compared to abruptly-exposed arterial conditions. Using these results, we also wanted to tune the degradation rate of an adventitial biodegradable polymer wrap so as to achieve the same CWS profiles, and then to use this wrap to attenuate the acute hyperplastic response in PIJVs compared to unwrapped controls. FIG. 8 is a schematic showing this experimental design, which is also described in detail below. Each of the experiments described above was "paired" to account for animal-to-animal variability, and generally, proceeded as follows. Bilateral PIJVs were surgically harvested from juvenile pigs and tied into separate, independent EVPSs (see below). Vascular perfusion experiments were carried out for 24 or 72 hours since the majority of the endpoints under investigation have been successfully detected within a few hours of these time points (see references in Table 1, above). At the conclusion of each experiment, the tissue was processed (see below) for biological assays to assess the endpoints outlined in Table 1.

Tissue Harvest and Transport

The porcine internal jugular vein (PIJV) was chosen as a model because of its similarity in inner diameter and wall thickness to the human greater saphenous vein, and because this tissue has previously been used to investigate the pathologic response of veins exposed to arterial hemodynamic conditions. The surgical harvest procedure was performed in the manner of a saphenectomy for bypass. Briefly, the anesthetized animal was placed in supine position, cervical incisions were made bilaterally, and dissection was done in layers to the vascular fascia of the neck. Each PIJV was identified and dissected proximal to the jugular confluence and distal to the jugular foramen. All tributaries were identified and carefully ligated to avoid leakage. After the desired length (6-8 cm) was exposed, the segment was cannulated on each end with duck billed vessel cannulae. Just prior to explant, a custom-designed vascular clamp (Ligush J, Labadie R F, Berceli S A, Ochoa J B, and Borovetz H S. Evaluation of endothelium-derived nitric oxide mediated vasodilation utilizing ex vivo perfusion of an intact vessel. J Surg Res. 1992; 52(5): 416-21) was attached onto the ends of the cannulae to maintain the in vivo length of the vessel following removal. The vessel was then cut on either side between the clamped cannulae and the ligations. Immediately after removal, the vessels were placed in a sterile transport box (containing lactated ringers solution supplemented with heparin (500 units/liter), papaverine (60 mg/liter), and Cefoxitin (1.0 g/liter). The time between tissue harvest and mounting into the perfusion system described below was always less than one hour.

Perovascular Placement of Electrospun Biodegradable Polymer Wrap

The biodegradable polymer composite used to form the adventitial wrap was based on the poly(ester urethane)urea (PEUU) material developed by Guan et al. (Guan J, Sacks M S, Beckman E J, and Wagner W R. Synthesis, characterization, and cytocompatibility of elastomeric, biodegradable poly(ester-urethane)ureas based on poly(caprolactone) and putrescine. J Biomed Mater Res. 2002; 61(3): 493-503) and further characterized in electrospun format by Stankus et al. (Stankus J J, Guan J, and Wagner W R. Fabrication of biodegradable elastomeric scaffolds with sub-micron morphologies. J Biomed Mater Res A. 2004; 70(4): 603-14 and Stankus J J, Guan J, Fujimoto K, and Wagner W R. Microintegrating smooth muscle cells into a biodegradable, elastomeric fiber matrix. Biomaterials. 2006; 27(5): 735-44). This polymer undergoes hydrolytic degradation in vitro into non-cytotoxic degradation products and has been shown to degrade to near completion in vivo at approximately 3 months (Fujimoto K L, Guan J, Oshima H, Sakai T, and Wagner W R. In vivo evaluation of a porous, elastic, biodegradable patch for reconstructive cardiac procedures. Ann Thorac Surg. 2007; 83(2): 648-54 and Fujimoto K L, Tobita K, Merryman W D, Guan J, Momoi N, Stolz D B, Sacks M S, Keller B B, and Wagner W R. An elastic, biodegradable cardiac patch induces contractile smooth muscle and improves cardiac remodeling and function in subacute myocardial infarction. J Am Coll Cardiol. 2007; 49(23): 2292-300). To control the degradation rate of the wrap, a composite of PEUU, collagen, and elastin proteins was utilized, with protein addition used to hasten mass loss.

PEUU was synthesized from poly(ε-caprolactone)diol and 1,4-diisocyanatobutane with putrescine chain extension. PEUU, collagen, and elastin were combined in solution in 1,1,1,3,3,3-hexafluoro-2-propanol (HFIP), and then electrospun onto a PIJV segment using a procedure explained in detail elsewhere (Stankus J J, Guan J, and Wagner W R. Fabrication of biodegradable elastomeric scaffolds with submicron morphologies. J Biomed Mater Res A. 2004; 70(4): 603-14). Briefly, electrospinning conditions included a mixture solution volumetric flowrate of 0.28 µL/s, a distance between nozzle and target of 17 cm, and electrical charges of +12 kV to the nozzle and −3 kV to the target. The target used for fabrication of spun AVGs for implantation was a Type 316 stainless steel mandrel of 3 mm diameter that was carefully inserted into the AVG lumen to avoid endothelial injury. The mandrel and coaxial vein were rotated together at 250 rpm, and translated axially on a linear stage at a speed of approximately 8 cm/s over 10 cm to produce a more uniform coating thickness.

There were three parameters used to tune the mechanical properties and degradation rate of the polymer: 1) the final polymer concentration in a mixture solution; 2) the PEUU:collagen:elastin ratio in the mixture solution; and 3) the wrap thickness, which was proportional to electrospinning time. A summary of all tested combinations of these parameters is shown in Table 2.

TABLE 2

Summary of polymer tuning parameter combinations.

| Combination | PEUU:collagen:elastin % | Electrospinning Time (min) | Final Concentration (%) |
|---|---|---|---|
| A | 14.3:42.3:42.3 | 20 | 6 |
| B | 25:75:0 | 15 | 6 |
| C | 50:50:0 | 15 | 6 |
| D | 50:50:0 | 20 | 12 |

Ex vivo Perfusion Conditions

Vein segments were mounted in our well established, validated ex vivo vascular perfusion/organ culture system (EVPS, see, e.g., Labadie R F, Antaki J F, Williams J L, Katyal S, Ligush J, Watkins S C, Pham S M, and Borovetz H S. Pulsatile perfusion system for ex vivo investigation of biochemical pathways in intact vascular tissue. Am J. Physiol. 1996; 270(2 Pt 2): H760-8; Severyn D A, Muluk S C, and Vorp D A. The influence of hemodynamics and wall biomechanics on the thrombogenicity of vein segments perfused in vitro. J Surg Res. 2004; 121(1): 31-7 and Muluk S C, Vorp D A, Severyn D A, Gleixner S, Johnson P C, and Webster M W. Enhancement of tissue factor expression by vein segments exposed to coronary arterial hemodynamics. Journal of Vascular Surgery: Official Publication, the Society For Vascular Surgery [and] International Society For Cardiovascular Surgery, North American Chapter. 1998; 27(3): 521-7). Briefly, the closed loop perfusion design allows the circulation of sterile perfusate (tissue culture Media 199 supplemented with 1% fetal bovine serum and 1.0 g/liter cefoxitin) through the vascular segment as well as circulation of an adventitial bath (DMEM with 1% fetal bovine serum and 1.0 g/liter cefoxitin) within a sealed chamber. Both the perfusate and bathing media were maintained at 37° C. and physiologic levels of dissolved gasses. Experiments utilized one of two simulated hemodynamic conditions (Severyn D A, Muluk S C, and Vorp D A. The influence of hemodynamics and wall biomechanics on the thrombogenicity of vein segments perfused in vitro. J Surg Res. 2004; 121(1): 31-7 and Muluk S C, Vorp D A, Severyn D A, Gleixner S, Johnson P C, and Webster M W. Enhancement of tissue factor expression by vein segments exposed to coronary arterial hemodynamics. Journal of Vascular Surgery Official Publication, the Society For Vascular Surgery [and] International Society For Cardiovascular Surgery, North American Chapter. 1998; 27(3): 521-7)—either native venous (VEN) or arterial (ART) conditions. To simulate VEN hemodynamics the perfusion loop was set to provide nonpulsatile flow of 20 ml/min and pressure of 20 mmHg. To simulate ART hemodynamics, the system was set to provide a pulsatile pressure waveform of 120/80 mmHg with a mean perfusate flow of 100 ml/min. Separate experiments were performed to examine unwrapped veins under VEN or ART conditions, and wrapped veins under ART conditions (wART). Each perfusion experiment lasted for 24 hours with intraluminal pressure, outer diameter and flowrate being measured every hour. Vein segments were then analyzed either histologically or via immunohistochemistry as described below.

VEN vs. ART Experiments

FIG. 6 is a schematic depicting the first set of ex vivo experiments that were performed. In these experiments we evaluated the beneficial effects of a biodegradable electrospun polymer wrap on PIJVs the abrupt exposure of PIJVs to ART conditions vs. PIJVs exposed to VEN conditions for 24 hours.

ART vs. cART Experiments

FIG. 7 is a schematic depicting the second set of ex vivo experiments that were performed. In these experiments we evaluated the effects of a mechanical conditioning paradigm (cART conditions) on PIJVs vs. PIJVs abruptly exposed to ART conditions for 24 and 72 hours.

ART vs. wART Experiments

FIG. 8 is a schematic depicting the third set of ex vivo experiments that were performed. We evaluated the beneficial effects a tuned biodegradable polymer wrap on PIJVs to ART conditions (wART conditions) vs. unwrapped PIJVs exposed to ART conditions for 24 hours.

CWS Calculation in a Compound Cylinder

Since it is believed that an abrupt exposure of AVGs to arterial levels of CWS may contribute to their failure modalities, we believe that one potential application of the electrospun biodegradable polymer wrap would be to gradually expose AVGs to arterial levels of CWS. Previous attempts to limit CWS using an external sheath have not been fully successful because they were either biodurable and/or loose fitting. To demonstrate how the wrap may modulate CWS, and how the wrap may be tuned to achieve desired results, we examined the CWS-over-time profile for each of the wrap combinations given in Table 1 and compared these to unwrapped vein segments exposed to venous or arterial conditions. This was achieved using the data collected from ex vivo perfusion experiments and a mathematical model for CWS.

Figure 9:
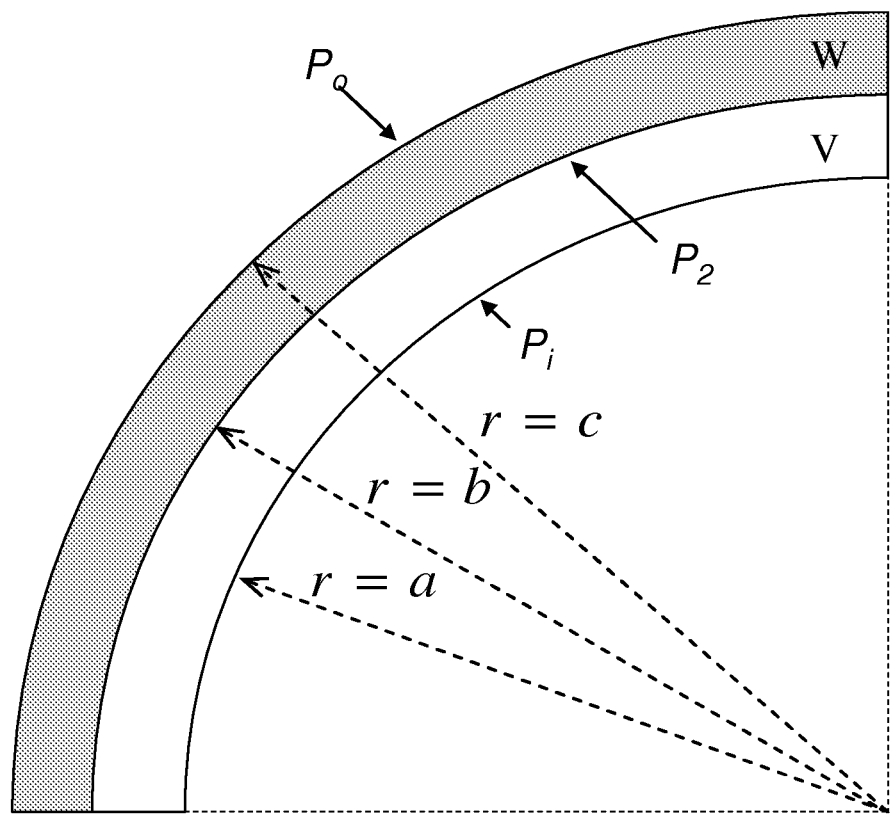
FIG. 9: Schematic showing a cross-sectional view of the vein/wrap complex.

For biomechanical modeling purposes, consider the schematic in FIG. 9 showing an idealized cross section of the vein/wrap complex. The outer layer of the bi-layer compound tube is taken as the electrospun polymer wrap and the concentric inner layer is the vein segment.

The following assumptions were then made (Vorp D A, Raghavan M L, Borovetz H S, Greisler H P, and Webster M W. Modeling the transmural stress distribution during healing of bioresorbable vascular prostheses. Ann Biomed Eng. 1995; 23(2): 178-88):

i) There is no slipping or detachment between layers
ii) Compatibility of deformation across the interface is maintained iii) There is only a small deformation under mean arterial pressure
iv) The system is under a state of plane stress
v) Both layers are incompressible, isotropic, homogeneous and linearly elastic materials vi) Each separate layer may be generalized as a single, thick-walled cylinder subjected to internal and external pressure The mathematical model developed by Vorp et al. (Id.) was adapted for the model represented by FIG. 9. In short, we used the classic Lame solution for radial and circumferential wall stresses ($\sigma_r$ and $\sigma_\theta$, respectively), and radial deformation ($u_r$) at any radius, r, in an open-ended, thick-walled cylinder under the action of internal and external pressures (Id.). For the inner (vein) layer shown in FIG. 9, we obtain (Id.):

$$\left. \begin{aligned} \sigma_{r,V} &= \frac{a^2 P_i - b^2 P_2}{b^2 - a^2} - \frac{(P_i - P_2)a^2 b^2}{(b^2 - a^2)r^2} \\ \sigma_{\theta,V} &= \frac{a^2 P_i - b^2 P_2}{b^2 - a^2} + \frac{(P_i - P_2)a^2 b^2}{(b^2 - a^2)r^2} \\ u_{r,V} &= \frac{1 - v_V}{E_V} \frac{(a^2 P_i - b^2 P_2)r}{b^2 - a^2} + \frac{1 + v_V}{E_V} \frac{(P_i - P_2)a^2 b^2}{(b^2 - a^2)r} \end{aligned} \right\} \text{ for } a \leq r \leq b$$

(15a)
(15b)
(15c)

where the "V" subscript refers to quantities with respect to the vein, and a and b are the inner and outer radii, respectively, of the vein layer. $P_i$ is the internal pressure, and $P_2$ is the interfacial pressure acting between the two layers of the concentric cylinder resulting from their difference in mechanical properties. V is the Poisson's ratio and E is the Young's modulus of elasticity. For the outer (wrap) layer shown in FIG. 9, we have:

$$\left. \begin{aligned} \sigma_{r,W} &= \frac{b^2 P_2 - c^2 P_o}{c^2 - b^2} - \frac{(P_2 - P_o)b^2 c^2}{(c^2 - b^2)r^2} \\ \sigma_{\theta,W} &= \frac{b^2 P_2 - c^2 P_o}{c^2 - b^2} + \frac{(P_2 - P_o)b^2 c^2}{(c^2 - b^2)r^2} \\ u_{r,W} &= \frac{1 - v_W}{E_W} \frac{(b^2 P_2 - c^2 P_o)r}{c^2 - b^2} + \frac{1 + v_W}{E_W} \frac{(P_2 - P_o)b^2 c^2}{(c^2 - b^2)r} \end{aligned} \right\} \text{ for } b \leq r \leq c$$

(17a)
(17b)
(18)

where the "W" subscript refers the quantities to the region occupied by the wrap, and b and c are the inner and outer radii, respectively, of the wrap layer. $P_o$ is the external pressure. With compatibility of deformations across the interface between the layers, it must be that:

$$u_{r,V} = u_{r,W} \text{ at } r=b \quad (19)$$

Substituting (16) and (18) into (19), letting vw=vv=v=0.5 (both materials assumed to be incompressible), setting $P_o$=0 (i.e., atmospheric pressure), and solving for $P_2$ we obtain:

$$P_2 = \frac{a^2 P_i(1-v)E_W b(c^2-b^2) + (1+v)E_W(c^2-b^2)ba^2 P_i}{b^2(1-v)E_W b(c^2-b^2) + (1-v)a^3 E_V(b^2-a^2) +} . \quad (20)$$
$$(1+v)E_W(c^2-b^2)ba^2 + c^2 E_V b(b^2-a^2)$$

Recall that $P_1$ and outer diameter (i.e., c) were measured in our ex vivo perfusion experiments. Therefore we had to estimate the inner (r=a) and interfacial (r=b) radii for each set of measured $P_1$ and c. Since we utilized the assumption that both the vein and wrap are incompressible materials, which requires the volume of each cylinder to be constant at any state of deformation, it must be that:

$$[\pi(r_o^2 - r_i^2)L]_u = [\pi(r_o^2 - r_i^2)L]_p \quad (21)$$

where $r_o$ and $r_i$ are the outer and inner radii, respectively, and L is the length of each cylinder, and the subscripts U and p refer to the unpressurized and pressurized states, respectively. Applying equation (21) to the geometry of the "wrap" cylinder in FIG. 9, yields:

$$b_p = \sqrt{\frac{c_p^2 L_p - (c_u^2 - b_u^2)L_u}{L_p}} . \quad (22)$$

Therefore for any measured $c_p$ and $L_p$, a value of $b_p$ can be calculated. Similarly, considering only the "vein" cylinder in FIG. 9 and utilizing equation (22) for $b_p$, we find:

$$a_p = \sqrt{\frac{\left(\frac{c_p^2 L_p (c_u^2 - b_u^2)L_u}{L_p}\right)L_p - (b_u^2 - a_u^2)L_u}{L_p}} . \quad (23)$$

Substituting equations (20), (22) and (23) into equation (1Sb), and evaluating at the mean arterial pressure and at $$r = \frac{a_p + b_p}{2}$$

we can calculate the mid-wall CWS in the polymer wrapped vein. We assumed that $E_w$=7.5 MPa (Stankus J J, Guan J, and Wagner W R. Fabrication of biodegradable elastomeric scaffolds with sub-micron morphologies. J Biomed Mater Res A. 2004; 70(4): 603-14), and $E_v$=600 KPa (Wesly R L, Vaishnav R N, Fuchs J C, Patel D J, and Greenfield J C.

Static linear and nonlinear elastic properties of normal and arterialized venous tissue in dog and man. Circulation Research (Online) 1975; 37(4): 509-20) in our calculations.

Vasomotor Challenge Experiments

To assess the effects of the electrospinning process on tissue viability we examined PIJV segments with ("spun") and without ("sham") the polymer wrap in place, as well as untreated freshly excised ("control") tissue. For the sham PIJV segments without the electrospun polymer wrap, we mimicked the electrospinning process up to the point of actually placing the polymer wrap (i.e., including the insertion of the mandrel and rotating/translating the vein within the electrical field). Tissue functionality was assessed using an ex vivo vasomotor challenge as previously described (Labadie R F, Antaki J F, Williams J L, Katyal S, Ligush J, Watkins S C, Pham S M, and Borovetz H S. Pulsatile perfusion system for ex vivo investigation of biochemical pathways in intact vascular tissue. Am J. Physiol. 1996; 270(2 Pt 2): H760-8 and Ligush J, Labadie R F, Berceli S A, Ochoa J B, and Borovetz H S. Evaluation of endothelium-derived nitric oxide mediated vasodilation utilizing ex vivo perfusion of an intact vessel. J Surg Res. 1992; 52(5): 416-21). In short, vessel segments were cannulated, placed under a constant intraluminal pressure of 20 mmHg, and exposed to incremental doses of epinephrine (EPI). Throughout the experiment, outer vessel diameter (D) was continuously measured with a laser micrometer (Labadie R F, Antaki J F, Williams J L, Katyal S, Ligush J, Watkins S C, Pham S M, and Borovetz H S. Pulsatile perfusion system for ex vivo investigation of biochemical pathways in intact vascular tissue. Am J. Physiol. 1996; 270(2 Pt 2): H760-8; Brant A M, Rodgers G J, and Borovetz H S. Measurement in vitro of pulsatile arterial diameter using a helium-neon laser. J Appl Physiol. 1987; 62(2): 679-83; and Ligush J, Labadie R F, Berceli S A, Ochoa J B, and Borovetz H S. Evaluation of endothelium-derived nitric oxide mediated vasodilation utilizing ex vivo perfusion of an intact vessel. J Surg Res. 1992; 52(5): 416-21). The baseline diameter ($D_{baseline}$) was measured before injection of the first dose of EPI. EPI was subsequently injected to final concentrations of $2\times10^{-5}$, $2\times10^{-4}$, and $2\times10^{-3}$ mg/ml at 1, 4.5, and 10 minutes, respectively. Following observation of maximal vasoconstriction with each dose, each subsequent dose was administered. After administration of the maximal dose of EPI, and observation of maximal level of constriction ($D_{constricted}$), a 2 ml bolus of 25 mg/ml sodium nitroprusside (SNP) was injected to give a final concentration of 0.125 mg/ml. When full dilation was observed, $D_{dilated}$ was recorded. The level of constriction in response to EPI was calculated as:

$$\% \text{ Constriction} = \frac{D_{baseline} - D_{constricted}}{D_{constricted}} * 100 \quad (24)$$

similarly, the level of dilation in response to SNP was calculated as:

$$\% \text{ Dilation} = \frac{D_{dilated} - D_{constricted}}{D_{constricted}} * 100. \quad (25)$$

Compliance and β-Stiffness Measurements

Hourly measurements of outer diameter (OD) and intraluminal pulsatile pressure (P) were made during the ART vs. wART 24-hour perfusion experiments (N=6) described above. These measurements were used to calculate the compliance (C) and β-stiffness (β) of both spun and sham control PIJVs. Using a sampling frequency of 150 Hz, the hourly measurements were made for 5 seconds so that approximately 5 complete "cardiac cycles" of data were collected. The acquired signals were then filtered and plotted. Using the maximum ($OD_s$ and $P_s$) and minimum ($OD_d$ and $P_d$) values for each cycle, equation 26 was used to calculate C and equation 27 was used to calculate β (Hayashi K. Experimental approaches on measuring the mechanical properties and constitutive laws of arterial walls. J Biomech Eng. 1993; 115(4B): 481-8). The 5 values were averaged and single values of C and β were calculated every hour.

$$C = \frac{(OD_s - OD_d / OD_d)}{P_s - P_d} \quad (26)$$

$$\beta = \frac{\ln(P_s - P_d)}{(OD_s - OD_d / OD_d)} \quad (27)$$

Post-Perfusion Tissue Processing

Figure 10:
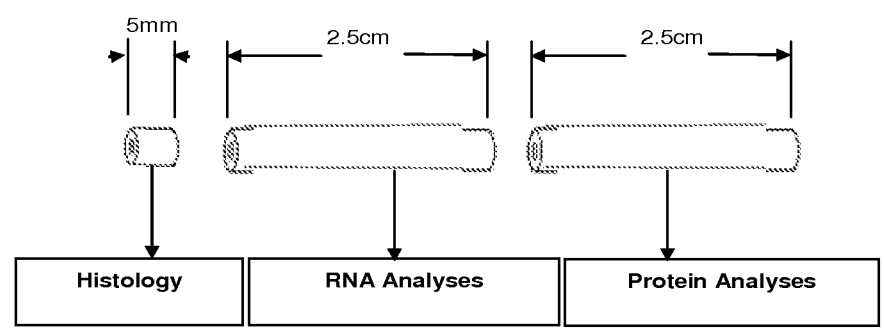
FIG. 10: Schematic of post perfusion venous segment processing for endpoint analysis. Lengths given represent unloaded vessel resting lengths.

We will evaluate endpoints from experiments of 1 day, and 3 days duration. We have established that maintenance of tissue viability is achievable for this perfusion duration when utilizing freshly excised vascular segments (Ligush J, Labadie R F, Berceli S A, Ochoa J B, and Borovetz H S. Evaluation of endothelium-derived nitric oxide mediated vasodilation utilizing ex vivo perfusion of an intact vessel. Surg Res. 1992; 52(5): 416-21). The hyperplastic response of the veins will be quantified by measuring the various carefully chosen endpoints summarized in Section 1.2. These endpoints can be grouped into three categories based on the required tissue processing: i) histology (including micro/ultrastructure); ii) RNA analysis; and iii) protein analysis. All vein segments were segmented and processed according to FIG. 10.

Biological Analysis

The biological endpoints proposed for above can be characterized as either histological or molecular-based with respect to the type of assay required. The histological endpoints included evaluation of microstructure, apoptosis, proliferation, a SMC phenotype marker, and a cell-adhesion marker. The protein and gene expression endpoints required isolation of protein and RNA and are classified as molecular.

The samples dedicated for histological analysis (FIG. 10) were taken from the freezer and immediately embedded in Tissue Freezing Medium™ (Triangle Biomedical Sciences, Durham, N.C.) and frozen at −65° C. Five-micron cross-sections were cut using a cryotome and placed on positively charged, glass microscope slides. Slides were stored at −80° C. until they could be processed for histological or immunohistochemical assays.

Histology

Following removal of the veins from the ex vivo perfusion system, they were fixed in 4% paraformaldehyde for 4 hours at 4° C. followed by 30% sucrose at 4° C. overnight. 5 mm tissue rings were cut, washed with PBS, embedded in Tissue Freezing Medium™ (Triangle Biomedical Sciences, Durham, N.C.), and cut into 5 μm sections. The tissue sections were either stained with hematoxylin and eosin (H&E), Masson's trichrome (MTC), picrosirius red, or Movat's pentachrome stains. Stained tissue sections were then visualized using an Olympus Provis light microscope (Olympus, Center Valley, Pa., USA) and compared qualitatively.

Scanning Electron Microscopy

The electrospun wrapped PIJVs were examined under scanning electron microscopy (SEM). In short, tissue segments designated for SEM were fixed in ultrapure 2.5% gluteraldehyde, dehydrated through a graded series of ethanol solutions (30-100%), critical point dried (Emscope, CPD 750, Ashford, Kent, UK), then overcoated with vaporized carbon (Cressington Freeze Fracture Device, Cressington, Cranberry, Pa., USA). The tissue was visualized using a JEOL JEM-6335F field emission gun SEM (JEOL, Peabody, Mass., USA).

Necrosis

To assess the effects of the electrospinning process on tissue viability we examined spun and sham PIJV segments, as well as untreated freshly excised ("control") tissue. Tissue necrosis was examined using Live/Dead™ staining (Molecular Probes, Carlsbad, Calif., USA) of cryosections, according to manufacturer's instructions. Each segment (control, sham control and spun) intended for Live/Dead™ staining was cut in half and placed in static culture within a Petri-dish under standard incubator conditions. One-half of each segment was assessed after 18 hours of culture, the other after 92 hours. 5 mm rings were cut from each sample and embedded in cryomatrix (TBS, Durham, N.C.) then frozen. Five 8 μm sections were cut from each ring and imaged under 20× magnification using an epifluorescent microscope (Nikon, Model E800, Melville, N.Y., USA). Two images were taken per section so that a total of 10 fields of view were quantified per PIJV segment. Scion Image (Version Beta 4.02, NIH, Bethesda, Md.) was used to count the total number of cells in a field of view. To determine the percentage of live cells in a field of view, dead cells were counted manually, divided by the total number of cells, and multiplied by 100%. The percentage of dead cells was subtracted from 100% to calculate the percentage of live cells.

Apoptosis

Apoptosis was assessed using the In Situ Cell Death Kit, fluorescein (TUNEL) (Roche Applied Science, Indianapolis, Ind.). This assay uses the TUNEL technology which identifies the genomic DNA cleavage component of apoptosis. Briefly, cross-sections were dried at 37° C. for 20 minutes, fixed in 4% paraformaldehyde for 20 minutes, and rehydrated in phosphate buffered saline (PBS) for 30 minutes. Samples were then incubated at room temperature for 10 minutes each in 10 μg/ml Proteinase K followed by a freshly prepared solution of 0.1% Triton X-100 and 0.1% sodium citrate for permeabilization of membranes. DNA strand breaks were identified by incubation at 37° C. for one hour with Terminal deoxynucleotidyl transferase and fluorescein labeled dUTP (both provided in the kit from Roche). Nuclei were counterstained with Hoechst 33258. A small set of samples was treated with 100 U/ml of DNase I to serve as positive controls each time the assay was performed to ensure efficacy. All sample preparation parameters including incubation times, temperatures, and reagent concentrations were optimized using DNase I treated positive controls. Negative controls were incubated with labeled dUTP without the transferase enzyme.

Quantification of the percent of TUNEL positive cells was performed using a manual counting procedure. Positive cells from each of 5 FOVs (field of views) from a given 5 μm cross-section were averaged to define the mean percent positive cells for that cross-section. The mean percent TUNEL positive cells from one segment (FIG. 10) was determined.

Proliferation

Proliferation was assessed by the expression of proliferating cell nuclear antigen (PCNA) determined by immunohistochemistry. Five-micron cross-sections were dried, fixed, and permeabilized as described for the TUNEL assay. Nonspecific binding of antibodies was blocked by incubating the samples for 15 minutes with 1% horse serum in PBS. Following this, the samples were incubated with a primary mouse monoclonal antibody against human PCNA (Dako Cytomation, Clone PC10, Denmark) overnight at 4° C. in a moist chamber to prevent sample drying. Unbound primary antibody was removed by subsequent washes in PBS. Next, cross-sections were incubated with a universal (anti-mouse and anti-rabbit) biotinylated secondary antibody which was part of the Vectastain Elite™ horse-radish perxidase and avidin-biotin detection system (Vector Labs, Cat.# PK-6200, Burlingame, Calif.) for 60 minutes at 37° C. in a moist chamber and then rinsed 3 times with PBS. Incubation with the Vectastain™ reagent was then performed for 30 minutes at room temperature. To detect positively stained cells, a diaminobenzidine (DAB) substrate (Vector Labs, Cat.# SK-4100, Burlingame, Calif.) was used. The enzymatic reaction caused PCNA positive cells to stain brown which was visualized via microscope (100× magnification) until the desired level of staining was achieved. The reaction was then stopped by placing the slides into deionized water. For nuclear visualization, cells were counter-stained with Hematoxylin (Vector Labs, Cat.# H-3401, Burlingame, Calif.) according to manufacturer's instructions. Quantification of the percent PCNA positive cells was performed using the same methodology as for TUNEL.

SMC Phenotype

To detect a synthetic SMC phenotype, we used a mouse monoclonal antibody rasied against human Golgi complex (Abcam, Cat.# ab14487, Cambridge, Mass.). The same procedure as described above (PCNA) was used to quantify the mean percentage of Golgi complex positive cells per segment of vein.

Statistics

For the vasomotor challenge data, and the immunohistochemistry image quantification data a paired student's t-test for means was performed, and $P<0.05$ was considered statistically significant. Unless otherwise stated all data is presented as mean±standard error of the mean.

Results

CWS Profiles

Figure 11:
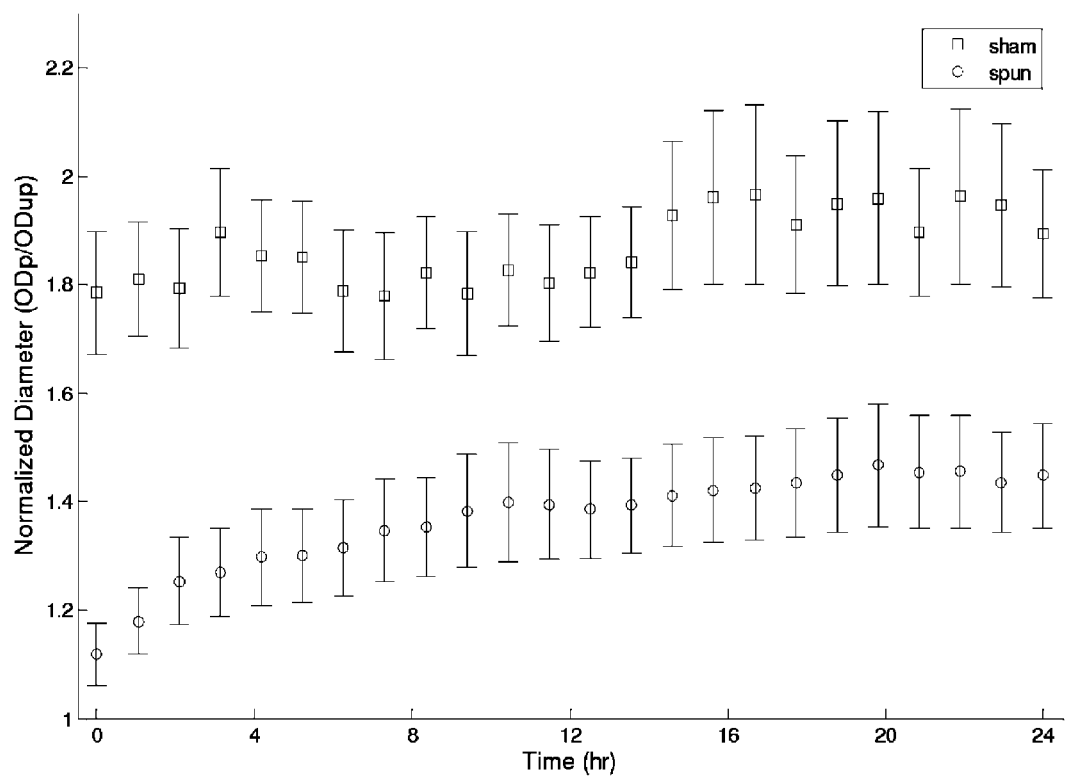
FIG. 11: Normalized outer diameter response of PIJVs for both sham and spun PIJVs. Both spun (wART) and sham control PIJVs were perfused under ART conditions of 120/80 mmHg pressure and 100 ml/min mean flowrate. Note that the normalized diameter of the spun veins (N=7) is dramatically reduced when compared to sham controls (N=5). Pressurized outer diameter (ODp) was normalized to unpressurized outer diameter (ODup) and data is shown as mean±standard error of the mean.

The structural support offered to a vein by the wrap is evident when we examine the outer diameter profiles in FIG. 11. It was shown that a vein with a wrap does not expand to the same degree under ART conditions as a vein without a wrap. The reduction in diameter effectively reduced the CWS in the vein wall vs. unwrapped controls under the same level of arterial pressure as described below.

Figure 12:
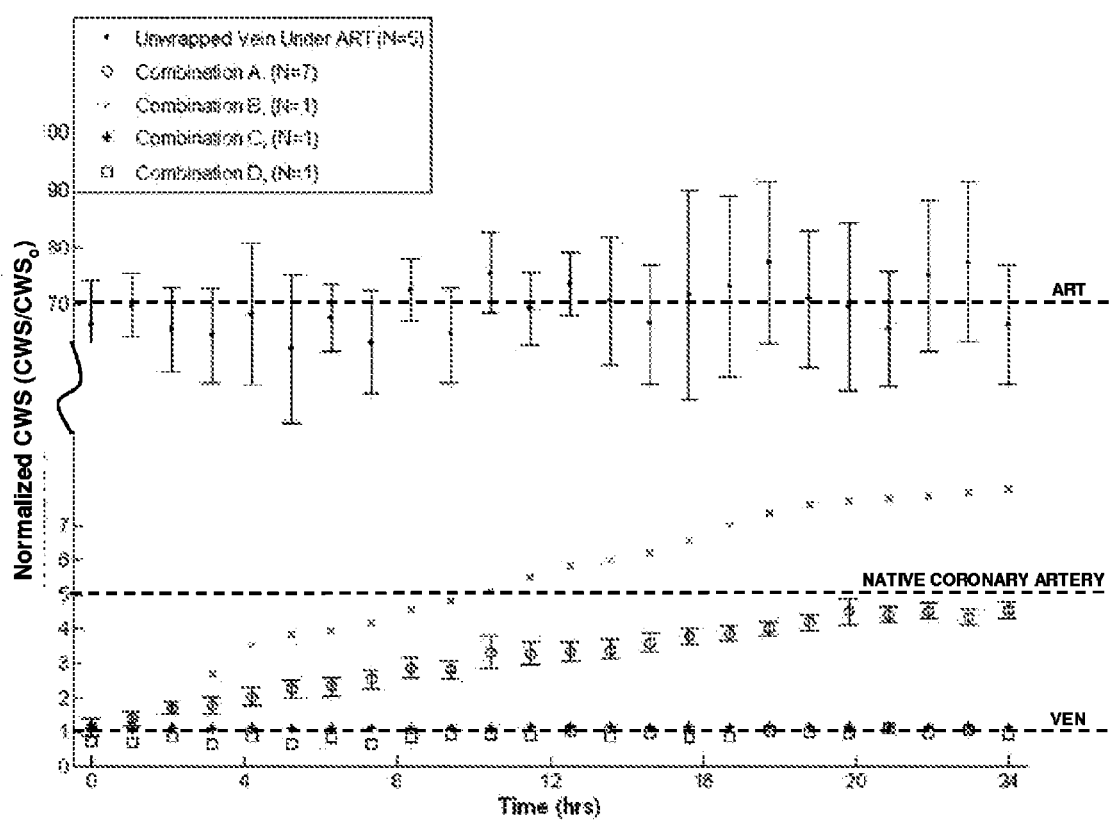
FIG. 12: CWS vs. time results from 24 hour ex vivo perfusions of electrospun polymer wrapped PIJV segments for each combination in Table 1. The lower dashed horizontal line indicates the mean CWS level measured in an unwrapped vein under venous conditions (CWSo .about.25 KPa), and the middle dashed horizontal line indicates the mean CWS in a coronary artery (.about.120 KPa) (Labadie R F, et al. Pulsatile perfusion system for ex vivo investigation of biochemical pathways in intact vascular tissue. Am J. Physiol. 1996; 270(2 Pt 2): H760-8). The upper dashed line represents the mean CWS measured in an unwrapped vein (sham control) under ART conditions. In the legend, ET stands for electrospinning time. All CWS values were normalized to CWS.sub.0. The data are presented as mean±standard error of the mean.

The CWS-over time profile for the polymer solution combinations of Table 2 were quite variable (FIG. 12). In one case (combination B), the wrap degraded too quickly and resulted in a rapid increase in CWS under ART conditions. Other combinations (C and D) did not degrade quickly enough and resulted in no appreciable increase in CWS over a 24-hour period. Combination A degraded at a rate which resulted in a nearly linear variation over the 24-hour period between VEN and ART levels of CWS. This combination was repeated (N=7) and the effect was found to be repeatable.

Vasomotor Challenge Results

Figure 13:
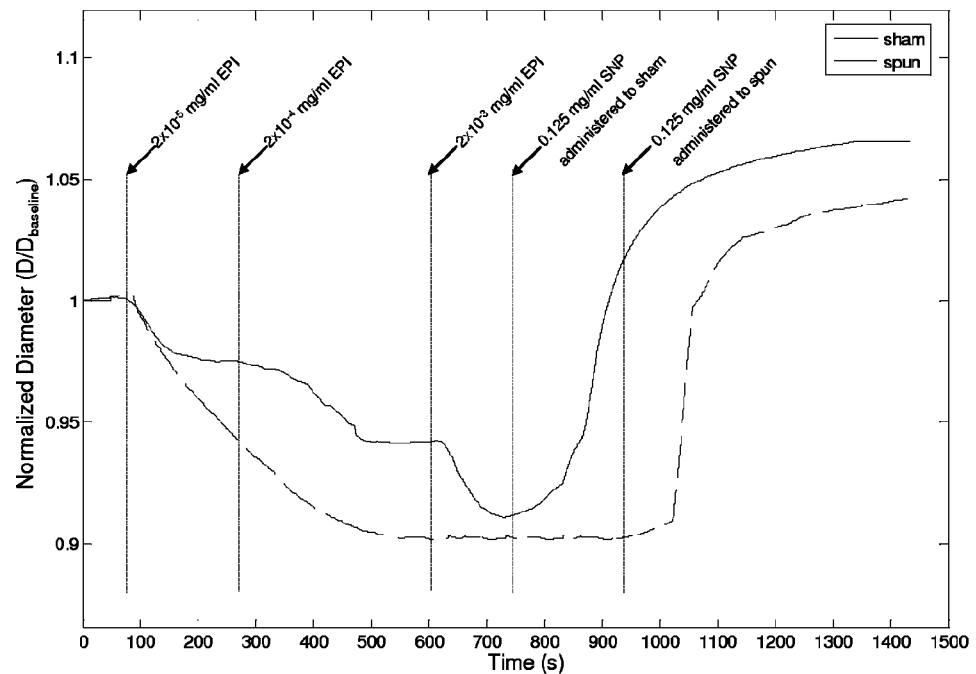
FIG. 13: Representative vasomotor challenge results obtained using epinephrine (EPI) and sodium nitroprus side (SNP) to stimulate both a spun and a sham control PIJV segment. Please note that SNP was administered immediately upon observing a natural relaxation of the tissue post-stimulation with EPI. That is, SNP was administered at different times for the sham and spun PIJVs, depending on when the natural relaxation of the tissue (post stimulation with EPI) was observed. Outer diameter measurements of each PIJV segment over the duration of the experiments were normalized to the baseline outer diameter which was measured prior to administration of the first dose of EPI.
Figure 14:
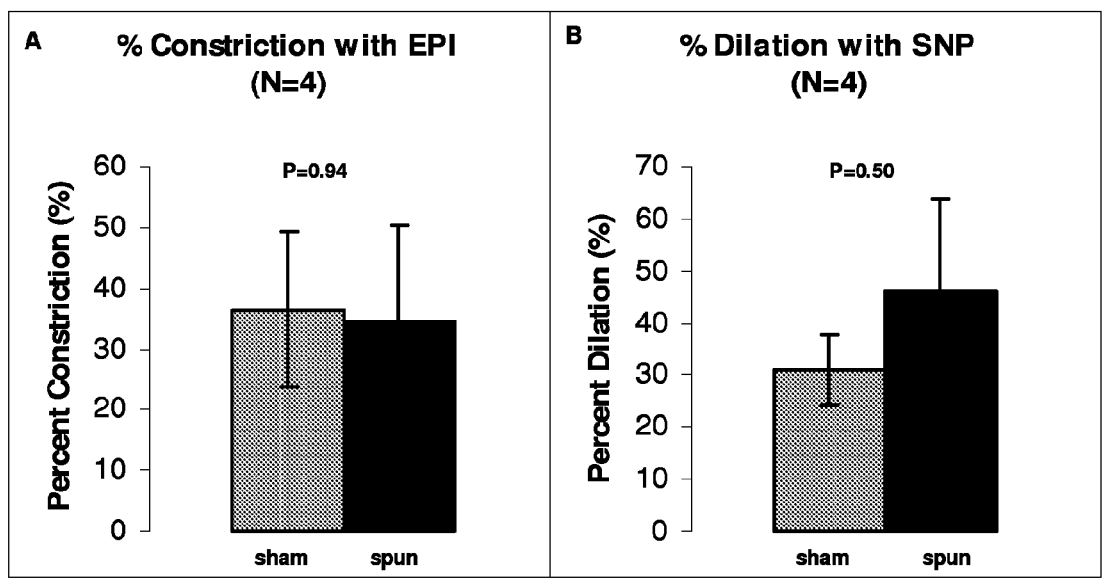
FIG. 14: Results from vasomotor challenge experiments (N=4). There appears to be no significant difference in the level of contraction or dilation between the sham control and spun PIJVs. The data are presented as mean±standard error of the mean.

The results of a typical vasomotor challenge experiment are shown in FIG. 13. The sham PIJV segment responded in a predictable dose-dependent manner to stimulation with EPI, while the spun PIJV exhibited a single contraction commencing with the lowest dose of EPI. Vasodilation in response to SNP was similar for both the control and spun PIJVs, each resulting in a larger outer diameter than that at baseline, suggesting a certain level of basal tone in both the sham and spun PIJVs. Overall, there was no significant difference in the level of contraction (FIG. 14A) or dilation (FIG. 14B) between sham and spun PIJV segments.

Compliance and β-Stiffness

Figure 15:
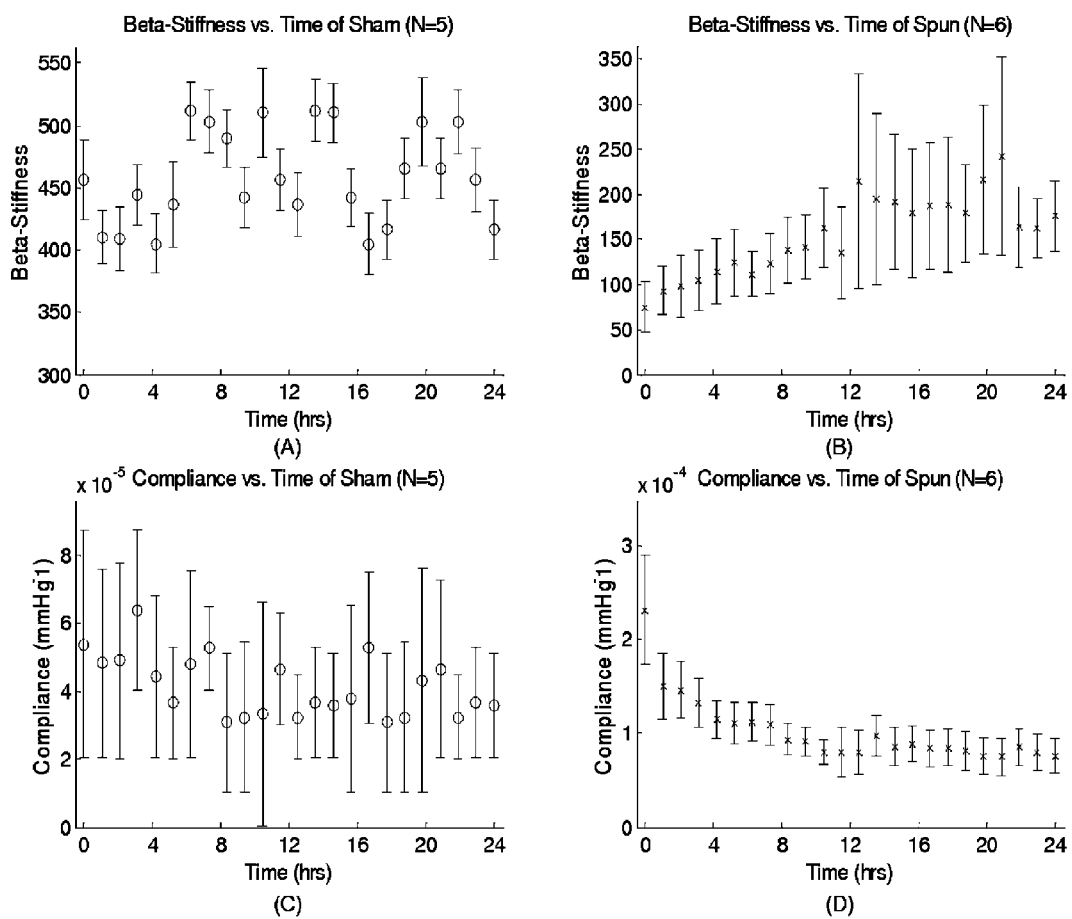
FIG. 15: Results from the compliance and .beta.-stiffness calculations for both sham (A & C) and spun (B & D) PIJVs over 24 hours. The data are presented as mean±standard error of the mean.

In FIGS. 15A and 15C, we see that PIJVs are very stiff (and hence much less compliant) when exposed to arterial levels of pressure. Under the same hemodynamic conditions, the tuned polymer wrap that was spun onto the adventitial surface of the PIJVs offered structural support which is evident by the decreased stiffness (FIG. 15B) and increased compliance (FIG. 15D). Please note that due to technical issues, the pressure and diameter measurements for one of the sham controls were not possible and thus there was one less data set (N=5) than in the spun group (N=6).

Biological Analyses

Histology

Figure 16:
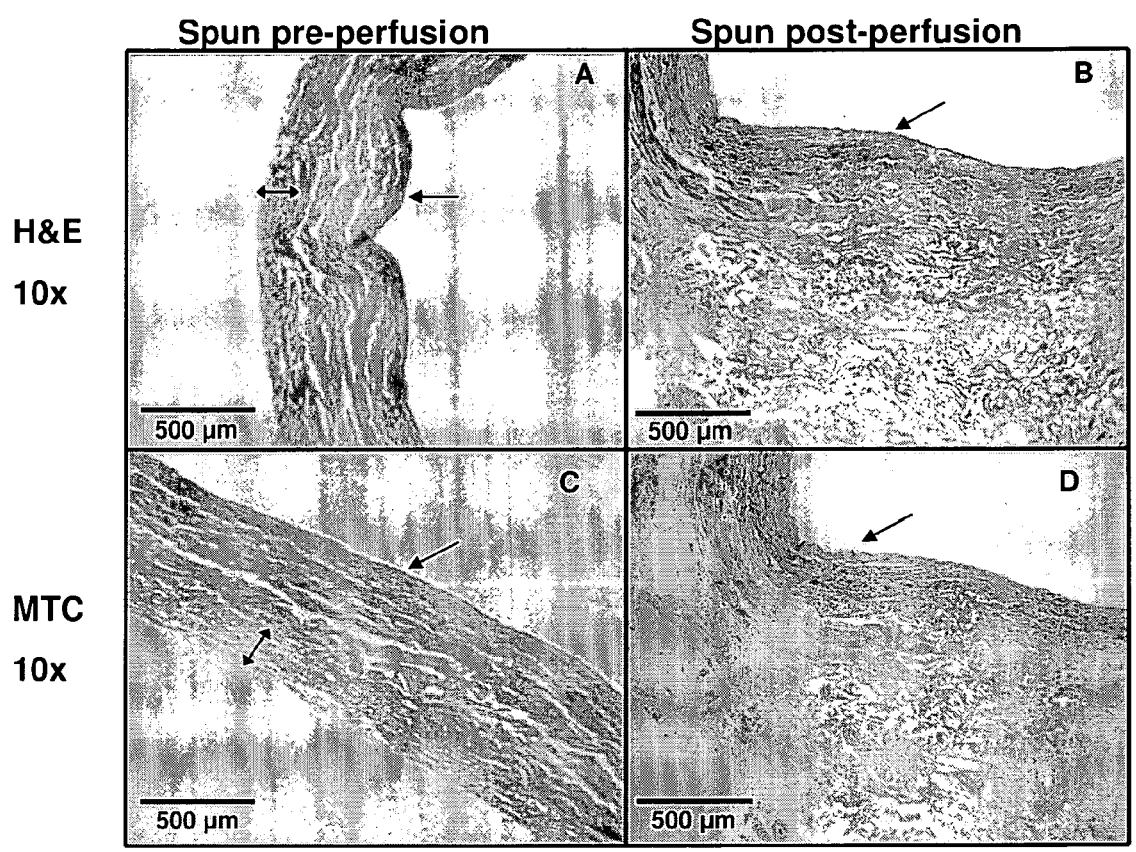
FIG. 16: H&E (A,B) and Masson's trichrome images (C,D) for both before perfusion and after wrapping procedure (A,C) and after 24 hours of ex vivo perfusion (B,D). Note the uniform thickness of the polymer wrap prior to perfusion, and the absence of the polymer wrap in the post-perfusion images. The single-headed arrow indicates the vessel lumen. The double-headed arrow in (A) and (C) indicates the thickness of the polymer wrap, which was not detectable in (B) or (D).

Histologic images were consistent with the SEM images in that they also showed the polymer wrap to be well attached to the adventitial surface of the vein and that it can be electrospun with an approximately uniform thickness (FIGS. 16A and 19C). Further, the polymer degraded nearly completely following the 24 hour perfusion period (FIGS. 16B and 16D).

Figure 17:
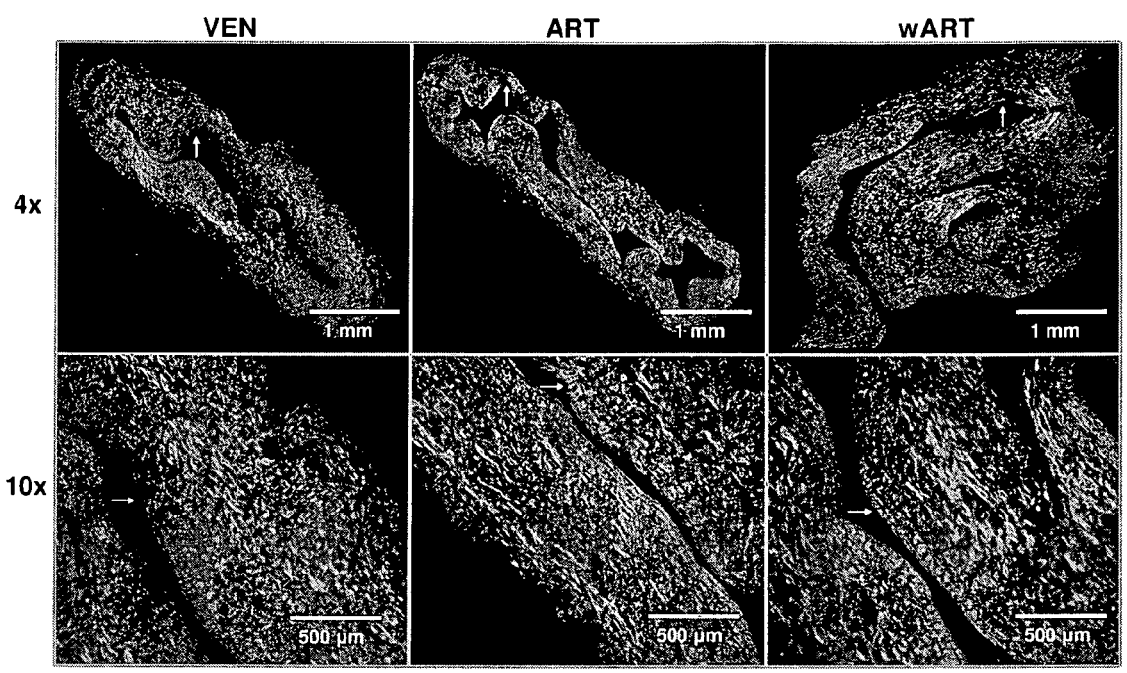
FIG. 17: Representative birefringence images of vein sections stained with picrosirius red (original in color). The experimental conditions are defined as: Venous (VEN) conditions of 20 mmHg pressure and 20 ml/min flowrate; pulsatile arterial (ART) conditons of 120/80 mmHg pressure and 100 ml/min mean flowrate; and wrapped arterial (wART) conditions where the wrapped vein segments were perfused under ART conditions for 24 hours ex vivo. The arrow indicates the vessel lumen.

FIG. 17 shows representative birefringence images of vein sections stained with picrosirius red. In each image, the color range from red to green indicates a range of collagen fiber organization with red being most organized and green being less organized. The granulated appearance of the staining indicates the natural crimped collagen fiber state, whereas stretched fibers appear striated rather than granulated. These results suggest that the polymer wrap reduces the level of collagen fiber stretching (including greater organization and reduced crimping) when compared to a control PIJV segment perfused ex vivo under ART conditions for 24 hours.

Figure 18:
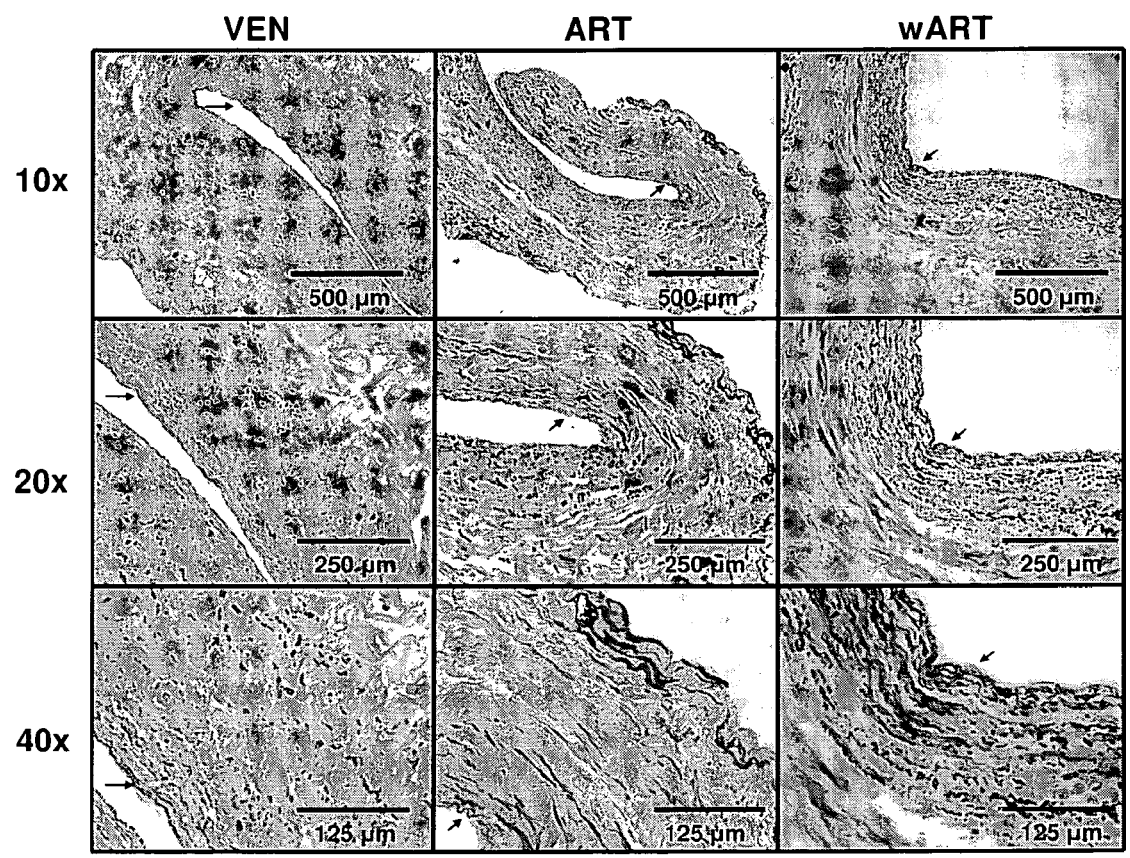
FIG. 18: Movat's pentachrome staining of vein tissue sections (original in color). In each image collagen stains yellow, elastin and nuclei stain black, and muscle stains red. The red staining in the adventitial side of the wART sections is unspecific staining of culture media proteins that become entrapped within the polymer during ex vivo perfusion experiments. The arrow indicates the vessel lumen.

Representative images of Movat's pentachrome stained tissue section are shown in FIG. 18. The internal elastic lamina appears disrupted in the PIJVs perfused under ART conditions when compared to both VEN and wART conditions. As with the picrosirius red staining, this data suggests that the polymer wrap was successful in reducing the level of stretch within the vein wall when exposed to ART conditions.

SEM

The electrospun adventitial wrap exhibited high porosity and tight adherence to the adventitial surface of the veins (FIGS. 19A-C), which suggests that the wrap would provide structural support to an AVG without inhibiting adventitial nutrient and gas diffusion into the tissue. Another important observation was that the electrospinning process did not appear to damage the endothelial layer, which remained continuous (FIG. 19D).

Necrosis

Figure 20:
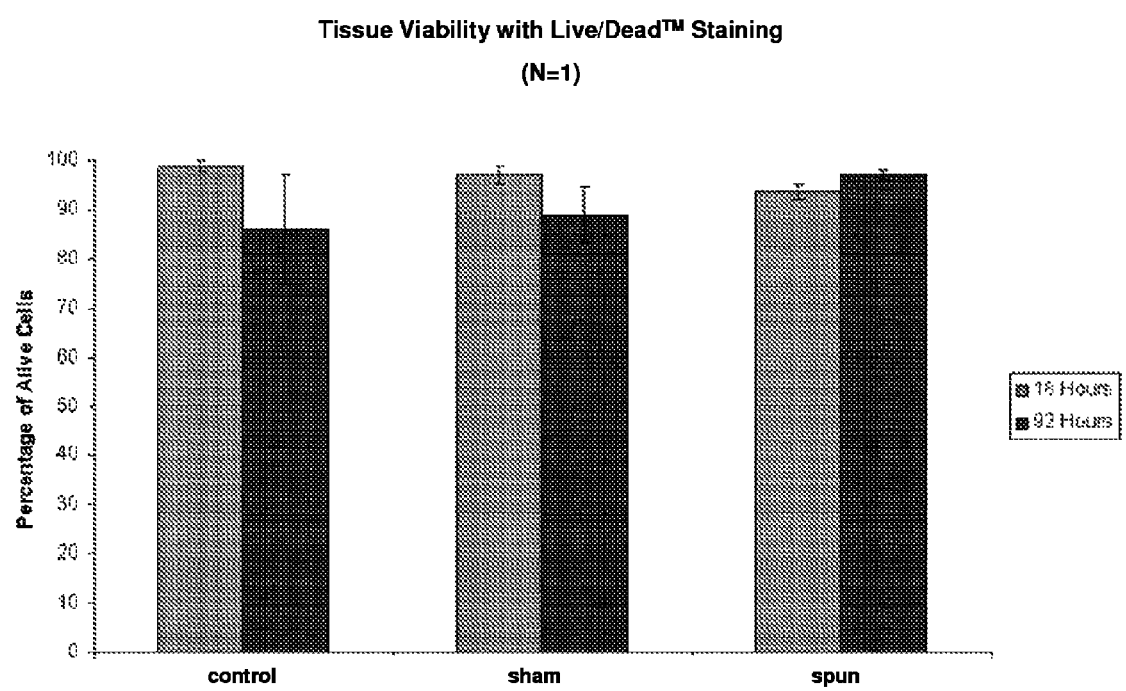
FIG. 20: Quantified Live/Dead.TM. results to assess the level of necrosis in PIJVs after electro spinning, and after 18 and 92 hours of post-electrospinning static culture. The data shown was for a single experiment, and the error bars result from the 10 fields of view that were analyzed per PIJV segment. The data are presented as mean±standard error of the mean.

There was no significant difference in tissue viability between each experimental group for each timepoint (FIG. 20).

Apoptosis

Figure 21:
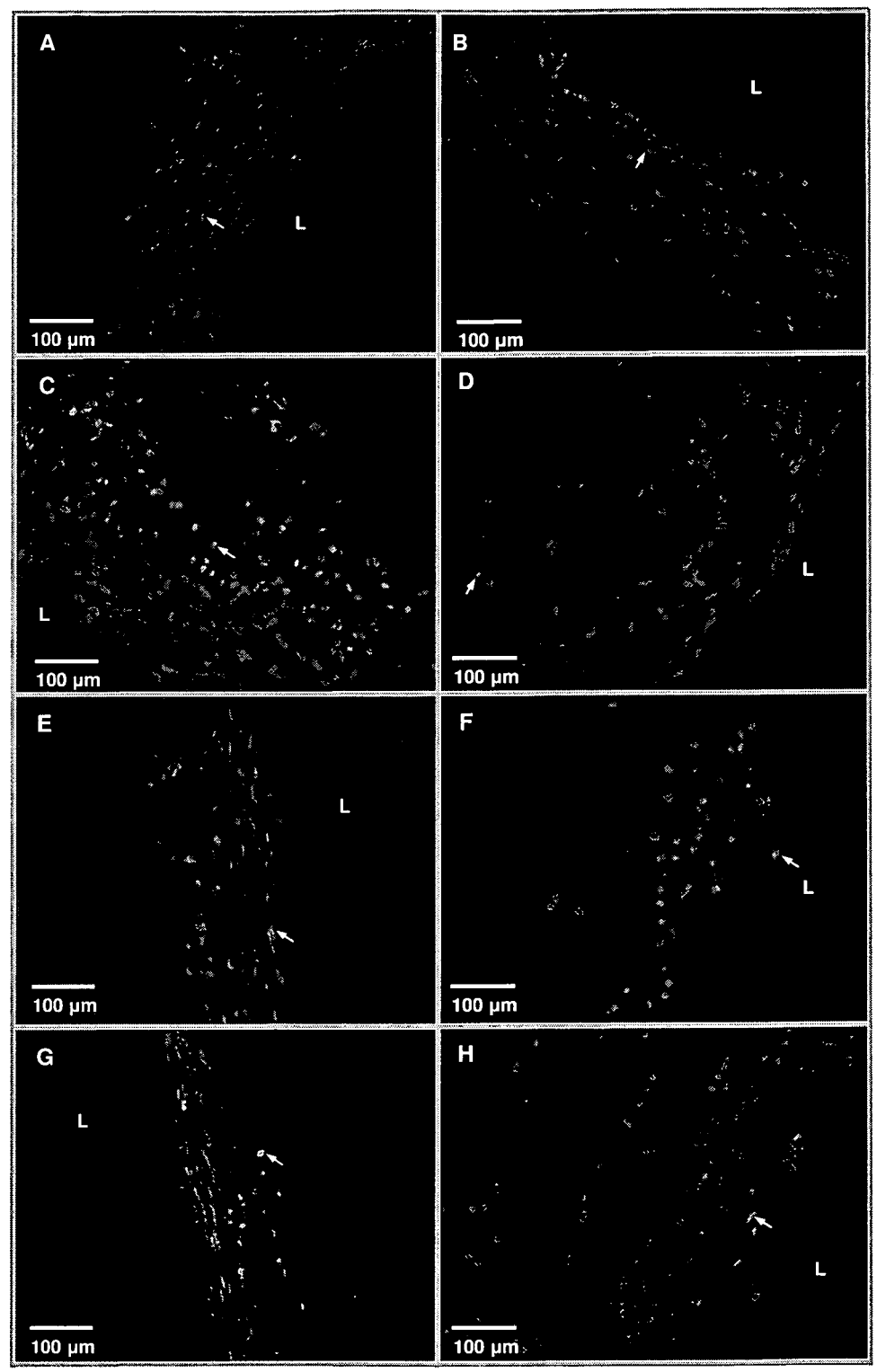
FIG. 21: Representative immunohistochemistry images from the fluorescent based TUNEL analysis (originals in color). The top two panels are from a 24-hour VEN (A) vs. ART (B) experiment. The next two panels are from a 24-hour ART (C) vs. cART (D) experiment. The third row of panels are from a 72-hour ART (E) vs. cART (F) experiment. The bottom two panels are from a 24-hour ART (G) vs. wART (H) experiment. The arrows indicate apoptotic cells. L indicates the PIJV lumen.
Figure 22:
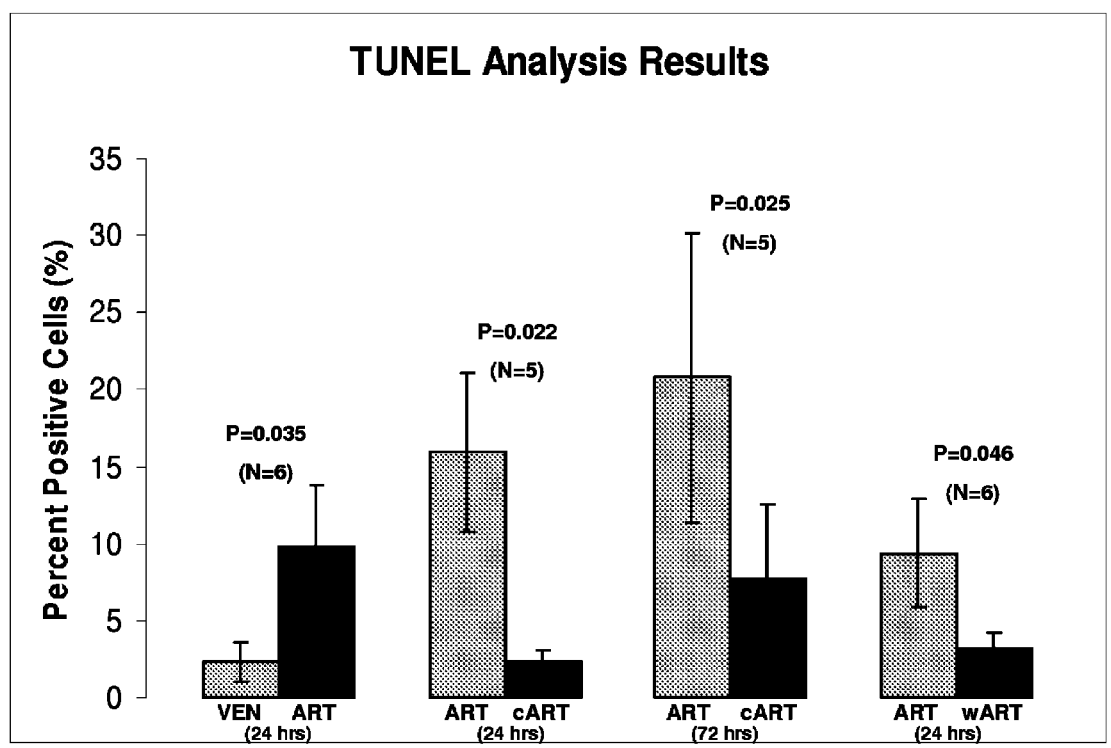
FIG. 22: Quantified immunohistochemistry results from fluorescent based TUNEL analysis to assess the percentage of apoptotic cells within PIJVs from all the ex vivo vascular perfusion experiments. The data are presented as mean±standard error of the mean.

FIG. 21 shows representative paired fluorescent immunohistochemistry images of TUNEL staining from all four ex vivo vascular perfusion experiments described above. FIG. 22 shows the quantified TUNEL analysis results from these experiments. It can be seen that there is a statistically significant increase in apoptotic cells within PIJVs abruptly exposed to ART conditions vs. VEN controls. However, the mechanical conditioning paradigm imposed via cART conditions (for both 24 and 72 hours) and via the biodegradable electrospun polymer wrap (wART conditions) statistically significantly reduced the number of apoptotic cells within PIJVs vs. ART control conditions.

Proliferation

Figure 23:
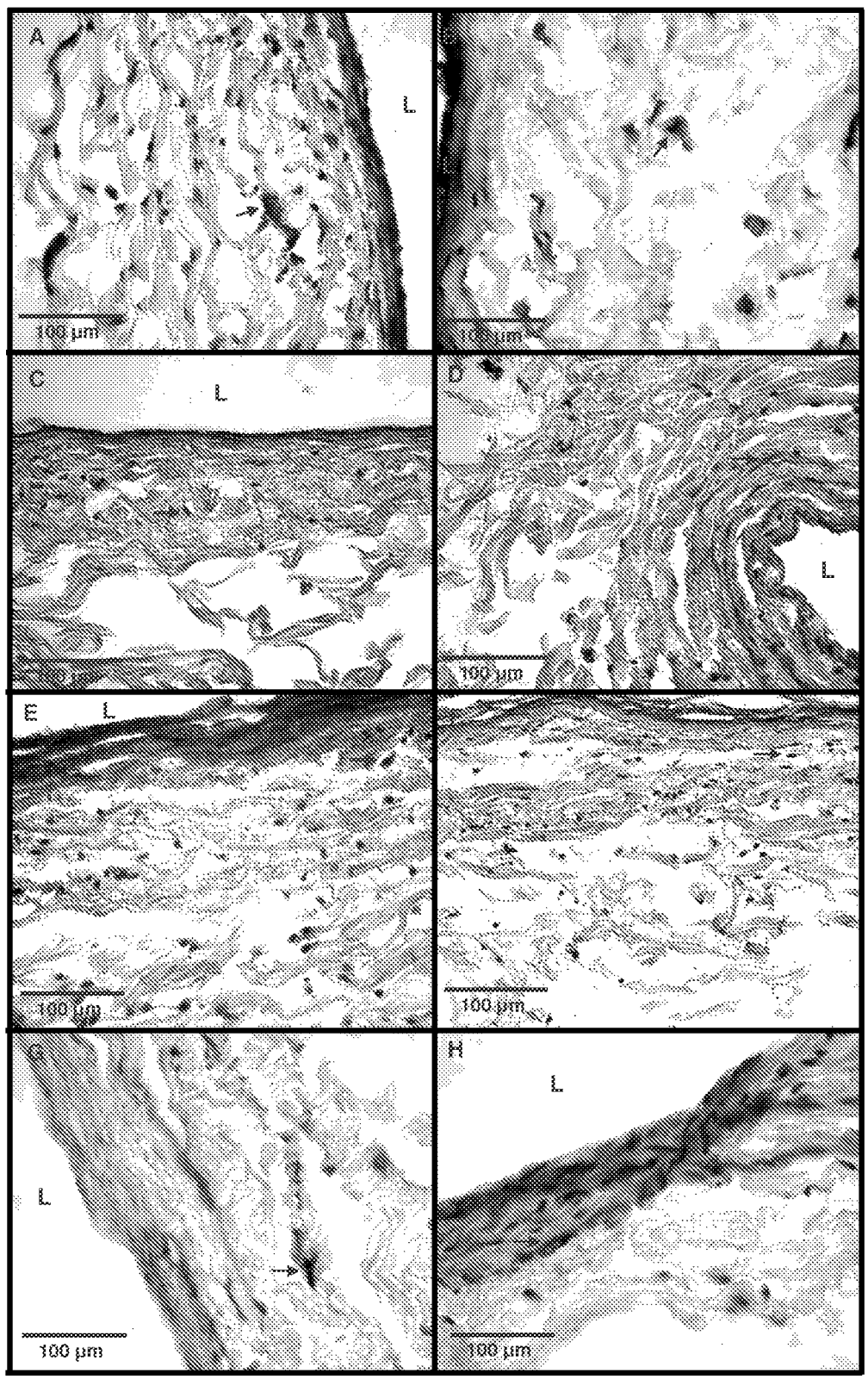
FIG. 23: Representative immunohistochemistry images s from the HRP/ABC based PCNA analysis (originals in color). The top two panels are from a 24-hour VEN (A) vs. ART (B) experiment. The next two panels are from a 24-hour ART (C) vs. cART (D) experiment. The third row of panels are from a 72-hour ART (E) vs. cART (F) experiment.

FIG. 23 shows representative paired HRP/ABC based immunohistochemistry images of PCNA staining from all four ex vivo vascular perfusion experiments described above. FIG. 24 shows the quantified PCNA analysis results from these experiments. It can be seen that there is a statistically significant decrease in proliferating cells within PIJVs abruptly exposed to ART conditions vs. VEN controls. However, the mechanical conditioning paradigm imposed via cART conditions (24 hours) and via the biodegradable electrospun polymer wrap (wART conditions) statistically significantly inhibited the decrease in the number of proliferating cells within PIJVs vs. ART control conditions. The number of proliferating cells within PIJVs exposed to cART conditions for 72 hours was not statistically significantly different than ART controls.

SMC Phenotype

FIG. 25 shows representative paired HRP/ABC based immunohistochemistry images of Golgi complex staining from all four ex vivo vascular perfusion experiments described in above. FIG. 26 shows the quantified Golgi complex analysis results from these experiments. It can be seen that there is a statistically significant increase in the number of cells staining positive for Golgi complex within PIJVs abruptly exposed to ART conditions vs. VEN controls. The mechanical conditioning paradigm imposed via cART conditions (for both 24 and 72 hours) and via the biodegradable electrospun polymer wrap (wART conditions) suggests only a trend towards statistically significantly inhibiting the increase in the number of cells positively stained for Golgi complex within PIJVs vs. ART control conditions.

Discussion

Figure 19:
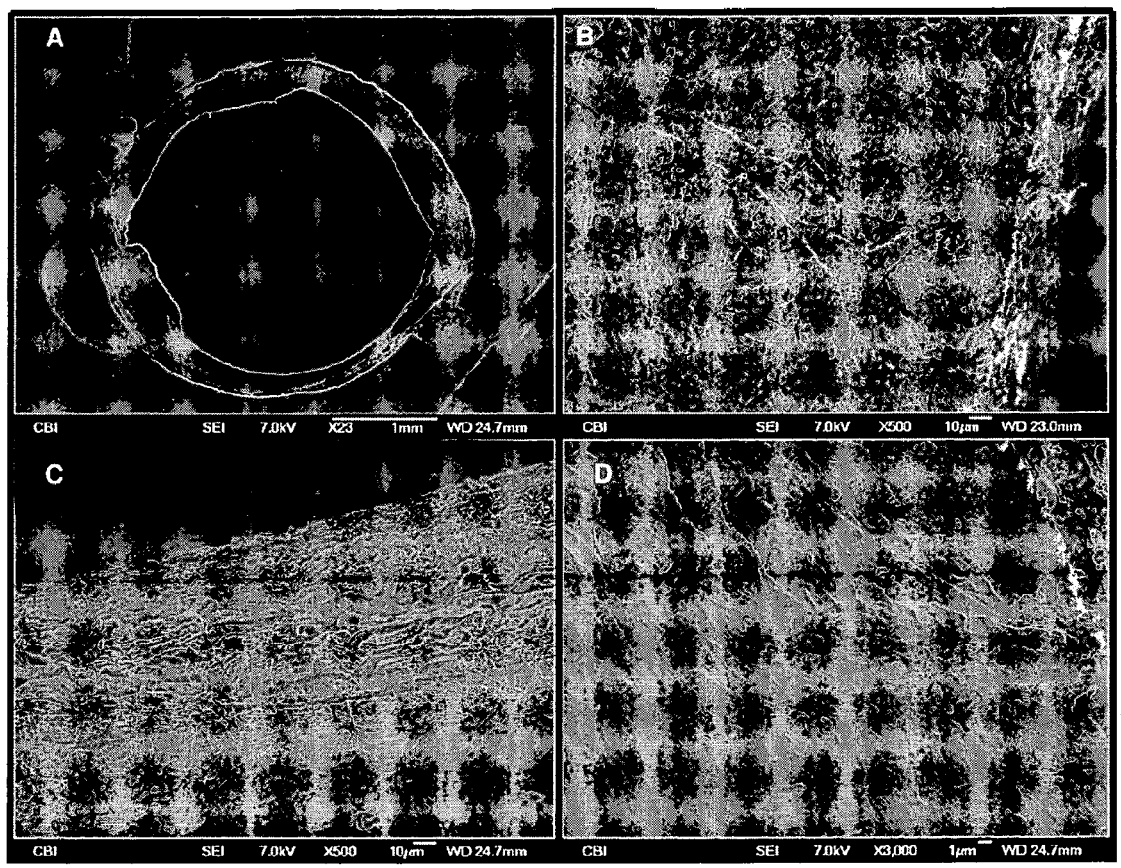
FIG. 19: (A) shows a low magnification SEM image of the PIJV segment with the electrospun polymer deposited onto its adventitial surface. (B) is an SEM image (taken at 500.times. magnification) of the adventitial surface of the PIJV after the polymer wrap was applied. Note the high porosity of the polymer wrap. (C) is an SEM image (taken at 500.times. magnification) showing the attachment of the polymer wrap to the vein. (D) is an SEM image (taken at 500.times. magnification of the luminal surface of the vein and shows a continuous endothelium layer which appears to have remained intact.

The work presented in this chapter shows, that a biodegradable electrospun polymer wrap can be uniformly (FIG. 16) and safely (FIGS. 13 and 14) electrospun onto vein segments, and that the wrap can be tuned to completely degrade (FIG. 16) such that CWS is applied to an AVG at a desired rate (FIG. 12). Having control over the biodegradation rate of an adventitially placed electrospun polymer wrap could lend itself to three potentially beneficial support modalities for attenuating IH in AVGs. As shown here, biomechanical support can be delivered at a desired rate. Consequently, delivery of both biochemical (drugs), and biological (cellular) support might theoretically be achieved using the same approach (Stankus J J, Guan J, Fujimoto K, and Wagner W R. Microintegrating smooth muscle cells into a biodegradable, elastomeric fiber matrix. Biomaterials. 2006; 27(5): 735-44 and Stankus J J, Soletti L, Kazuro F, Hong Y, and Vorp D A. Fabrication of cell microintegrated blood vessel constructs through electrohydrodynamic atomization. 2007; Accepted). The potentially beneficial effects of the polymer wrap on AVG microstructure were observed from the picrosirius-red and Movat's pentachrome staining (FIGS. 17 and 18, respectively). The polymer wrap seems to provide structural support to AVGs resulting in a more naturally crimped configuration of the collagen fibers (FIG. 17), as well as less damage to the internal elastic lamina (FIG. 18). Maintaining integrity of the structural proteins that comprise the AVG wall may help to minimize the detrimental mechanical triggers received by the vascular ECs and SMCs and hence could help to attenuate IH in AVGs. We also assessed the level of necrosis via Live/Dead™ staining in the electrospun PIJVs and showed no appreciable increase in necrosis due to electrospinning over sham and static controls (FIG. 19). This data in addition to the vasomotor challenge data (FIGS. 13 and 14) is more evidence to show that tissue viability is not affected by electropsinning.

The immunohistochemistry results suggest that gradual vs. abrupt exposure of AVGs to arterial levels of CWS may be beneficial. The balance between apoptosis and proliferation, as seen in FIGS. 22 and 24 respectively, was shown to be disrupted due to abrupt exposure of PIJVs to ART conditions over VEN controls. The observed increase in apoptosis and reduction in proliferation in PIJVs perfused under ART conditions suggests that there is an immediate shift in cellular function due to the aletered biomechanical environment of the vein. This shift in cellular function within veins was shown to be inhibited by more gradual imposition of arterial levels of CWS via cART and wART ex vivo perfusion conditions. In addition, as expected the level of Golgi complex expression in PIJVs exposed to ART conditions was increased over VEN controls (FIG. 26), suggesting a modulation in SMC phenotype to a more synthetic state. This observed shift in cellular function was not statistically significantly inhibited by gradual exposure to ART levels of CWS via cART or wART conditions. An observed trend towards inhibition, however, of this shift was shown in FIG. 26. Additional experiments are required to determine if this trend becomes statistically significant.

The observed alteration in SMC phenotype that resulted from exposing PIJVs to ART conditions agrees with previously reported data (Simosa H F, Wang G, Sui X, Peterson T, Nana V, Altieri D C, and Conte M S. Survivin expression is up-regulated in vascular injury and identifies a distinct cellular phenotype. J Vasc Surg. 2005; 41(4): 682-90; Zhang W D, Bai H Z, Sawa Y, Yamakawa T, Kadoba K, Taniguchi K, Masuda J, Ogata J, Shirakura R, and Matsuda H. Association of smooth muscle cell phenotypic modulation with extracellular matrix alterations during neointima formation in rabbit vein grafts. J Vasc Surg. 1999; 30(1): 169-83; and Wolff R A, Malinowski R L, Heaton N S, Hullett D A, and Hoch J R. Transforming growth factor-beta1 antisense treatment of rat vein grafts reduces the accumulation of collagen and increases the accumulation of h-caldesmon. J Vasc Surg. 2006; 43(5): 1028-36). The concept of more gradual imposition of arterial levels of CWS to AVGs has not previously been reported but could result in a means to retard or inhibit SMC phenotypic modulation which could consequently reduce the hyperplastic response. The reduction in apoptosis in PIJVs exposed to ART vs. VEN conditions also agrees with published results (Liu B, Itoh H, Louie O, Kubota K, and Kent K C. The signaling protein rho is necessary for vascular smooth muscle migration and survival but not for proliferation. Surgery. 2002; 132(2): 317-25; Pintucci G, Saunders P C, Gulkarov I, Sharony R, Kadian-Dodov D L, Bohmann K, Baumann F G, Galloway A C, and Mignatti P. Anti-proliferative and anti-inflammatory effects of topical mapk inhibition in arterialized vein grafts. Faseb J. 2006; 20(2): 398-400; Alcocer F, Whitley D, Salazar J, Jordan W, and Bland K I. Mutual exclusion of apoptosis and hsp70 in human vein intimal hyperplasia in vitro. J Surg Res. 2001; 96(1): 75-80; Igase M, Okura T, Kitami Y, and Hiwada K. Apoptosis and bcl-xs in the intimal thickening of balloon-injured carotid arteries. 1999; 96(6): 605-12; Kamenz J, Seibold W, Wohlfrom M, Hanke S, Heise N, Lenz C, and Hanke H. Incidence of intimal proliferation and apoptosis following balloon angioplasty in an atherosclerotic rabbit model. Cardiovasc Res. 2000; 45(3): 766-76; and Wang G J, Sui X X, Simosa H F, Jain M K, Altieri D C, and Conte M S. Regulation of vein graft hyperplasia by survivin, an inhibitor of apoptosis protein. Arterioscler Thromb Vasc Biol. 2005; 25(10): 2081-7). However, the reduction in proliferation in ART perfused PIJVs vs. VEN, cART, and wART groups was inconsistent with some published data (Nishibe T, Miyazaki K, Kudo F, Flores J, Nagato M, Kumada T, and Yasuda K. Induction of angiotensin converting enzyme in neointima after intravascular stent placement. Int Angiol. 2002; 21(3): 250-5; Predel H G, Yang Z, von Segesser L, Turina M, Buhler F R, and Luscher T F. Implications of pulsatile stretch on growth of saphenous vein and mammary artery smooth muscle. Lancet. 1992; 340(8824): 878-9 and Dethlefsen S M, Shepro D, and D'Amore P A. Comparison of the effects of mechanical stimulation on venous and arterial smooth muscle cells in vitro. J Vasc Res. 1996; 33(5): 405-13). Liu et al. suggested however that mechanical stretch due to arterial hemodynamics induces cell death, which possibly mediates subsequent cell proliferation (Liu B, Itoh H, Louie O, Kubota K, and Kent K C. The signaling protein rho is necessary for vascular smooth muscle migration and survival but not for proliferation. Surgery. 2002; 132(2): 317-25). The short-term timepoints studied in this dissertation may not have been long enough to see a rise in proliferation after the initial increase in apoptosis in the ART perfused PIJVs.

Several limitations of this chapter should be noted. Although the Live/Dead™ assay is widely used to evaluate necrosis in living cells and tissues, it arguably was not ideally suited for our application. This was due to the limited distance the reagents were able to diffuse through the thickness of vascular tissue. It was observed that the staining occurred predominantly in the intimal and adventitial layers of the vein wall, while the media was largely devoid of signal. It is true that the adverse effect of the electrospinning process would be in the area of contact between the polymer wrap and the vein wall (i.e., the adventitia), as well as in the area of contact between the mandrel and the vein wall (i.e., the lumen). The Live/Dead™ assay appeared to work well in both of these areas and showed no appreciable increase in the level of necrosis when compared to control tissue. Additionally, the vasomotor challenge data indicated that the spun PIJV was able to contract with the same intensity as the sham control which demonstrated the viability of the SMCs comprising the medial layer of the tissue. Finally, we would have ideally compared the vasomotor responses of the sham and spun PIJVs to a baseline control response—that is, with a freshly excised PIJV segment. However, obtaining a third segment of PIJV for immediate testing was not feasible since we could only harvest two PIJV segments per animal. We feel that the choice of a sham control over a baseline control was acceptable in that we wanted to assess the differences associated only with electrospinning

CONCLUSION

We showed here that a tunable polymer wrap can be applied to vein segments without compromising viability or function, and demonstrated one potential application; i.e., gradually imposing the mid-wall CWS in wrapped veins exposed to arterial levels of pressure. The gradual imposition of arterial levels of CWS, rather than abrupt exposure, may be an important new means to reduce the hyperplastic response of AVGs, promoting instead safe arterialization.

Incorporation of either pharmaceuticals or cells into an adventitial polymer wrap represents a possible future application, and may further enhance the patency of AVGs. To our knowledge, controlled delivery of cellular support via a biodegradable AVG wrap/sheath has not been previously reported and hence this possible future application of the adventitial wrap would be novel. The polymer that was used in this report has been characterized, and successfully micro-integrated with viable SMCs, and would lend itself to this possible future application.

Example 4

In Vivo Arterial Vein Grafting

Eight (n=8) "proof of concept" carotid interposition vein graft experiments were performed. We wanted to evaluate the mitigating effect of the electrospun PEUU adventitial wrap on the acute and chronic hyperplasic response of vein segments implanted as carotid interposition grafts in a preclinical model. For this, we used a unilateral autologous carotid interposition graft protocol for pigs. Pigs were divided into two groups: a "spun" AVG group and a "sham control" AVG group. Each animal served as its own vein graft donor. In brief, PIJVs were harvested as described in Example 2 and were either spun with the same wrap composition and thickness as described in that Example using the electrospinning process described therein, or designated as sham controls. Again, for the sham PIJV segments without the electrospun polymer wrap, we mimicked the electrospinning process up to the point of actually placing the polymer wrap (i.e., including the insertion of the mandrel and rotating/translating the vein within the electrical field). The AVGs were then implanted as carotid interposition grafts (as described in below) for 30 days (or upon observing irreversible complications), an implant duration sufficient to allow IH to be grossly apparent in the sham control group (Angelini G D, Bryan A J, Williams H M, Morgan R, and Newby A C. Distention promotes platelet and leukocyte adhesion and reduces short-term patency in pig arterio-venous bypass grafts. J Thorac Cardiovasc Surg. 1990; 99(3): 433-9; Vijayan V, Shukla N, Johnson J L, Gadsdon P, Angelini G D, Smith F C, Baird R, and Jeremy J Y. Long-term reduction of medial and intimal thickening in porcine saphenous vein grafts with a polyglactin biodegradable external sheath. J Vasc Surg. 2004; 40(5): 1011-9 and Jeremy J Y, Dashwood M R, Timm M, Izzat M B, Mehta D, Bryan A J, and Angelini G D. Nitric oxide synthase and adenylyl and guanylyl cyclase activity in porcine interposition vein grafts. Ann Thorac Surg. 1997; 63(2): 470-6) to which the spun group was compared. In addition to evaluating patency via angiography, the explanted AVGs were processed for histological evaluation of IH. Please note that the quantified endpoints of the in vivo studies were strictly histological in nature.

Methods

Unilateral Porcine Carotid Interposition Grafting

Animals were brought into the facility 7-10 days prior to the day of the experiment, and kept NPO 12 hours prior to surgery. Prior to surgery, animals were anesthetized with Acepromazine, 0.15 mg/kg 1M, and Ketamine, 15.0 mg/kg, 1M combination, intubated and maintained at a surgical plane of anesthesia with Isoflurane (1-3% in oxygen). Once each animal was clipped and prepped for the procedures it was moved into the surgical suite and placed on positive pressure ventilation and instrumented with monitoring equipment (ECG). Pulse oximetry and blood pressure were monitored throughout the surgical procedure. After the induction of anesthesia, aseptic surgery was performed.

Unilateral cervical incision was made to expose the common carotid artery. The animal was then heparinized (300 UI/Kg), and the artery clamped proximally and distally using atraumatic vascular clamps. The segment between clamps was excised (~6 cm). Each pig served as its own graft donor. A fresh unilateral IJV harvest was performed on the pig as described above. The harvested IJV was then either spun (as described above and in Stankus et al. [47]) or designated as the sham control. The vein segment was then implanted as a unilateral carotid interposition graft (end to end) using interrupted 7-0 prolene sutures.

Post-operatively, animals were recovered and housed in an intensive care unit. Following the surgical procedure and cessation of inhalation anesthesia, the animal were extubated when it exhibited a swallowing reflex and the protective cough reflexes are functional. The animals were continually monitored for 24 hours, and the following parameters were recorded every hour: pulse rate, strength of pulse, capillary refill time, respiratory rate, urinary output, and defecation. Body temperature was determined and recorded every 2 hours. The animal was kept warm and dry to prevent hypothermia. Buprenorphine hydrochloride (0.005-0.01 mg/kg, 1M, q12 h) was administered at regular intervals for 4 days for pain and continued to be administered for pain management if signs of pain were exhibited. Acute pain in animals is expressed by guarding, vocalization, mutilation, restlessness, recumbency for an unusual length of time, depression (reluctance to move or difficulty in rising), or abnormal appearance (head down, tucked abdomen, hunched). Skin staples/sutures were removed 10 days post-op. All animals were monitored daily by a trained staff of Veterinarians, Registered Veterinary Technicians, and animal care personnel.

An anti-coagulation regimen was used to battle acute AVG failure via thrombosis. Oral doses of aspirin (325 mg/day) and Plavix (75 mg/day) were both started 3 days pre-operatively. The Aspirin was administered daily for the entire 30 day post-operative period, and Plavix was administered daily for only 14 days post-operatively.

After a 30-day survival time (or upon observing irreversible complications), the animals were euthanized. The pigs were deeply anesthetized with Acepromazine, 0.15 mg/kg 1M, and Ketamine, 30.0 mg/kg, IM combination, and the animals were then euthanized by injection of an overdose of intravenous potassium chloride to induce cardiac arrest. Vital signs were monitored to effect.

Fluoroscopic Angiography

After euthanasia and just prior to graft explant, fluoroscopic angiography was performed to assess graft patency. The carotid artery was clamped approximately 3 cm upstream of the proximal graft anastomosis, and contrast medium was infused into the carotid artery immediately distal to the clamp. Angiograms were recorded (Model OEC 9800 Plus, General Electric Inc.) to verify flow through the entire graft segment. If flow could not be established through a graft (ie. due to occlusion), angiography was not performed.

Post-Explant Tissue Processing

The grafts were extracted and ½ the tissue was immediately fixed in 4% paraformaldehyde and analyzed histologically as described in below. The other ½ of the tissue was fixed in ultrapure 2.5% gluteraldehyde for SEM analysis as described in Section above.

Histological Measurement of IH

Morphometric analysis was performed on sections from the central region of the explanted grafts. Using standard Movat's pentachrome staining techniques, intimal and medial thicknesses were measured. The intimal to medial thickness ratios were calculated from these measurements. Measurements were made from 4 fields of view and averaged to yield a sinlge value for each AVG section.

Scanning Electron Microscopy

The same procedure as described above was used to process and image the explanted AVGs from the in vivo experiments.

Statistics

An unpaired student's t-test was performed on the intimal to medial thickness ratio data. $P<0.05$ was considered statistically significant. Unless otherwise indicated, data are presented as mean±standard error of the mean.

Results

The adventitial polymer wrap had an immediately apparent effect of maintaining the AVG at a diameter consistent with that for the native vein (compare FIG. 27 middle and right) under arterial pressure. In addition, the wrapped AVGs exhibited pulsatile radial excursions (i.e., compliance) similar to the native carotid artery, whereas the un-wrapped AVG appeared to be a rigid tube with no detectable pulsations. That is, upon establishing flow through the control grafts, it was observed that unlike the native carotid arteries and spun veins, the sham control veins did not change in diameter in response to the pulsatile pressure.

Out of the 8 in vivo experiments that were performed, only 1 experiment was completely successful. That is, the AVGs from both the spun and sham pigs were 100% patent after 30 days. Angiography images of these AVGs can be seen in FIG. 28. The rest of the experiments were deemed unsuccessful due to one of 3 reasons: 1) partial occlusion of one or both the spun and sham AVGs due to IH or thrombosis; 2) post-operative complications leading to the death of one animal in the spun group; and 3) infection resulting in the need to euthanize one animal in the spun group after 1 week post-op. However, with the 2 patent AVGs and the AVGs that were only partially occluded (sham, N=6; spun, N=4) we performed morphometric measurements to assess IH development for comparison between the two groups. Representative images of Movat's pentachrome stainging that were used in the morphpometric analysis are shown in FIG. 29, which also shows a sample measurement. The quantified results can be seen in FIG. 30. There seems to be only a trend towards statistical significance between the intimal to medial thickness ratios of the spun vs. sham control groups.

SEM images were taken of the AVGs from one completely successful experiment (FIGS. 31A and 31B) as well as from another experiment where the AVGs were not comletely occluded (FIGS. 31C and 31D). The anastomotic interface between the vein graft and artery, evidenced by the suture line, can be seen in each image.

Discussion

Although we observed only a trend towards a statistically significant difference in the intimal to medial thickness ratio between the spun and sham groups, it is likely that this difference would become statistically significant if the number of experiments was increased. The quantified morphometric results as well as the qualitative SEM results suggest that the electropun biodegradable polymer wrap does offer a favorable effect to AVGs. However, further investigation is necessary to determine if these effects are in fact consistently beneficial. In addition to the inherent variability associated with mechanopathobiological data, there was also variability introduced into our results by having 3 different surgeons, of varying experience, perform the surgeries. It is also true that there is a "learning curve" associated with creating anastomoses using a two layered AVG (spun group) instead of the normal one layered AVG (sham group). As with any new surgical procedure, as the comfort level of the surgeon performing the surgery increases, the success rate of the surgery consequently increases.

Previous studies that have attempted to use an external sheath to reduce AVG IH, described above, focused on the delivery of mechanical (as described in this dissertation) and biochemical support to AVGs in various animal models. Clinical translation of these previous approaches was not achieved due to two main limitations. Specifically, they all used either loose-fitting/biodegradable or loose-fitting/biodurable sheaths. In this work, we desired to address these limitations by developing a means to safely "wrap" an AVG with a tight-fitting and biodegradable polymer.

There are limitations to the work presented here. The fact that the sham controls were not paired to the spun AVGs (i.e., from the same pig) provides us with less statistical power in the study. However, the unpaired experimental design that was used was deemed necessary in order to avoid post-operative complications in the animals. We felt it was safer to perform unilateral surgeries instead of bilateral so that the venous blood return from the brain would not be excessively altered. Another limitation stems from the varying experience of the surgeons who performed the procedures. It is likely that the results would be more statistically significant if the patency rate of the AVGs was increased. If the procedures were all performed by the most experienced surgeon, the electrospun biodegradable polymer wrap may have significantly reduced IH in the AVGs over sham controls. A third limitation is that the 30-day duration of the implants was too short. Longer term experiments, perhaps as long as 6 months, are required to determine if the efficacy of our approach in reducing AVG IH is sustained over time.

Referring now to FIG. 32, a side sectional view of a tubular graft device of the present invention is illustrated, including a tubular member with a surrounding fiber matrix whose thickness varies along at least a portion of the length of the device. Device 100 includes tubular member 140, typically a harvested vessel graft from a patient. In an alternative embodiment, tubular member 140 may be an artificial graft, such as a Dacron, PTFE or ePTFE tube, or other tubular material well known to those of skill in the art. Tubular member 140 may comprise a braided structure, such as a tube or coil of solid, braided, knitted or wound material comprising a polymer of similar or different material to fiber matrix 120 or comprising a metal such as Nitinol, stainless steel, elgiloy, tantalum, MP35N, or a variety of other biocompatible metals, or a resorbing metal such as magnesium, or a combination of different materials such as mentioned above. Tubular member 140 includes lumen 150 from its proximal end, first end 101, to its distal end, second end 102. Surrounding tubular member 140 is a fiber matrix comprising first longitudinal portion 120a and second longitudinal portion 120b.

As shown in FIG. 32, portion 120a proximate end 101 has a thicker wall than portion 120b in the middle of device 100, which can be achieved by applying more fiber in portion 120 during the fiber deposition process (e.g. an electrospinning process). Portion 120c, proximate to end 102, may also have a thicker wall, such as a wall with a thickness proximating portion 120a. A continuous taper is provided from first end 101 to the midportion of device 100, which symmetrically reverses from the midportion to second end 102. Alternatively, a stepped wall thickness change could be employed. The variable wall thickness along the length of device 100 can be useful in providing multiple functions. The thicker portions 120*a* and 120*c* may provide better strength and/or tear resistance to support an anastomosis, such as suture or clip based end-to-side anastomosis between the first end 101 and the aorta of a patient, and second end 102 and a point distal to an obstructed artery of the patient. The thinner walls of portion 120*b* may be configured to provide reduced radial force, such as a radial force tuned to allow a vessel graft to expand at a particular rate under arterial pressure. The wall thickness variations of portions 120*a*, 120*b* and 120*c* can be configured to create particular flow conditions, support various curvilinear geometries of device 100 when implanted, prevent buckling, and provide other functions.

Alternatively or additionally, portion 120*a*, portion 120*b* and/or portion 120*c* may have additional construction or material differences (i.e. different than thickness) such as different fiber size, different matrix porosity, and other construction differences. Alternatively or additionally, portions 120*a*, 120*b* and/or 120*c* may be constructed of one or more different materials such as materials with different mechanical properties such as different tear strengths, strain resistance, or biodegradation characteristics. Alternatively or additionally, one portion may include an agent such as a pharmaceutical drug or cell based agent, or one portion may include a first agent and another portion include a second, different agent.

Referring now to FIGS. 33*a* and 33*b*, side and end sectional views, respectively, of a tubular graft device of the present invention are shown, including a tubular member with a surrounding fiber matrix whose thickness varies along its circumference, along at least a portion of the device. Device 100' includes tubular member 140, typically a harvested vessel graft from a patient or an artificial graft as has been described hereabove. Tubular member 140 includes lumen 150 from its proximal end, first end 101, to its distal end, second end 102. Surrounding tubular member 140 is a fiber matrix comprising top portion 120*d* and bottom portion 120*e*.

As shown in FIGS. 33*a* and 33*b*, top portion 120*d* of the circumference has a thicker wall than bottom portion 120*e*, which can be achieved by applying more fiber in portion 120*d* during the fiber deposition process (e.g. an electrospinning process). The variable wall thickness along the length of device 100' is preferably a continuous taper along the circumference of device 100', which can be useful in providing multiple clinical and/or mechanical functions. The wall thickness variations of portions 120*d* and 120*e* can be configured to create particular flow conditions, support various curvilinear geometries of device 100', prevent buckling, create a preferred expansion geometry, and provide other functions.

Alternatively or additionally, portion 120*d* and portion 120*e* may have additional construction differences (i.e. different than thickness), such as different fiber size, different matrix porosity, and other construction differences. Alternatively or additionally, portion 120*d* and portion 120*e* may be constructed of one or more different materials such as materials with different mechanical properties such as different tear strengths, strain resistance, or biodegradation characteristics. Alternatively or additionally, one portion may include an agent such as a pharmaceutical drug or cell based agent, or one portion may include a first agent and another portion include a second, different agent.

Referring now to FIG. 34, a side sectional view of a tubular graft device of the present invention is illustrated, including a tubular member with a surrounding fiber matrix whose properties vary along at least a portion of the length of the device. Device 100" includes tubular member 140, typically a harvested vessel graft from a patient. In an alternative embodiment, tubular member 140 may be an artificial graft or other tubular material as has been described hereabove. Tubular member 140 includes lumen 150 from its proximal end, first end 101, to its distal end, second end 102. Surrounding tubular member 140 is a fiber matrix comprising first longitudinal portion 120*f*, second longitudinal portion 120*g*, and third longitudinal portion 120*h*.

Portion 120*f* proximate first end 101 is of dissimilar construction to portion 120*g* at the midportion of device 100". Portion 120*g* may be of different construction than portion 120*h*. Alternatively, device 100" may include four or more sections with dissimilar construction. Construction of each portion may vary in numerous ways, including construction methods and geometries, as well as the fiber materials used. The variable material properties along the length of device 100" can be useful in providing multiple functions, as has been described hereabove. In device 100", portions 120*f*, 120*g* and 120*h* each individually comprise a homogenous tubular section with similar construction geometry, methods and materials. In an alternative embodiment, a continous change in construction geometry, methods and/or materials is present from first end 101 to second end 102. In another alternative embodiment, device 100" includes continuously changing portions and discrete, homogenous portions.

Referring now to FIG. 35, a side sectional view of a tubular graft device of the present invention is illustrated, including a tubular member surrounded by both a fiber matrix and a second scaffolding structure. Device 100''' includes tubular member 140, typically a harvested vessel graft from a patient. In an alternative embodiment, tubular member 140 may be an artificial graft or other tubular material as has been described hereabove. Tubular member 140 includes lumen 150 from its proximal end, first end 101, to its distal end, second end 102. Surrounding tubular member 140 is fiber matrix 120, as has been described in detail hereabove. Fiber matrix 120 comprises one or more of: at least a homogenous portion; at least two different homogenous portions; and at least a portion with continuously varying properties. Surrounding fiber matrix 120 is scaffold 130, preferably of a stent-like construction well known to those of skill in the art. In an alternative embodiment, scaffold 130 is located between tubular member 140 and fiber matrix 120, such as to protect the tubular member during the application of the fiber matrix (e.g. protect from solvents in the polymer solution, delivered heat for the polymer melt, etc.) and/or provide other functions.

Scaffold 130 is constructed of biocompatible materials such as biocompatible metals including stainless steel and Nitinol, or biocompatible plastics such as a combination of one or more polymers. Scaffold 130 may be constructed of a biodegradable material, such as a material which biodegrades at a similar or dissimilar rate to a fiber matrix 120. Fiber matrix 120 may be a biodegradable structure and scaffold 130 a permanent structure such as to provide a radial supporting force for tubular member 140 that is at a first magnitude when first implanted, reduces over the biodegradation period, but provides force, at a second magnitude less than the first, for the life of the implant. Scaffold 130 may provide a homogeneous radial supporting force, or it may vary along its length, such as by providing a greater radial force proximate one or more ends of scaffold 130. Scaffold 130 may be resiliently biased such as to self expand or contract; may be plastically deformable, such as to be expanded or compressed to properly fit around tubular member 140; or may include both resiliently biased (e.g. self-expanding or contracting) and plastically deformable portions. Scaffold 130 may include one or more different portions along its length or circumference, as has been described in reference to fiber matrix 120 of the devices of FIGS. 32 through 34 hereabove, such as a portion proximate each end which provides greater radial force than the radial force provided in a mid portion of device 100'''. In a preferred embodiment, the radial support force provided by scaffold 130 varies along the length of scaffold 130. Scaffold 130 may be of a mesh construction, such as a woven or non-woven construction using coiling, braiding, knitting or other fabrication method. Scaffold 130 may be constructed using techniques for membrane or film deposition and subsequently processed to create porosity such as via needle punching, laser cutting, freeze drying, thermally induced phased separation, electroporation and/or salt leaching. Scaffold 130 may be manufactured with pre-determined porosity and/or pore size, and may exhibit anisotropic properties. Although shown in FIG. 35 as a two-layer or laminate construction, scaffold 130 and fiber matrix 120 may comprise a single layer or composite structure. The composite structure can be formed by scaffold 130 and fiber matrix 120 mechanically intertwining, melting together or otherwise residing in the same layer. Scaffold 130 may provide an anchoring mechanism for device 100'''. In one embodiment, as mentioned hereabove, scaffold 130 is placed between tubular member 140 and fiber matrix 120. The deposited fiber matrix 120 may create a solvent bonding mechanism with scaffold 130, such as when the materials of construction of scaffold 130 and fiber matrix 120 are similar (e.g. for solvent bonding). Alternatively or additionally, the deposited fiber matrix 120 may create a temperature bonding mechanism with scaffold 130, such as when scaffold 130 is a thermoplastic polymer with a low fuse point, and scaffold 130 melts when contacted by the heated polymer of fiber matrix 120 during the fiber matrix application.

Alternatively, scaffold 130 may be a flexible covering, such as a dip covering achieved by dipping tubular member 140 or tubular member 140 with fiber matrix 120 applied, into a liquid solution that results in an attached flexible covering. Lumen 150 may be filled and/or covered during the dipping process, such as to avoid a covering of the inner portion of tubular member 140, or the inner portion of 140 may also include a flexible covering. The flexible covering may be used to provide one or more functions, such as increased radial support, or protection of device 100''' from mechanical damage or contamination. The flexible covering may be biodegradable, and may include one or more agents configured to be released over time. Scaffold 130 may include the dip covering as well as the stent-like structure of FIG. 35.

Alternatively, scaffold 130 may be an artificial graft material, such as an artificial graft material which is expanded and placed around tubular member 140 or tubular member 140 with fiber matrix 120 applied, and then released to cause fixation. The artificial graft is constructed of a biocompatible material such as a Dacron, PTFE, ePTFE tube, or other graft material well known to those of skill in the art. The artificial graft covering may be used to provide one or more functions, such as increased radial support, or protection of device 100''' from mechanical damage or contamination. The artificial graft may be biodegradable, and may include one or more agents configured to be released over time. Scaffold 130 may include the artificial graft as well as the stent-like structure of FIG. 35 and/or the dip covering described hereabove.

Referring now to FIG. 36, a flow chart of one embodiment of a method of manufacturing a tubular graft device of the present invention is illustrated, including performing a patient assessment procedure, and applying a fiber matrix to a tubular member based on data obtained from the patient assessment. Step 200 includes the performance of one or more patient assessment procedures. The patient assessment procedure can include assessments performed in a doctor's office or other healthcare facility including information regarding age; sex; race; blood pressure; blood test information; family history information; stress test data; and combinations of these. The assessment may include one or more tests or other procedures performed during an invasive patient treatment such as an assessment performed in an interventional laboratory or an operating room, such as an angiography procedure or the tubular graft device implantation procedure. In a preferred embodiment, a vessel such as a saphenous vein is harvested, and one or more observations or other tests (e.g. a sizing such as a diameter or vessel wall measurement; or a mechanical properties test such as a test of elasticity of the vessel) are performed to obtain data about the patient's harvested vessel.

In Step 210, a vessel, such as a portion of a saphenous vein, is harvested form the patient. Step 210 can be performed during, simultaneous with, or after Step 200, such as when Step 200 includes an analysis of the harvested vessel. In an alternative embodiment, step 210 includes the fabrication of an artificial graft, such as an elongate tube constructed of a braided or extruded material. Harvested vessels may include veins or arteries, and may be harvested from the patient receiving the tubular graft device or a surrogate, such as an applicable human or other animal donor.

In Step 220, a fiber matrix is applied to the harvested vessel or other tubular member of the present invention based on the data obtained in Step 200. The application of the fiber matrix may be dependent on the anatomical location for the tubular graft device to be implanted, such as when the tubular graft device would be placed in a curvilinear shape. One or more properties of the harvested vessel may determine the fiber matrix configuration such as to reinforce a weakened section of the harvested vessel or otherwise accommodate a geometric or structural property of that vessel. The configuration of the fiber matrix that is optimized or otherwise determined by a patient parameter may include by is not limited to: fiber matrix profile such as a constant or variable thickness; fiber matrix material or combination of materials; fiber matrix radial and/or circumferential and/or axial strengths; fiber matrix radial and/or circumferential and/or axial stiffnesses; fiber matrix bending stiffness; fiber matrix elastic and/or viscoelastic properties; fiber diameter distribution; fiber degradation rate, fiber matrix degradation rate, fiber matrix diffusion properties, fiber matrix wettability; and combinations of these.

As a non-limiting example of optimization based on a patient assessment, in an embodiment, the thickness of the fiber matrix is tailored to accommodated or modify the mechanical reinforcement of the underlying vessel (e.g., underlying vein). That is, the deposition thickness of the fiber matrix is customized according to the Law of Laplace, in this example, to provide a stabilized, reinforced underlying vessel based on a patient's vein assessment. In general, larger veins require more fiber matrix wall thickness than smaller ones to obtain a similar level of mechanical reinforcement. To compensate or to modify mechanical reinforcement based on vessel or vein size, fiber matrix deposition can be customized.

For example, the size of a mandrel (i.e., a vessel holding tool during fiber matrix deposition) can be selected using a male sizing tool fitted within the inner lumen of the tubular vessel or vein, which substantially matches or accommodates the harvested vein or selected tubular vessel. Once the underlying vessel is on the mandrel, the outer diameter of the vessel can be measured using a female sizing tool, such as a sterile credit card sized sheet with several holes identified by size. This measurement, or patient assessment, can occur in a single process or the measurement can be made using the average of a few measurements across the length of the vessel to help take account of variability. In other embodiments, the measurement can be mapped along the entire length of the vessel so that the desired thickness at each location along the length is known.

Once the target size of the tubular vessel or vein is defined, the desired thickness of fiber matrix deposition (possibly customized for each axial location of the tubular vessel or vein) can be determined by estimating the level of required material tensile strength/tension (for each of the two cylindrical directions) to be withstood by the tubular fiber matrix in order to support the luminal pressurization (static and/or dynamic) and geometrical configuration (static and/or dynamic) of the tubular vessel or vein underneath it without experiencing plastic deformation. In embodiments, the level of required material tensile strength/tension will be overestimated by a desired safety factor.

A non-limiting example of a method used to customize the mechanical requirements of the fiber matrix is based on the required circumferential strength of the material, which is defined as the tensile circumferential force per unit of tubular fiber matrix axial length. The strength of each specific material is proportional to its thickness and can be characterized empirically using a tensile testing apparatus for different thicknesses of material.

A non-limiting example of methodology to calculate the required circumferential strength for the tubular fiber matrix (and thus its thickness) is the Law of Laplace, which estimates the circumferential tension ($\sigma$) (i.e., defined as the tensile circumferential force per unit of tubular fiber matrix cross-sectional area) in a pressurized, thin-wall cylindrical conduit with the following equation: $\sigma=Pr/h$, wherein P is the pressure within the vessel acting on the vessel walls, r is the inner diameter radius of the vessel, and h is the wall thickness of the vessel (outer diameter–inner diameter of the vessel).

In the above example, based on the inner diameter vessel measurement, outer diameter vessel measurement, the level of strength required to safely support the circumferential tension obtained via the Law of Laplace, and the knowledge of the relationship between specific material strength and its thickness obtained via empirical measurements, the polymer flow rates or other deposition variables can be altered to achieve customized mechanical reinforcement. This process of tailoring deposition conditions based on patient assessment (i.e., inner and outer diameter vessel measurements) can be accomplished by a skilled technician or alternatively, automatedly by computer/software control after entry of the measured thickness.

The fiber matrix application may include the delivery of multiple types of fibers, such as two or more fibers with different mechanical properties that are delivered simultaneously or sequentially.

Referring now to FIG. 37, a flow chart of one embodiment of a method of manufacturing a tubular graft device of the present invention is illustrated, including monitoring one or more process output parameters during application of a fiber matrix to a tubular member. Step 300 includes placing a tubular member, such as a harvested vessel or artificial graft, onto a holder, such as a mandrel configured to hold a tubular structure during deposition or other application of a fiber matrix, such as an electrospinning process described in detail hereabove. Numerous processes may be used alternative or in addition to an electrospinning process, including but not limited to: wet spinning; dry spinning; gel spinning; melt spinning; and other processes configured to apply a fiber matrix.

In Step 310, the fiber matrix application process is initiated. Numerous process input parameters are used in the fiber matrix application process, as has been described in detail hereabove. In a preferred embodiment, the typical and/or preferred process input parameters are selected from the values of Table 3 herebelow. Process parameters regarding relative movement of the material application device (e.g. nozzle) to the tubular graft may be accomplished by moving the material application device, the tubular graft, or both.

TABLE 3

| System Parameter | Typical Value | Preferred Value |
| --- | --- | --- |
| Translational Velocity and Frequency of nozzle | Velocity: 0 to 1 m/s. Frequency: 0 to 10 Hz | Velocity: 0 to 0.5 m/s. Frequency: 0 to 5 Hz |
| Translational acceleration/deceleration of the nozzle | Acc/DeAcc = 0 to 10 m/s$^2$ | Acc/DeAcc = 0 to 5 m/s$^2$ |
| Translational displacement of nozzle | 0 to 0.5 m (i.e., 1 m length of vein) | 0 to 0.15 m (i.e., 0.3 m length of vein) |
| Nozzle radial distance | 0.1 to 30 cm | 0.5 to 15 cm |
| Mandrel Rotation Rate or directional oscillation rate | 0 to 1000 RPM | 10 to 500 RPM |
| E-Field/charge/voltage Emitter (Nozzle) | Voltage = 0.1 to 30 kV | Voltage = 1 to 15 kV |
| E-Field/charge/voltage Target (Mandrel) | Voltage = −0.1 to −30 kV | Voltage = −1 to −15 kV |
| E-Field between nozzle and mandrel (e.g., along fiber path) | Voltage = 0.2 to 60 kV | Voltage = 2 to 30 kV |

TABLE 3-continued

| System Parameter | Typical Value | Preferred Value |
|---|---|---|
| Ambient temperature | 0 to 40° C. | 4 to 37° C. |
| Ambient humidity | 0 to 100% | 30 to 80% |
| Ambient gas mixture | Air; Nitrogen; Oxygen; Inert Gasses; Moisture; Carbon Dioxide | |
| Mandrel/vein temperature | 0 to 40° C. | 4 to 37° C. |
| Vein intraluminal volume | 0-50 mL | 0-50 mL |
| Polymer solution and/or stream temperature | 20-50 C. | 20-50 C. |
| Polymer Candidates | PCL; PCL-PLLA/PLA/PGA PVDF-HFP; SIBS; Silk | PCL; PCL-PLLA/PLA/PGA PVDF-HFP; SIBS; Silk |
| Solvent Candidates | HFIP; DMSO; Chloroform; THF; DMF; Dichloromethane; DMAC, Dioxane; Toluene; Water; Acetone; Methanol; Propanol; Ethanol; Lithium Bromide; Aqueous Solutions (alkaline/acidic) | HFIP; DMSO; Chloroform; THF; DMF; Dichloromethane; DMAC, Dioxane; Toluene; Water; Acetone; Methanol; Propanol; Ethanol; Lithium Bromide; Aqueous Solutions (alkaline/acidic) |
| Solution viscosity | 0.001-1000 cP | 0.001-1000 cP |
| Polymer solution density | 0.5-2 g/cc | 0.5-2 g/cc |
| Polymer solution concentration | 0.1-50% (wt/vol) | 0.1-50% (wt/vol) |
| Polymer Solution Flow Rate | 0.01-5 mL/min | 0.01-5 mL/min |
| Polymer Solution Volume | 0.05-50 mL | 0.05-50 mL |
| Thickness of Deposited Polymer (Wrap) | 10-1000 μm | 10-1000 μm |
| Wrap porosity | 50-95% | 50-95% |
| Wrap pore size range | 0.001-500 μm | 0.001-500 μm |
| Wrap pore size distribution | Gaussian; Uniform; Multi-Modal | Gaussian; Uniform; Multi-Modal |
| Wrap permeability (hydraulic; oxygen; nutrient; and cellular) | All; oxygen/nutrients only; | All; oxygen/nutrients only; |
| Fiber size range | 0.1-250 μm | 0.1-250 μm |

Numerous other process input parameters can be used, such as process input parameter that achieve a fiber matrix with one or more portions that include continuously changing properties and/or a fiber matrix with one or more homogenous portions. In a particular embodiment, the fiber matrix comprises at least one homogeneous portion; at least two different homogeneous portions; at least a portion with continuously varying properties; and combinations of these.

During Step 310, one or more process output parameters are monitored during the application. Monitored process output parameters typically include the current tubular graft device diameter and/or thickness. Numerous output parameters can be monitored such as parameters selected from the group consisting of the current (real time) values of: temperature such as device temperature and/or room temperature, room humidity, deposition rate, deposition duration, solvent concentration, viscosity, electrical field strength, mandrel rotation speed, nozzle translation speed, nozzle distance from target; and combinations of these.

In Step 320, which occurs continuously during the application process of Step 310, a comparison of the monitored output parameters is made between this measured value and a target or specification value, hereinafter the process target values. A process target value may be a discrete value or a range of preferred and/or acceptable values for one or more process parameters. If one or more process output parameters are determined to be out of specification, Step 325 is performed wherein a process input parameter is adjusted. Adjusted process input parameter may include but are not limited to: temperature such as device temperature and/or room temperature, humidity, deposition rate, deposition duration, solvent concentration, viscosity, electrical field strength, mandrel rotation speed, nozzle translation speed, nozzle distance from target; and combinations of these. In an alternative embodiment, the process input parameter changed may include a change to the material being deposited or a change to the mix of materials being deposited.

If all the monitored process output parameters of Step 320 are determined to be within specification, Step 330 is performed in which a process completion check is performed. Process completion can be determined in one or more ways, such as the completion of a predetermined process time, or the confirmation that one or more process parameters has reached its intended goal (e.g. desired thickness of the tubular graft device and/or applied fiber matrix.) If process completion is confirmed, the tubular graft device is ready for implantation. If process completion is not confirmed, Steps 310 and 320 continue until completion.

The method of FIG. 37 may further include additional analysis of the tubular graft device and/or a component of the tubular graft device. The analysis may require the application step to be temporarily stopped, and potentially the incomplete tubular graft device to be removed from the holding device. The analysis may be included prior to placing the tubular member on the holding device, or after the fiber application deposition has been completed. This analysis may produce information related to one or more of: device or matrix thickness, device or matrix stiffness, amount of polymer deposited, quantification of solvent in matrix, presence of a puncture; and presence or burning of the tubular member such as burning of a vein. The results of the analysis may require the tubular graft device to be discarded (i.e. not implanted in the patient).

Other embodiments of the invention will be apparent to those skilled in the art from consideration of the specification and practice of the invention disclosed herein. It is intended that the specification and examples be considered as exemplary only, with a true scope and spirit of the invention being indicated by the following claims. In addition, where this application has listed the steps of a method or procedure in a specific order, it may be possible, or even expedient in certain circumstances, to change the order in which some steps are performed, and it is intended that the particular steps of the method or procedure claim set forth herebelow not be construed as being order-specific unless such order specificity is expressly stated in the claim.

We claim:

1. A tubular tissue graft device comprising:
a living tubular tissue harvested from a patient having a wall defining a lumen, the lumen extending from a first end of the living tubular tissue to a second end of the living tubular tissue, the wall having an exterior surface;
an electrospun fiber matrix deposition comprising a polymer, the electrospun fiber matrix deposition surrounding the exterior surface of the living tubular tissue; and
a scaffold disposed relative to the fiber matrix deposition and surrounding the exterior surface of the living tubular tissue,
wherein the electrospun fiber matrix deposition and the scaffold are mechanically intertwined.

2. The device of claim 1, wherein the electrospun fiber matrix deposition surrounds the exterior surface of the living tubular tissue from the first end to the second end of the living tubular tissue.

3. The device of claim 1, wherein the scaffold surrounds the exterior surface of the living tubular tissue from the first end to the second end of the living tubular tissue.

4. The device of claim 1, wherein the exterior surface of the living tubular tissue defines a circumference, the scaffold surrounding the circumference of the living tubular tissue.

5. The device of claim 1, wherein the scaffold comprises at least one of a coil structure, a braided structure, or a knitted structure.

6. The device of claim 1, wherein the scaffold is flexible.

7. The device of claim 1, wherein the scaffold is anisotropic.

8. The device of claim 1, wherein the scaffold and the electrospun fiber matrix deposition are bonded by solvent bonding.

9. The device of claim 1, wherein the scaffold and the fiber matrix comprise a single-layer or a composite structure.

10. The device of claim 1, wherein the scaffold comprises a material is selected from the group consisting of nitinol, stainless steel, a plastic, a polymer, or combinations thereof.

11. The device of claim 1, wherein the scaffold comprises a biodegradable material.

12. The device of claim 1, wherein the scaffold comprises a non-biodegradable material.

13. The device of claim 1, wherein the electrospun fiber matrix deposition comprises a biodegradable material.

14. The device of claim 1, wherein the scaffold provides a radial supporting force to the living tubular tissue, the radial supporting force having a magnitude that changes over time.

15. The device of claim 1, wherein the scaffold provides a radial supporting force to the living tubular tissue, the radial supporting force having a magnitude that varies from the first end to the second end of the living tubular tissue.

16. The device of claim 1, wherein the scaffold comprises at least one of a resiliently biased portion, a plastically deformable portion, or combinations thereof.

17. The device of claim 1, wherein the scaffold is configured to provide an anchoring mechanism for the tubular tissue graft device.

18. The device of claim 1, wherein the electrospun fiber matrix deposition is non-woven.

19. The device of claim 1, wherein the electrospun fiber matrix deposition and the scaffold comprise a polyurethane.

20. The device of claim 1, wherein the electrospun fiber matrix deposition is randomly-arranged.

21. The device of claim 1, wherein the scaffold is not an electrospun scaffold.

* * * * *

UNITED STATES PATENT AND TRADEMARK OFFICE
CERTIFICATE OF CORRECTION

PATENT NO. : 9,622,849 B2
APPLICATION NO. : 13/502759
DATED : April 18, 2017
INVENTOR(S) : Mohammed S. El-Kurdi et al.

It is certified that error appears in the above-identified patent and that said Letters Patent is hereby corrected as shown below:

On the Title Page

Column 1, Item (75) Inventors, Line 9, delete "Wexford," and insert -- Gibsonia, --

Column 2, OTHER PUBLICATIONS, Line 3, delete "%20/" and insert -- %20 --

Column 2, Item (57) ABSTRACT, Line 7, after "procedure." delete "5"

Signed and Sealed this
Twenty-seventh Day of June, 2017

Joseph Matal
*Performing the Functions and Duties of the*
*Under Secretary of Commerce for Intellectual Property and*
*Director of the United States Patent and Trademark Office*